US008722659B2

(12) United States Patent
Clauss et al.

(10) Patent No.: US 8,722,659 B2
(45) Date of Patent: May 13, 2014

(54) QUINAZOLINEDIONE DERIVATIVES, PREPARATION THEREOF AND VARIOUS THERAPEUTIC USES THEREOF

(75) Inventors: Annie Clauss, Paris (FR); Christophe Glaess, Paris (FR); Gilbert Marciniak, Paris (FR); Jean-Francois Nave, Paris (FR); Bertrand Vivet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/268,164

(22) Filed: Oct. 7, 2011

(65) Prior Publication Data
US 2012/0115846 A1 May 10, 2012

Related U.S. Application Data

(63) Continuation of application No. PCT/FR2010/050664, filed on Apr. 7, 2010.

(30) Foreign Application Priority Data

Apr. 9, 2009 (FR) .................................. 09 01760

(51) Int. Cl.
*A01N 43/00* (2006.01)
*A61K 31/33* (2006.01)
*A01N 43/54* (2006.01)
*A61K 31/517* (2006.01)
*A01K 31/00* (2006.01)

(52) U.S. Cl.
USPC .................. 514/210.21; 514/183; 514/266.3

(58) Field of Classification Search
None
See application file for complete search history.

(56) References Cited

U.S. PATENT DOCUMENTS

| 3,879,393 | A | 4/1975 | Havera et al. | |
|---|---|---|---|---|
| 8,242,126 | B2 * | 8/2012 | Clauss et al. | 514/266.22 |
| 2010/0113391 | A1 | 5/2010 | Koga et al. | |
| 2010/0298298 | A1 | 11/2010 | Clauss et al. | |

FOREIGN PATENT DOCUMENTS

| EP | 0040793 | 12/1981 |
|---|---|---|
| EP | 0638567 | 2/1995 |
| FR | 2921926 | 10/2007 |
| WO | WO 93/19068 | 9/1993 |
| WO | WO 99/54284 A1 | 10/1999 |
| WO | WO 01/44228 A2 | 6/2001 |
| WO | WO 2006/092691 A1 | 9/2006 |
| WO | WO 2006/092692 A1 | 9/2006 |
| WO | WO 2007/067946 A2 | 6/2007 |
| WO | WO 2008/119057 A2 | 10/2008 |
| WO | WO 2008/133155 A1 | 11/2008 |
| WO | WO 2009/077680 A1 | 6/2009 |

OTHER PUBLICATIONS

Patani et al., "Bioisosterism: A Rational Approach in Drug Design," Chem. Rev. 1996, 96, 3147-3176.*
Perry, et al., Chemotherapeutic Potential of Phosphodiesterase Inhibitors, Current Opinion in Chemical Biology, vol. 2, No. 4, (1998), pp. 472-481.
Pitts, et al., Identification of Purine Inhibitors of Phosphodiesterase 7 (PDE7), Bioorganic & Medicinal Chemistry Letters, vol. 14, (2004), pp. 2955-2958.
Saldou, et al., Comparison of Recombinant Human PDE4 Isoforms: Interaction With Substrate and Inhibitors, Cell. Signal., vol. 10, No. 6, pp. 427-440, (1998).
Diehn, et al., Genomic Expression Programs and The Integration of the CD28 Costimulatory Signal in T Cell Activation, PNAS, vol. 99, No, 18, (2002), pp. 11796-11801.
West, Solid State Chemistry and its Application, Wiley, New York, (1988), pp. 358 and 365.
Morissette, et al., High-Throughput Crystallization: Polymorphs, Salts, Co-Crystals and Solvates of Pharmaceutical Solids, Advanced Drug Delivery Reviews, vol. 56, pp. 275-300, (2004).
Yin, et al., Carbon-Carbon Coupling Reactions Catalyzed by Heterogeneous Palladium Catalysts, Chem. Rev., (2007), vol. 107, pp. 133-173.
Ahlstrom, et al., Cyclic Nucleotide Phosphodiesterases (PDEs) In Human Osteoblastic Cells; The Effect of PDE Inhibition on Camp Accumulation, Cellular & Molecular Biology Letters, vol. 10, (2005), pp. 305-319.
Bender, et al., Cyclic Nuleotide Phosphodiesterases: Molecular Regulation to Clinical Use, Pharmacological Reviews, (2006), pp. 488-520, vol. 58, No. 3.
Bloom, et al., Identification and Tissue-Specific Expression of PDE7 Phosphodiesterase Splice Variants. PNAS, vol. 93, pp. 14188-14192, (1996).
Gardner, et al., Cloning and Characterization of the Human and Mouse PDE7B, a Novel CAMP-Specific Cyclic Nucleotide Phosphodiesterase, Biochemical and Biophysical Research Communications, vol. 272, pp. 186-192, (2000).
Grassy, et al., Inhibitory Effects on Platelet Aggregation and Cyclic AMP Phosphodiesterase of Azaindolizine-Type Compounds, Chemometrics and Intelligent Laboratory Systems, (1993), pp. 71-84, vol. 20.
Giembycz, et al., Phosphodiesterase 7 (PDE7) as a Therapeutic Target, Drugs of the Future, (2006), vol. 31, No. 3, pp. 207-229.
Glavas, et al., T Cell Activation Up-Regulates Cyclic Nucleotide Phosphodiesterases 8A1 and 7A3, PNAS, (2001), vol. 98, No. 11, pp. 6319-6324.
Han, et al., Alternative Splicing of the High Affinity CAMP-Specific Phosphodiesterase (PDE7A) MRNA in Human Skeletal Muscle and Heart, The Journal of Biological Chemistry, vol. 272, No. 26, (1997), pp. 16152-16157.
Omori, et al., Overview of PDEs and Their Regulation, Circulation Research, (2007), pp. 309-327, vol. 100.

(Continued)

*Primary Examiner* — Brandon Fetterolf
*Assistant Examiner* — Jared D Barsky
(74) *Attorney, Agent, or Firm* — Scully, Scott, Murphy & Presser, P.C.

(57) ABSTRACT

The subject matter of the invention is quinazolinedione derivatives of formula (I), methods for obtaining same and therapeutic uses thereof, such as cancer, diabetes, muscle diseases, bone diseases, cardiovascular diseases, central nervous system diseases, peripheral nervous system diseases, inter alia.

4 Claims, No Drawings

(56) References Cited

OTHER PUBLICATIONS

Kinoshita, et al., Phosphodiesterase Inhibitors, Pentoxifylline and Rolipram, Increase Bone Mass Mainly by Promoting Bone Formation in Normal Mice, Bone, vol. 27, No. 6, pp. 811-817, (2000).

Lee, et al., PDE7A is Expressed in Human B-Lymphocytes and is Up-Regulated by Elevation of Intracellular CAMP, Cellular Signalling, vol. 14, (2002), pp. 277-284.

Li, et al., CD3- and CD28-Dependent Induction of PDE7 Required for T Cell Activation, Science, vol. 283, pp. 848-851, (1999).

Lowe, et al., Stucture-Activity Relationship of Quinazolinedione Inhibitors of Calcium-Independent Phosphodiesterase, J. Med. Chem., (1991), vol. 34, pp. 624-628.

Lugnier et al., Cyclic Nucleotide Phosphidiesterase (PDE) Superfamily: A New Target For The Development of Specific Therapeutic Agents, Pharmacology & Therapeutics, vol. 109, (2006), pp. 366-398.

Movsesian, Therapeutic potential of cyclic nucleotide phosphodiesterase inhibitors in heart failure, Expert Opinion on Investigational Drugs (2000), pp. 963-973, vol. 9, No. 5.

Michaeli, et al., Isolation and Characterization of a Previously Undetected Human CAMP Phosphodiesterase by Complementation of CAMP Phosphodiesterase-Deficient *Saccharomyces cerevisiae*. The Journal of Biological Chemistry, vol. 268, No. 17, (1993), pp. 12925-12932.

Miro, et al., Differential Distribution of CAMP-Specific Phosphodiesterase 7A MRNA in Rat Brain and Peripheral Organs, Synapse, vol. 40, pp. 201-214, (2001).

Mitsunobu, The Use of Diethyl Azodicarboxylate and Triphenylphosphine in Synthesis and Transformation of Natural Products, Synthesis, 1981 pp. 1-28.

Miyamoto, et al., Reduction of Bone Loss by Denbufylline, an Inhibitor of Phosphodiesterase 4, Biochemical Pharmacology, vol. 54, pp. 613-617, (1997).

Nakata, et al., Potential Role of Phosphodiesterase 7 in Human T Cell Function: Comparative Effects of Two Phosphodiesterase Inhibitors, Clin Exp Immunol, (2002), vol. 128, pp. 460-466.

Reyes-Irisarri, et al., Neuronal Expression of CAMP-Specific Phosphodiesterase 7B MRNA In The Rat Brain, Neuroscience, vol. 132, (2005), pp. 1173-1185.

Sasaki, et al., Identification of Human PDE7B, a CAMP-Specific Phosphodiesterase, Biochemical and Biophysical Research Communications, vol. 271, (2000), pp. 575-583.

Smith, et al., Discovery of BRL 60481 [3-(N,N-Dimethylsulfonamido)-4-Methyl-Nitrobenzene], a Selective Inhibitor of Phosphodiesterase 7: In Vitro Studies in Human Monocytes, Lung Macrophages, and CD8 T-Lymphocytes, Molecular Pharmacology, vol. 66, No. 6, pp. 1679-1689, (2004).

Smith, et al., Ubiquitous Expression of Phosphodiesterase 7A in Human Proinflammatory and Immune Cells, Am. J. Physiol. Lung, Cell, Mol Physiol, vol. 284, pp. L279-L289, (2003).

Matsumoto, et al., Phosphodiesterases in the Vascular System, J. Smooth Muscle Res. (2003), pp. 67-86, vol. 39, No. 4.

Waki, et al., Effects of XT-44, a Phosphodiesterase 4 Inhibitor, In Osteoblastgenesis and Osteoclastgenesis in Culture and its Therapeutic Effects in Rat Osteopenia Models, Jpn. J. Pharmacol., vol. 79, pp. 477-483, (1999).

Wang, et al., Cloning, Characterization, and Tissue Distribution of Mouse Phosphodiesterase 7A1, Biochemical and Biophysical Research Communications, vol. 276, pp. 1271-1277, (2000).

International Search Report for WO2010/116088 dated Oct. 14, 2010.

\* cited by examiner

QUINAZOLINEDIONE DERIVATIVES, PREPARATION THEREOF AND VARIOUS THERAPEUTIC USES THEREOF

The invention relates to quinazolinedione derivatives, to processes for obtaining them, to synthetic intermediates thereof and to the therapeutic uses thereof.

The invention relates to quinazolinedione derivatives that may be inhibitors of phosphodiesterase 7 (abbreviated as PDE7). Some of these derivatives may also inhibit phosphodiesterase 8 (abbreviated as PDE8).

The invention also relates to the use of such quinazolinedione derivatives, which are capable of acting as inhibitors of phosphodiesterase 7 (PDE7), or even, for some of these derivatives, which are also capable of acting as inhibitors of phosphodiesterase 8 (PDE8), given that it is not excluded for these same quinazolinedione derivatives also to be capable of acting via other biological/biochemical pathways.

Phosphodiesterases (PDEs) are intracellular enzymes responsible for the hydrolysis of the secondary messengers cAMP (cyclic adenosine-3',5'-monophosphate) and cGMP (cyclic guanosine-3',5'-monophosphate) into inactive 5'-monophosphate nucleotides. cAMP and cGMP play an essential role in cell signalling pathways and intervene in many physiological processes.

The inhibition of phosphodiesterases is reflected by an increase in the intracellular concentrations of cAMP and cGMP, producing the specific activation of the phosphorylation pathways involved in varied functional responses. Increasing the intracellular concentrations of cAMP or cGMP with the aid of selective phosphodiesterase inhibitors appears to be a promising approach for the treatment of various diseases (Bender and Beavo, Pharmacol. Rev. (2006) 58, 488-520). Phosphodiesterase inhibitors are thus of interest as therapeutic agents and as pharmacological tools.

At the present time, eleven families of phosphodiesterases have been identified. They are distinguished by their primary structure, their substrate specificity and their sensitivity towards various specific PDE effectors and inhibitors. Each family is formed from one or more genes that are expressed in different issues in the form of splicing variants (Bender and Beavo, Pharmacol. Rev. (2006) 58, 488-520; Lugnier, Pharmacol. Therapeut. (2006) 109, 366-398).

PDE4, 7 and 8 specifically hydrolyse cAMP, and PDE5, 6 and 9 cGMP.

The PDE7 family is represented by the isoforms PDE7A and PDE7B, originating from two distinct genes.

Human PDE7A (Michaeli et al., J. Biol. Chem. (1993) 268, 12925-12932; Han et al., J. Biol. Chem. (1997) 272, 16152-16157; Wang et al., Biochem. Biophys. Res. Commun. (2000) 276, 1271-1277) and human PDE7B (Sasaki et al., Biochem. Biophys. Res. Commun. (2000), 271, 575-583; Gardner et al., Biochem. Biophys. Res. Commun. (2000) 272, 186-192) selectively hydrolyse cAMP with Michaelis constants (Km) of 0.1 to 0.2 µM and of 0.13 to 0.2 µM, respectively. The catalytic part of PDE7B shows about 67% homology with that of PDE7A.

Three splicing variants are known for PDE7A. PDE7A1 and PDE7A3 are mainly expressed in the cells of the immune system and the lungs, whereas PDE7A2 is essentially expressed in skeletal muscle, the heart and the kidneys. For PDE7B, three variants have also been recently identified (Giembycz and Smith, Drugs Future (2006) 31, 207-229).

The tissue distribution profiles of PDE7A and PDE7B are very different, suggesting that these two isoforms have different physiological functions. Whereas PDE7A is abundantly expressed in haematopoietic cells, the lungs, the placenta, Leydig cells, the spleen, the collecting tubes of the kidneys and the adrenal glands, strong expression of PDE7B is detected in the pancreas, the heart, the thyroid and skeletal muscle (Giembycz and Smith, Drugs Future (2006) 31, 207-229).

The localization of PDE7 in the organs mentioned above suggests that selective PDE7 inhibitors might have uses in the field of muscular, renal, cardiac and pancreatic diseases, such as in the treatment and/or prevention of diabetes.

A co-expression of messenger RNA (mRNA) and of PDE7A and PDE7B is, however, observed in certain tissues. This is the case for osteoblasts (Ahlstrom et al., Cell. Mol. Biol. Lett. (2005) 10, 305-319) and for certain regions of the brain: several zones of the cortex, the dentate gyrus, most of the components of the olfactory system, the striatum, many thalamic nuclei and the pyramidal cells of the hippocampus (Miro et al., Synapse (2001) 40, 201-214; Reyes-Irisarri et al., Neuroscience (2005) 132, 1173-1185). On the other hand, in certain regions of the brain, only one of the two isoforms is expressed. Thus, only the mRNAs of PDE7A and are present in many nuclei of the brain stem. Similarly, mRNAs and PDE7B are present in high concentrations in the nucleus accumbens and the dorsal motor nucleus of the vagus nerve, whereas the mRNAs of PDE7A and are not detected therein (Miro et al., Synapse (2001) 40, 201-214; Reyes-Irisarri et al., Neuroscience (2005) 132, 1173-1185).

The protein PDE7A1 is clearly expressed in blood T lymphocytes, epithelial cell lines of the bronchi, lung fibroblasts and eosinophils (Smith et al., Am. J. Physiol. Lung Cell. Mol. Physiol. (2003) 284: L279-L289). Several reports suggest that PDE7A might play a role in activating T lymphocytes (Li et al., Science (1999) 283, 848-851; Glavas et al., PNAS (2001) 98, 6319-6324; Nakata et al., Clin. Exp. Immunol., (2002) 128, 460-466; Smith et al., Mol. Pharmacol. (2004) 66, 1679-1689). The protein PDE7A1 is also expressed in cells that play a central role in the pathogenesis of asthma and chronic obstructive pulmonary disease (COPD), such as the T lymphocytes (CD4+ and CD8+), monocytes, neutrophils, alveolar macrophages, and smooth muscle cells of the airways and of pulmonary vessels (Smith et al., Am. J. Physiol. Lung Cell Mol. Physiol. (2003) 284: L279-L289). The localization of PDE7A in the pro-inflammatory cells and the cells of the immune system and its potential role in activating T lymphocytes suggest that selective PDE7 inhibitors might have applications in the field of diseases associated with the T lymphocytes and in that of diseases of the lung pathways.

The protein PDE7A is also present in the B lymphocytes and in the cell line of B WSU-CLL lymphocytes originating from a patient suffering from a chronic lymphocytic leukaemia. Treatment of the WSU-CLL cells with IC242, a specific PDE7 inhibitor, increases the expression of PDE7A (Lee et al., Cell Signal (2002) 14, 277-284). Moreover, it has been shown that expression of the protein PDE7B is about 5 to 90 times higher in peripheral blood mononuclear cells (PBMC) of patients suffering from chronic lymphocytic leukaemia (CLL-PBMC) than in PBMC isolated from the blood of normal individuals (WO 2007/067 946). BRL-50481, a selective PDE7 inhibitor, induces dose-dependent apoptosis of CLL-PBMCs, but it has no effect on the PBMCs of normal individuals. These observations suggest that selective PDE7 inhibitors might be effective in treating this type of leukaemia.

Selective PDE4 inhibitors increase bone mineral density in rats and mice, and their effects appear to be associated with a reduction in the activity of osteoclasts and an increase in that of osteoblasts (Miyamoto et al., Biochem. Pharmacol. (1997) 54, 613-617; Waki et al., Jpn J. Pharmacol. (1999) 79, 477-

483; Kinoshita et al., Bone (2000) 27, 811-817). PDE7 activity has been detected in osteoblasts (Ahlstrom et al., Cell Mol. Biol. Lett. (2005) 10, 305-319). By increasing the intracellular concentration of cAMP, PDE7 inhibitors and PDE4 inhibitors might prove to be effective in the treatment of osteopenia and osteoporosis.

Moreover, recent studies (WO 2006/092 691, WO 2006/092 692) report the pharmacological activities of various PDE7 inhibitors in models of neuropathic pain in rats, suggesting applications in the treatment of various types of pain and more particularly in that of neuropathic pain.

Moreover, document WO 2008/119 057 describes a method for treating movement anomalies associated with a neurological movement disorder pathology, such as Parkinson's disease, the treatment method comprising the administration to a patient of an amount of PDE7 inhibitor that is effective for inhibiting the enzymatic activity of PDE7.

One subject of the invention is a compound of general formula (I) below:

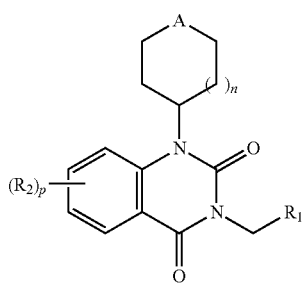

(I)

in which A represents either an oxygen or sulfur atom, or a sulfoxide function (SO function) or a sulfone function ($SO_2$ function);
  n represents the value 0, 1 or 2;
  $R_2$ represents an atom or a group chosen from:
    a hydrogen atom,
    a halogen atom,
    a cyano group,
    a nitro group,
    an aryl, arylalkyl or heteroaryl group,
    a group ($C_1$-$C_6$)alkyl, optionally substituted with a function —$NH_2$, with one or more halogen atoms, with one or more hydroxyl groups, with an alkynyl group, with an alkenyl group, with a group —NHC(O)Rb and/or with a group —NHC(O)NRbRc, Rb and Rc being defined below,
    a group —ORa, Ra being defined below,
    a group NRbRc, Rb and Rc being defined below,
    a group C(O)($C_1$-$C_6$)alkyl,
    an alkenyl group or an alkynyl group, the said groups being optionally substituted with at least one hydroxyl or with at least one halogen atom;
    a group alkyl-S—,
    alkyl-S(O)—, and
    alkyl-S(O)$_2$—,
  p represents the value 1, 2 or 3, it being understood that when p is equal to 2 or 3, then the atoms $R_2$ or the groups $R_2$ may be, respectively, identical or different;
  $R_1$ represents an aryl, arylalkyl or heteroaryl group, the said groups being optionally substituted with (i) an atom $R_3$ or a group $R_3$, or with (ii) 2 or 3 atoms and/or groups $R_3$, the said atoms or groups $R_3$ being, respectively, identical or different, given that $R_3$ represents:
    a hydrogen atom,
    a halogen atom,
    a hydroxyl group,
    a cyano group,
    a group —$SCF_3$,
    a nitro group,
    a group —S(O)$_{0-2}$-alkyl, a group —S(O)$_{0-2}$-heterocycloalkyl, a group —O—$SO_2$-aryl or O—$SO_2$-arylalkyl optionally substituted with one or more halogen atoms;
    an alkyl-amino-alkyl group or a -cycloalkyl-amino-alkyl group, the said groups being optionally substituted on the terminal alkyl,
    an optionally substituted sulfonamide group,
    an aryl, arylalkyl or heteroaryl group, the said group being monocyclic or polycyclic and moreover being optionally substituted with a group ($C_1$-$C_6$)alkyl, with one or more hydroxyl groups, with one or more halogen atoms, with one or more cyano groups and/or with one or more groups ($C_1$-$C_6$)alkoxy,
    a heterocycloalkyl group optionally substituted with a group ($C_1$-$C_6$)alkyl,
    a group ($C_1$-$C_6$)alkyl optionally substituted with:
      one or more halogen atoms,
      an aryl or arylalkyl group that may be substituted with one or more halogen atoms, with one or more groups ($C_1$-$C_6$)alkoxy, with one or more groups ($C_1$-$C_6$)alkyl, with one or more cyano groups and/or with one or more hydroxyl groups,
      a heteroaryl group,
      one or more hydroxyl groups that may be substituted with an aryl or arylalkyl group, which is itself optionally substituted with one or more halogen atoms, or
      a heterocycloalkyl group optionally substituted with a group CO(O)Ra, or with a group ($C_1$-$C_6$)alkyl, Ra being defined below,
    a group —C(O)NRbRc, Rb and Rc being defined below,
    a group —C(O)ORc, or a group —O—C(O)ORc, Rc being defined below,
    a group ($C_1$-$C_6$)alkoxy, optionally substituted with:
      an amino-alkyl group, an amino-cycloalkyl group,
      a cycloalkyl group,
      a heterocycloalkyl group,
      a monocyclic or polycyclic heteroaryl group,
      one or more hydroxyl groups,
      one or more halogen atoms,
      a group ($C_1$-$C_6$)alkoxy,
      a group —C(O)ORc, Rc being defined below,
      a group —C(O)NRbRc, Rb and Rc being defined below, and/or
      an aryl or arylalkyl group, which is itself optionally substituted with at least one atom and/or at least one group, the said atoms and groups being chosen from halogen atoms, a cyano group, groups ($C_1$-$C_6$)alkoxy, —O-haloalkyl groups and haloalkyl groups,
    a group —O-cycloalkyl, —O-aryl or —O-arylalkyl, or a group —O-heterocycloalkyl, the said groups being optionally substituted with:
      an aryl or arylalkyl group, which is itself optionally substituted with one or more halogen atoms, or with a group ($C_1$-$C_6$)alkyl,
      one or more halogen atoms, and/or
      a group ($C_1$-$C_6$)alkyl, which may itself be substituted with an aryl or arylalkyl group,
    a group —NH—CO—NH-aryl, a group —NH—CO—NH-arylalkyl, a group —NH—CO—NH-heteroaryl, or a group —NH—CO—NH—($C_1$-$C_6$)alkyl, the said aryl, arylalkyl, heteroaryl and alkyl being optionally substituted with at least one atom and/or at least one group, the said atoms and groups being chosen from halogen atoms, a cyano group, a nitro group, a hydroxyl group and groups ($C_1$-$C_6$)alkoxy, a group —N—($C_1$-$C_6$)alkyl, the group ($C_1$-$C_6$)alkyl possibly being substituted with at least one aryl or arylalkyl group optionally substituted with at least one halogen atom and/or with at least one group $SO_2$, or a group —NH—C(O)-aryl, a group —NH—C(O)-aralkyl or a group —NH—C(O)-heteroaryl, the said groups being optionally substituted with at least one halogen atom;

Ra represents:
  a hydrogen atom,
  a group ($C_1$-$C_6$)alkyl or a group ($C_1$-$C_6$)cycloalkyl, the said groups being optionally substituted with one or more halogen atoms, with one or more hydroxyl groups, with an aryl or arylalkyl group, with one or more cyano groups and/or with a group —C(O)NRbRc, Rb and Rc being defined below,
  a group ($C_2$-$C_6$)alkynyl,
  an aryl or arylalkyl group, Rb represents:
  a hydrogen atom,
  a group ($C_1$-$C_6$)alkyl optionally substituted with one or more halogen atoms, with one or more hydroxyl, cyano, amino, heterocycloalkyl or ($C_1$-$C_6$)alkoxy groups, or with an aryl or arylalkyl group optionally substituted with one or more halogen atoms,
  a group ($C_3$-$C_6$) cycloalkyl,
  a group ($C_2$-$C_6$) alkenyl or alkynyl,
  a group ($C_1$-$C_6$)alkoxy,
  an aryl or arylalkyl group optionally substituted with one or more halogen atoms;

Rc represents a hydrogen atom, or a group ($C_1$-$C_6$)alkyl optionally substituted with one or more halogen atoms;
  given that in the groups —NRbRc, Rb and Rc may form with the nitrogen atom a heteroaryl or a heterocycloalkyl, the latter groups being optionally substituted;
in the form of the base or of an acid-addition salt.

According to one embodiment, the compound according to the invention is characterized in that n is equal to 1; in the form of the base or of an acid-addition salt.

According to one embodiment, the compound according to the invention is characterized in that p represents the value 1 or 2, it being understood that when p is equal to 2, then the possible combinations are either (i) two identical or different atoms $R_2$, or (ii) an atom $R_2$ and a group $R_2$, or (iii) two identical or different groups $R_2$; in the form of the base or of an acid-addition salt.

According to one embodiment, the compound according to the invention is characterized in that $R_2$ represents an atom or a group chosen from:
  a halogen atom,
  a hydrogen atom,
  a nitro group,
  a cyano group,
  an aryl, arylalkyl or heteroaryl group,
  a group ($C_1$-$C_6$)alkyl, optionally substituted with a function —$NH_2$, with one or more hydroxyl groups, with an alkynyl group, with one or more halogen atoms, with a group —NHC(O)Rb with Rb being an optionally substituted group ($C_1$-$C_6$)alkyl, with a group —NHC(O)—NRbRc with Rb and Rc being hydrogen atoms and/or with an alkenyl group,
  a group —ORa, Ra being chosen from:
    a hydrogen atom,
    a group ($C_1$-$C_6$)alkyl optionally substituted with one or more halogen atoms, with one or more hydroxyl groups, with an aryl or arylalkyl group, with one or more cyano groups and/or with a group —C(O)NRbRc,
    a group ($C_1$-$C_6$)cycloalkyl,
    a group ($C_2$-$C_6$)alkynyl,
    an aryl group,
    an arylalkyl group,
  a group NRbRc, Rb being chosen from a hydrogen atom and a group ($C_1$-$C_6$)alkyl optionally substituted with a group ($C_2$-$C_6$)alkynyl and Rc being a hydrogen atom, or Rb and Rc form with the nitrogen atom a heterocycloalkyl, optionally substituted with a hydroxyl group;
  a group C(O)($C_1$-$C_6$)alkyl, and
  an alkenyl group optionally substituted with at least one halogen atom;
in the form of the base or of an acid-addition salt.

According to another embodiment, the compound according to the invention is characterized in that $R_2$ represents an atom or a group chosen from:
  a halogen atom chosen from bromine, fluorine and iodine,
  a hydrogen atom,
  a nitro group,
  a cyano group,
  an aryl or heteroaryl group chosen from phenyl and pyridyl,
  a group ($C_1$-$C_6$)alkyl, optionally substituted with a function —$NH_2$, with one or more hydroxyl groups, with an alkynyl group, with one or more fluorine atoms, with a group —NHC(O)Rb with Rb being an optionally substituted group ($C_1$-$C_6$)alkyl, with a group —NHC(O)—NRbRc with Rb and Rc being hydrogen atoms and/or with an alkenyl group,
  a group —ORa, Ra being chosen from:
    a hydrogen atom,
    a group ($C_1$-$C_6$)alkyl optionally substituted with one or more halogen atoms, with one or more fluorine atoms, with one or more hydroxyl groups, with a benzyl or phenyl group, with one or more cyano groups and/or with a group —C(O)NRbRc, Rb and Rc being hydrogen atoms,
    a group ($C_1$-$C_6$)cycloalkyl,
    a group ($C_2$-$C_6$)alkynyl,
    a benzyl,
  a group NRbRc, Rb being chosen from a hydrogen atom and a group ($C_1$-$C_6$)alkyl optionally substituted with a group ($C_2$-$C_6$)alkynyl and Rc being a hydrogen atom, or Rb and Rc form with the nitrogen atom a heterocycloalkyl, optionally substituted with a hydroxyl group;
  a group C(O)($C_1$-$C_6$)alkyl, and
  an alkenyl group optionally substituted with at least one fluorine atom;
in the form of the base or of an acid-addition salt.

According to another embodiment, the compound according to any one of the preceding claims is characterized in that p is equal to 2 and the two groups and/or atoms $R_2$ are chosen from:
  a halogen atom, and
  a group —ORa, Ra being chosen from:
    a hydrogen atom, and
    a group ($C_1$-$C_6$)alkyl optionally substituted with one or more halogen atoms or with an aryl group;
in the form of the base or of an acid-addition salt.

According to another embodiment, the compound according to the invention is characterized in that p is equal to 2 and the two groups and/or atoms $R_2$ are chosen from:
  a fluorine atom, and
  a group —ORa, Ra being chosen from:
    a hydrogen atom, and
    a group ($C_1$-$C_6$)alkyl optionally substituted with one or more fluorine atoms or with a phenyl group;
in the form of the base or of an acid-addition salt According to another embodiment, the compound according to the invention is characterized in that $R_1$ is a phenyl or a pyridyl, optionally substituted with (i) an atom $R_3$ or a group $R_3$ or (ii) with two atoms and/or groups $R_3$, the possible combinations then being:
  either two identical or different atoms $R_3$,
  or an atom $R_3$ and a group $R_3$,
  or two identical or different groups $R_3$,
$R_3$ being chosen from hydroxyl and ($C_1$-$C_6$)alkoxy groups, the said groups ($C_1$-$C_6$)alkoxy being optionally substituted with an aryl or arylalkyl group, the said aryl or arylalkyl group itself being optionally substituted with at least one halogen atom;
in the form of the base or of an acid-addition salt.

According to another embodiment, the compound according to the invention is characterized in that $R_1$ is a phenyl or a pyridyl, optionally substituted with (i) an atom $R_3$ or a group $R_3$ or (ii) with two atoms and/or groups $R_3$, the possible combinations then being:
  either two identical or different atoms $R_3$,
  or an atom $R_3$ and a group $R_3$,
  or two identical or different groups $R_3$,
$R_3$ being chosen from hydroxyl and ($C_1$-$C_6$)alkoxy groups, the said groups ($C_1$-$C_6$)alkoxy being optionally substituted with a benzyl group, the said benzyl group itself being optionally substituted with at least one chlorine atom;
in the form of the base or of an acid-addition salt.

Among the compounds of formula (I) that are subjects of the invention, mention may be made of the following compounds:

compound 1: 3-(3,4-dimethoxybenzyl)-6-hydroxy-1-(tetrahydro-2H-pyran-4-yl)quinazoline-2,4(1H,3H)-dione;
compound 2: {[3-(3,4-dimethoxybenzyl)-2,4-dioxo-1-(tetrahydro-2H-pyran-4-yl)-1,2,3,4-tetrahydroquinazolin-6-yl]oxy}acetonitrile;
compound 3: 3-(3,4-dimethoxybenzyl)-6-pyridin-4-yl-1-(tetrahydro-2H-pyran-4-yl)-quinazoline-2,4(1H,3H)-dione hydrochloride;
compound 4: 3-[(6-methoxypyridin-3-yl)methyl]-6-pyridin-4-yl-1-(tetrahydro-2H-pyran-4-yl)-quinazoline-2,4(1H,3H)-dione;
compound 5: 6-bromo-3-[(6-methoxypyridin-3-yl)methyl]-1-(tetrahydro-2H-pyran-4-yl)-quinazoline-2,4(1H,3H)-dione;
compound 6: 6-bromo-3-(3,4-dimethoxybenzyl)-1-(tetrahydro-2H-pyran-4-yl)quinazoline-2,4(1H,3H)-dione
compound 7: 2-({3-[(6-methoxypyridin-3-yl)methyl]-2,4-dioxo-1-(tetrahydro-2H-pyran-4-yl)-1,2,3,4-tetrahydroquinazolin-6-yl}oxy)propanenitrile
compound 8: 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrile
compound 9: ({3-[(6-methoxypyridin-3-yl)methyl]-2,4-dioxo-1-(tetrahydro-2H-pyran-4-yl)-1,2,3,4-tetrahydroquinazolin-6-yl}oxy)acetonitrile
compound 10: 3-(3,4-dimethoxybenzyl)-6-hydroxy-1-(tetrahydro-2H-thiopyran-4-yl)-quinazoline-2,4(1H,3H)-dione
compound 11: {[3-(3,4-dimethoxybenzyl)-2,4-dioxo-1-(tetrahydro-2H-thiopyran-4-yl)-1,2,3,4-tetrahydroquinazolin-6-yl]oxy}acetonitrile
compound 12: 2-{[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}propanenitrile
compound 13: 3-(3,4-dimethoxybenzyl)-6-hydroxy-1-(1-oxidotetrahydro-2H-thiopyran-4-yl)-quinazoline-2,4(1H,3H)-dione
compound 14: {[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}acetonitrile
compound 15: 2-{[3-(3,4-dimethoxybenzyl)-1-(1-oxidotetrahydro-2H-thiopyran-4-yl)-2,4-dioxo-1,2,3,4-tetrahydroquinazolin-6-yl]oxy}propanenitrile (isomer 1)
compound 16: 2-{[3-(3,4-dimethoxybenzyl)-1-(1-oxidotetrahydro-2H-thiopyran-4-yl)-2,4-dioxo-1,2,3,4-tetrahydroquinazolin-6-yl]oxy}propanenitrile (isomer 2)
compound 17: {[3-(3,4-dimethoxybenzyl)-1-(1-oxidotetrahydro-2H-thiopyran-4-yl)-2,4-dioxo-1,2,3,4-tetrahydroquinazolin-6-yl]oxy}acetonitrile (isomer 1)
compound 18: {[3-(3,4-dimethoxybenzyl)-1-(1-oxidotetrahydro-2H-thiopyran-4-yl)-2,4-dioxo-1,2,3,4-tetrahydroquinazolin-6-yl]oxy}acetonitrile (isomer 2)
compound 19: 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrilemethane (1:1) (enantiomer 1)
compound 20: 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrilemethane (1:1) (enantiomer 2)
compound 21: 3-(3,4-dimethoxybenzyl)-6-(prop-2-yn-1-yloxy)-1-(tetrahydro-2H-pyran-4-yl)-quinazoline-2,4(1H,3H)-dione
compound 22: 2-{[3-(3,4-dimethoxybenzyl)-2,4-dioxo-1-(tetrahydro-2H-pyran-4-yl)-1,2,3,4-tetrahydroquinazolin-6-yl]oxy}-2-methylpropanenitrile
compound 23: 2-{[3-(3,4-dimethoxybenzyl)-2,4-dioxo-1-(tetrahydro-2H-pyran-4-yl)-1,2,3,4-tetrahydroquinazolin-6-yl]oxy}-2-methylpropanamide
compound 24: 3-(3,4-dimethoxybenzyl)-6-(2-hydroxyethoxy)-1-(tetrahydro-2H-pyran-4-yl)-quinazoline-2,4(1H,3H)-dione
compound 25: 6-(cyclopropylmethoxy)-3-(3,4-dimethoxybenzyl)-1-(tetrahydro-2H-pyran-4-yl)-quinazoline-2,4(1H,3H)-dione
compound 26: 3-(3,4-dimethoxybenzyl)-6-[(1-methylprop-2-yn-1-yl)oxy]-1-(tetrahydro-2H-pyran-4-yl)quinazoline-2,4(1H,3H)-dione
compound 27: 3-(3,4-dimethoxybenzyl)-6-(3-hydroxyazetidin-1-yl)-1-(tetrahydro-2H-pyran-4-yl)quinazoline-2,4(1H,3H)-dione
compound 28: 3-(3,4-dimethoxybenzyl)-6-(prop-2-yn-1-ylamino)-1-(tetrahydro-2H-pyran-4-yl)-quinazoline-2,4(1H,3H)-dione
compound 29: 3-(3,4-dimethoxybenzyl)-2,4-dioxo-1-(tetrahydro-2H-pyran-4-yl)-1,2,3,4-tetrahydroquinazoline-6-carbonitrile
compound 30: N-{[3-(3,4-dimethoxybenzyl)-2,4-dioxo-1-(tetrahydro-2H-pyran-4-yl)-1,2,3,4-tetrahydroquinazolin-6-yl]methyl}acetamide
compound 31: 1-{[3-(3,4-dimethoxybenzyl)-2,4-dioxo-1-(tetrahydro-2H-pyran-4-yl)-1,2,3,4-tetrahydroquinazolin-6-yl]methyl}urea
compound 32: 3-(3,4-dimethoxybenzyl)-6-[(1-methylprop-2-yn-1-yl)oxy]-1-(tetrahydro-2H-pyran-4-yl)quinazoline-2,4(1H,3H)-dione (enantiomer 1)

compound 33: 3-(3,4-dimethoxybenzyl)-6-[(1-methylprop-2-yn-1-yl)oxy]-1-(tetrahydro-2H-pyran-4-yl)quinazoline-2,4(1H,3H)-dione (enantiomer 2)

compound 34: 3-(3,4-dimethoxybenzyl)-6-iodo-1-(tetrahydro-2H-pyran-4-yl)quinazoline-2,4(1H,3H)-dione compound 35: 3-(3,4-dimethoxybenzyl)-6-[(1-methylprop-2-yn-1-yl)amino]-1-(tetrahydro-2H-pyran-4-yl)quinazoline-2,4(1H,3H)-dione compound 36: 3-(3,4-dimethoxybenzyl)-6-propoxy-1-(tetrahydro-2H-pyran-4-yl)quinazoline-2,4(1H,3H)-dione compound 37: 3-(3,4-dimethoxybenzyl)-6-(2-methylpropoxy)-1-(tetrahydro-2H-pyran-4-yl)-quinazoline-2,4(1H,3H)-dione compound 38: 3-(3,4-dimethoxybenzyl)-6-(1-methylethoxy)-1-(tetrahydro-2H-pyran-4-yl)-quinazoline-2,4(1H,3H)-dione compound 39: 3-(3,4-dimethoxybenzyl)-6-(1-hydroxyethyl)-1-(tetrahydro-2H-pyran-4-yl)-quinazoline-2,4(1H,3H)-dione compound 40: 6-acetyl-3-(3,4-dimethoxybenzyl)-1-(tetrahydro-2H-pyran-4-yl)quinazoline-2,4 (1H,3H)-dione compound 41: 6-(2,3-dihydroxypropoxy)-3-(3,4-dimethoxybenzyl)-1-(tetrahydro-2H-pyran-4-yl)quinazoline-2,4(1H,3H)-dione compound 42: 3-(3,4-dimethoxybenzyl)-6-(2-hydroxypropoxy)-1-(tetrahydro-2H-pyran-4-yl)-quinazoline-2,4(1H, 3H)-dione compound 43: 3-(3,4-dimethoxybenzyl)-6-(1-hydroxy-1-methylethyl)-1-(tetrahydro-2H-pyran-4-yl)quinazoline-2,4(1H,3H)-dione compound 44: 3-(3,4-dimethoxybenzyl)-6-ethenyl-1-(tetrahydro-2H-pyran-4-yl)quinazoline-2,4(1H,3H)-dione compound 45: 3-(3,4-dimethoxybenzyl)-6-(hydroxymethyl)-1-(tetrahydro-2H-pyran-4-yl)-quinazoline-2,4(1H, 3H)-dione compound 46: 3-(3,4-dimethoxybenzyl)-6-(1-hydroxy-1-methylbut-3-yn-1-yl)-1-(tetrahydro-2H-pyran-4-yl) quinazoline-2,4(1H,3H)-dione compound 47: 3-(3,4-dimethoxybenzyl)-6-(2-hydroxyethyl)-1-(tetrahydro-2H-pyran-4-yl)-quinazoline-2,4(1H, 3H)-dione compound 48: 3-(3,4-dimethoxybenzyl)-6-[(1R)-2-hydroxy-1-methylethoxy]-1-(tetrahydro-2H-pyran-4-yl)quinazoline-2,4(1H,3H)-dione compound 49: 3-(3,4-dimethoxybenzyl)-6-ethoxy-1-(tetrahydro-2H-pyran-4-yl)quinazoline-2,4(1H,3H)-dione compound 50: 3-(3,4-dimethoxybenzyl)-6-(2-fluoroethoxy)-1-(tetrahydro-2H-pyran-4-yl)-quinazoline-2,4(1H,3H)-dione compound 51: 3-(3,4-dimethoxybenzyl)-1-(tetrahydro-2H-pyran-4-yl)-6-(2,2,2-trifluoroethoxy)quinazoline-2,4(1H, 3H)-dione compound 52: 3-(3,4-dimethoxybenzyl)-6-[(1S)-2-hydroxy-1-methylethoxy]-1-(tetrahydro-2H-pyran-4-yl)quinazoline-2,4(1H,3H)-dione compound 53: 6-(2,2-difluoroethoxy)-3-(3,4-dimethoxybenzyl)-1-(tetrahydro-2H-pyran-4-yl)-quinazoline-2,4(1H, 3H)-dione compound 54: 3-(3,4-dimethoxybenzyl)-1-(tetrahydro-2H-pyran-4-yl)-6-(3,3,3-trifluoropropoxy)quinazoline-2,4 (1H,3H)-dione compound 55: 3-(3,4-dimethoxybenzyl)-6-{[(1R)-1-methylpropyl]oxy}-1-(tetrahydro-2H-pyran-4-yl)quinazoline-2,4(1H,3H)-dione compound 56: 3-(3,4-dimethoxybenzyl)-6-{[(1S)-1-methylpropyl]oxy}-1-(tetrahydro-2H-pyran-4-yl)quinazoline-2,4(1H,3H)-dione compound 57: 3-(3,4-dimethoxybenzyl)-6-[2-fluoro-1-(fluoromethyl)ethoxy]-1-(tetrahydro-2H-pyran-4-yl) quinazoline-2,4(1H,3H)-dione compound 58: 3-(3,4-dimethoxybenzyl)-6-[(1S)-2-fluoro-1-methylethoxy]-1-(tetrahydro-2H-pyran-4-yl)quinazoline-2,4(1H,3H)-dione compound 59: 6-(2,2-difluoroethenyl)-3-(3,4-dimethoxybenzyl)-1-(tetrahydro-2H-pyran-4-yl)-quinazoline-2,4 (1H,3H)-dione compound 60: 3-(3,4-dimethoxybenzyl)-6-(fluoromethyl)-1-(tetrahydro-2H-pyran-4-yl)-quinazoline-2,4(1H,3H)-dione compound 61: 3-(3,4-dimethoxybenzyl)-7-fluoro-6-hydroxy-1-(tetrahydro-2H-pyran-4-yl)-quinazoline-2,4(1H, 3H)-dione compound 62: 6-(benzyloxy)-3-(3,4-dimethoxybenzyl)-7-fluoro-1-(tetrahydro-2H-pyran-4-yl)-quinazoline-2,4(1H, 3H)-dione compound 63: 6-(2,2-difluoroethoxy)-3-(3,4-dimethoxybenzyl)-7-fluoro-1-(tetrahydro-2H-pyran-4-yl)quinazoline-2,4(1H,3H)-dione compound 64: 3-[4-(benzyloxy)-3-methoxybenzyl]-6-[(1,3-difluoropropan-2-yl)oxy]-7-fluoro-1-(tetrahydro-2H-pyran-4-yl)quinazoline-2,4(1H,3H)-dione compound 65: 3-{4-[(3,4-dichlorobenzyl)oxy]-3-methoxybenzyl}-6-[(1,3-difluoropropan-2-yl)oxy]-7-fluoro-1-(tetrahydro-2H-pyran-4-yl)quinazoline-2,4(1H,3H)-dione compound 66: 3-(3,4-dimethoxybenzyl)-6-nitro-1-(tetrahydro-2H-pyran-4-yl)quinazoline-2,4(1H,3H)-dione compound 67: 6-amino-3-(3,4-dimethoxybenzyl)-1-(tetrahydro-2H-pyran-4-yl)quinazoline-2,4(1H,3H)-dione compound 68: 6-[(1,3-difluoropropan-2-yl)oxy]-7-fluoro-3-(4-hydroxy-3-methoxybenzyl)-1-(tetrahydro-2H-pyran-4-yl)quinazoline-2,4(1H,3H)-dione;

in the form of the base or of an acid-addition salt.

The quinazolidinedione derivatives that are the subject of the invention, which may prove to be powerful PDE7 inhibitors or PDE7 and PDE8 inhibitors depending on the derivatives, or which may act via other biological pathways, may be used as medicaments or for the preparation of medicaments.

The compounds of general formula (I) may comprise one or more asymmetric centres. They may thus exist in the form of enantiomers or diastereoisomers. These enantiomers and diastereoisomers, and also mixtures thereof, including racemic mixtures, form part of the invention.

The pure enantiomers of the compounds of the invention may be obtained from enantiomerically pure precursors or by chromatography on chiral phases, or alternatively, when the compounds comprise acid or amine functions, via selective crystallization of the diastereoisomeric salts obtained by reacting the compounds (I) with, respectively, chiral amines or acids.

By virtue of their structure, the compounds of general formula (I) may also exist in the form of isomers of rotamer or atropoisomer type.

The compounds of formula (I) may also exist in the form of bases or of acid-addition salts. Such addition salts form part of the invention.

These salts are advantageously prepared with pharmaceutically acceptable acids, but the salts of other acids that are useful, for example, for purifying or separating the compounds of general formula (I) also form part of the invention.

The compounds of general formula (I) may also be in crystalline, amorphous or oily form, these forms forming part of the invention.

The compounds of general formula (I) may also be in the form of hydrates or solvates, i.e. in the form of associations or combinations with one or more water molecules or with a solvent. Such hydrates and solvates also form part of the invention.

According to the present invention, the N-oxides of the compounds comprising an amine also form part of the invention.

The compounds of formula (I) according to the present invention also include those in which one or more hydrogen, carbon or halogen, especially chlorine or fluorine, atoms have been replaced with the radioactive isotopes thereof, for example tritium or deuteriurm for replacing hydrogen, or carbon-14 for replacing carbon-12. Such labelled compounds may be useful in research, metabolism or pharmacokinetic studies or in biological and pharmacological trials as tools, or even as medicaments, in particular for compounds comprising deuteriurm.

In the context of the invention, the following definitions apply:
- in ($C_1$-$C_6$), the numerical indices determine the possible number of carbon atoms present in the group that it defines. Thus, for example, ($C_1$-$C_6$)alkyl represents a group as defined previously, which may contain from 1 to 6 carbon atoms;
- the term "alkyl" means a linear or branched, saturated aliphatic group; for example, a linear or branched carbon-based chain of 1 to 6 carbon atoms, especially a methyl, ethyl, propyl, isopropyl, butyl, isobutyl, sec-butyl, tert-butyl or pentyl; when an alkyl group is substituted with one or more halogen atoms or with one or more groups as indicated in the definitions, these substitutions may be borne by the same carbon atom and/or by different carbon atoms;
- an alkynyl group means a linear or branched, monounsaturated or polyunsaturated aliphatic group comprising, for example, one or two acetylenic unsaturations. For example, a $C_2$-$C_6$ alkynyl group may represent an ethynyl, propynyl, etc.;
- an alkenyl group means a linear or branched, monounsaturated or polyunsaturated aliphatic group comprising, for example, one or two ethylenic unsaturations. For example, a group $C_2$-$C_6$ alkenyl may represent an ethenyl, propenyl, butenyl, etc.;
- the terms "alkoxy" and "alkyloxy" mean a group —O-alkyl containing a saturated, linear or branched aliphatic chain. Thus, by way of example, ($C_1$-$C_6$)alkoxy represents a group —O—($C_1$-$C_6$)alkyl, the group ($C_1$-$C_6$) alkyl being defined previously;
- the term "halogen atom" means a fluorine, a chlorine, a bromine or an iodine;
- the term "heterocycloalkyl" means an optionally substituted saturated ring comprising from 3 to 8 atoms and comprising at least one heteroatom such as nitrogen, sulfur or oxygen, or several identical or different heteroatoms. For example, a heterocycloalkyl may be a monocyclic heterocycloalkyl such as: an azetidine, a pyrrolidine, a piperidine, a tetrahydropyran, a morpholine, a piperazine, an azepine, etc.;
- the term "cycloalkyl" means a carbon-based ring preferably containing from 3 to 8 carbon atoms, the said ring being saturated and optionally substituted. By way of example, mention may be made of cyclopropyl, methylcyclopropyl, cyclobutyl, cyclopentyl and cyclohexyl groups;
- the term "aryl" means a cyclic aromatic group containing between 6 and 10 carbon atoms. Examples of aryl groups that may be mentioned phenyl and naphthyl;
- an arylalkyl group: an aryl group, as defined above, substituted with at least one alkyl group, as defined above. Advantageously, they are -alkylene-aryl radicals. An example that may be mentioned is benzyl, i.e. the radical —$CH_2$—Ph;
- the term "heteroaryl" means an aromatic system comprising one or more heteroatoms such as nitrogen, oxygen or sulfur atoms and possibly being monocyclic or polycyclic, i.e. comprising from 2 to 5 rings. When the system is polycyclic, at least one of the rings is aromatic. The nitrogen atoms may be in the form of N-oxides.

Examples of monocyclic heteroaryl groups that may be mentioned include monocyclic heteroaryls such as thiazole, thiadiazole, thiophene, imidazole, triazole, tetrazole, pyridine, furan, oxazole, isoxazole, oxadiazole, pyrrole, pyrazole, pyrimidine and pyridazine.

Examples of polycyclic heteroaryl groups that may be mentioned include bicyclic heteroaryls, such as indole, benzofuran, benzimidazole, benzothiophene, benzotriazole, benzothiazole, benzoxazole, quinoline, isoquinoline, indazole, quinazoline, phthalazine, quinoxaline, naphthyridine, 2,3-dihydro-1H-indole, 2,3-dihydrobenzofuran, 2,3-dihydroindene, tetrahydroquinoline, tetrahydroisoquinoline or tetrahydroisoquinazoline;
- a sulfonamide group means a group corresponding to the formula $SO_2$—N-alkyl or $SO_2$—N-cycloalkyl, alkyl and cycloalkyl being as defined above;
- a trifluoromethylthio group is defined by the formula —S—$CF_3$,
- the terms "phenoxy group" and "benzyloxy group" mean, respectively, groups $C_6H_5$—O— and $C_6H_5$—$CH_2$—O—, in which the group $C_6H_5$ (also represented by the abbreviation Ph).

Among the compounds that are subjects of the invention, mention may be made of a group of compounds of formula (I) in which $R_1$ represents an aryl group, in particular a phenyl, or a heteroaryl group, in particular a pyridyl group, all the other substituents and indices being as defined in the general formula (I) defined above.

In the text hereinbelow, the term "leaving group" means a group that can be readily replaced, with loss of an electron pair, by breaking a heterolytic bond. This group may thus be readily replaced with another group, for example during a substitution reaction. Such leaving groups are, for example, halogens or an activated hydroxyl group such as a mesylate, tosylate, triflate, etc. Examples of leaving groups and references for preparing them are given in "Advanced Organic Chemistry", J. March, 3rd edition, Wiley Interscience, pp. 310-316.

The term "protecting group PG" means a group that prevents the reactivity of a function or position during a chemical reaction liable to affect it, and which restores the function after cleavage according to methods known to those skilled in the art.

The term "temporary protecting group for amines or alcohols" means protecting groups such as those described in *Protective Groups in Organic Synthesis*, Greene T. W. and Wuts P. G. M., published by Wiley Interscience, 1999, and in *Protecting Groups*, Kocienski P. J., 1994, Georg Thieme Verlag.

Examples that may be mentioned of temporary protecting groups for amines include benzyls, carbamates, (such as tert-butyloxycarbonyl, which is cleavable in acidic medium, or benzyloxycarbonyl, which is cleavable by hydrogenolysis), temporary protecting groups for carboxylic acids: alkyl esters (such as methyl, ethyl or tert-butyl, which may be hydrolysed in basic or acidic medium) and hydrogenolysable benzyl groups, temporary protecting groups for alcohols or phenols such as tetrahydropyranyl, methyloxymethyl or methylethoxymethyl, tert-butyl and benzyl groups, temporary protecting groups for carbonyl derivatives such as linear or cyclic acetals, for instance 1,3-dioxan-2-yl or 1,3-dioxolan-2-yl; and reference may be made to the well-known general methods described in *Protective Groups*, mentioned above.

Depending on the case, a person skilled in the art will be capable of selecting the appropriate protecting groups.

In the general synthetic schemes that follow, the starting materials and the reagents, when their preparation method is not described, are commercially available or described in the literature, or else may be prepared according to the described methods or methods known to those skilled in the art.

The compounds of formula (I) may comprise protecting groups for other functions that are generated subsequently in one or more other steps.

The compounds of the present invention may be prepared according to schemes 1 to 7 that follow. These synthetic routes serve merely as illustrations and are not in any way limiting. A person skilled in the art can without difficulty adapt the teaching below to the compounds of formula (I) for which A, $R_1$, $R_2$, n, p and optionally $R_3$, Ra, Rb and Rc are defined in the general formula (I). He will be capable of selecting, in the light of his knowledge and of the literature, the appropriate protecting groups allowing the introduction of all the groups or functions described in the present invention.

For the sake of clarity, n and p=1 and the position of $R_2$ have been chosen as indicated in the schemes.

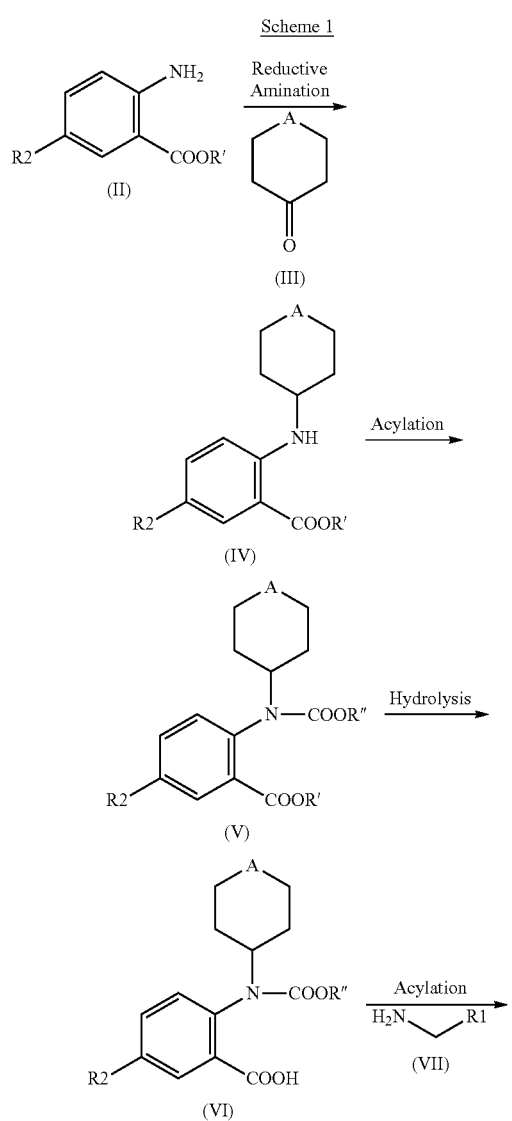

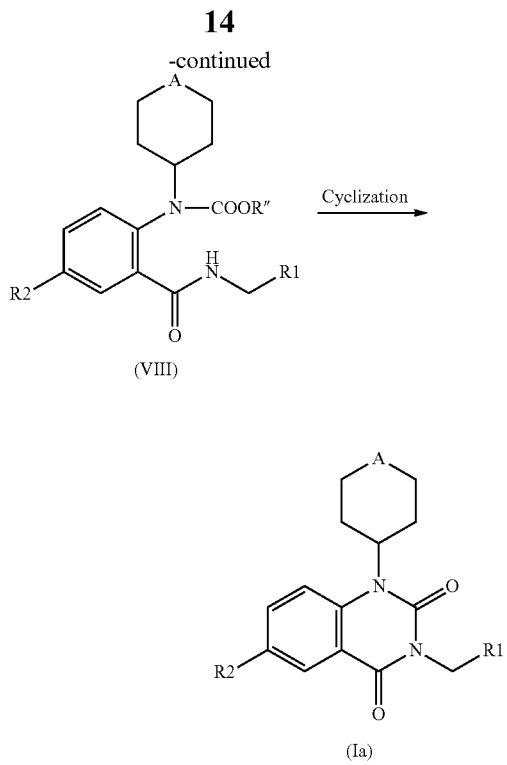

The compounds corresponding to formula (Ia), in which A, $R_1$ and $R_2$ are as defined in the general formula (I), may be prepared according to Scheme 1.

The compounds of formula (IV) are obtained via a reductive amination reaction by reacting a compound of formula (II) in which $R_2$ is as defined in the general formula (I) and R' represents a group $(C_1-C_6)$alkyl, with a compound of formula (III), in which A is as defined in the general formula (I), in acidic medium and in the presence of a reducing agent such as sodium triacetoxyborohydride. The compounds of formula (IV) thus formed are then acylated according to methods that are well known to those skilled in the art, with an alkyl or aryl chloroformate to give the compound of formula (V) in which R" represents a group $(C_1-C_6)$alkyl or a substituted aryl group. A hydrogenolysis reaction in basic medium gives the compounds of formula (VI), which, via a coupling reaction with a compound of formula (VII), in which $R_1$ is as defined for the compounds of general formula (I), leads to the compounds of formula (VIII). An intramolecular cyclization reaction in basic medium gives the quinazolinedione derivatives of formula (Ia).

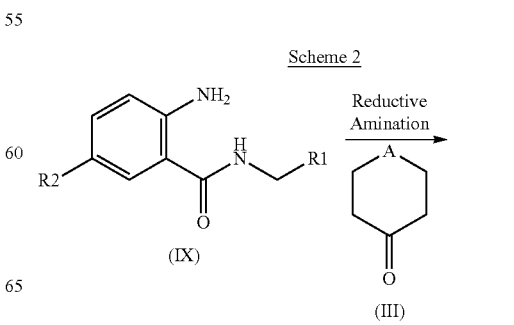

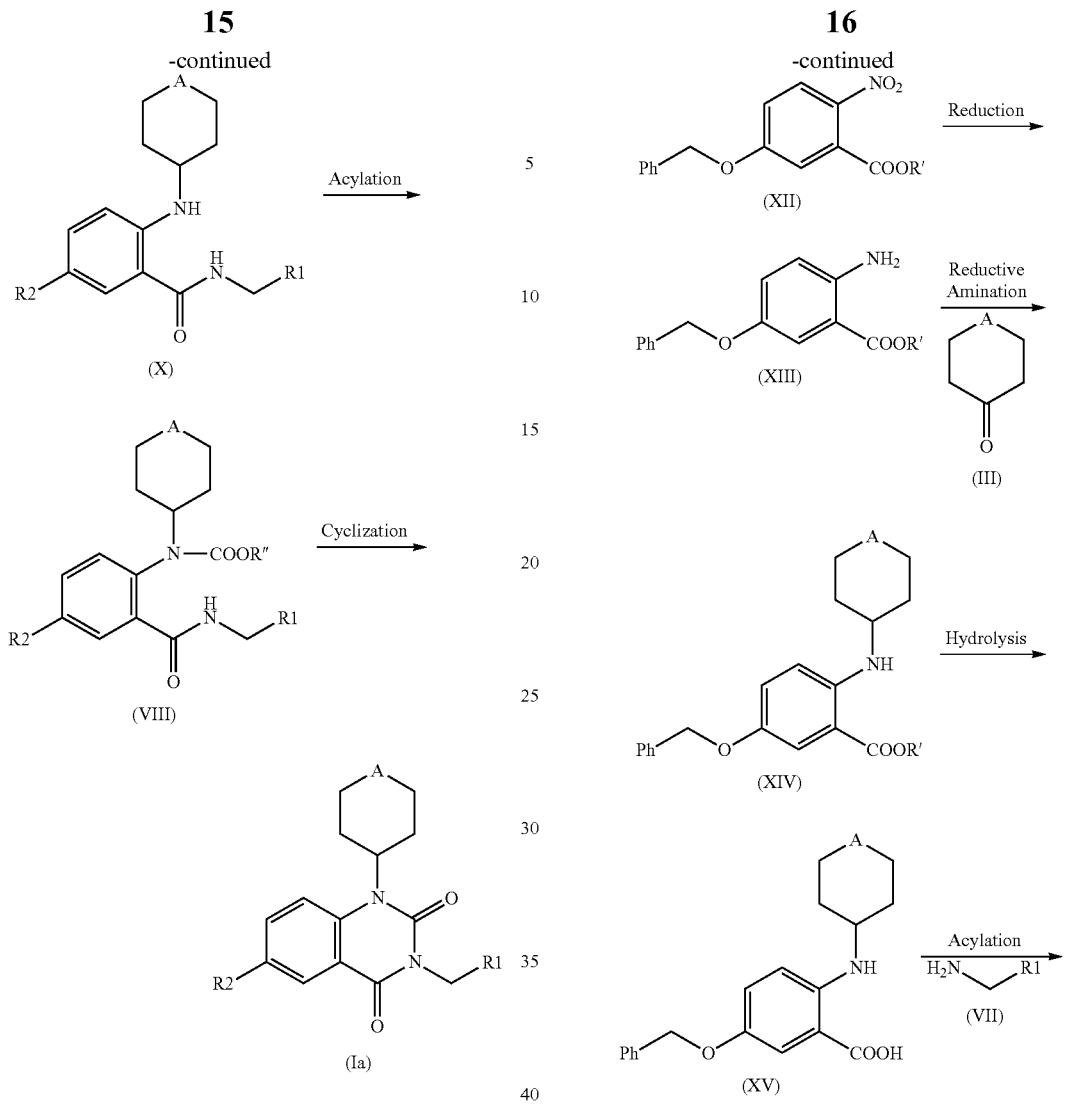

Alternatively, the compounds corresponding to formula (Ia), in which A, $R_1$ and $R_2$ are as defined in the general formula (I), may be prepared according to Scheme 2. A reductive amination reaction between the compound of formula (IX), in which $R_1$ and $R_2$ are as defined in the general formula (I), and a compound of formula (III), in which A is as defined in the general formula (I), in acidic medium and in the presence of a reducing agent such as sodium triacetoxyborohydride, gives the compounds of formula (X). The compounds of formula (X) are then acylated with an alkyl or aryl chloroformate to give the compounds of formula (VIII) in which R" represents a group $(C_1\text{-}C_6)$alkyl or a substituted aryl group, which, via an intramolecular cyclization reaction in basic medium, gives, as previously, the quinazolinedione derivatives of formula (Ia).

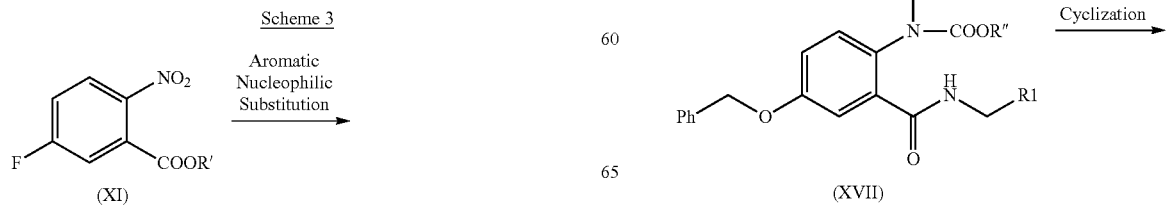

-continued

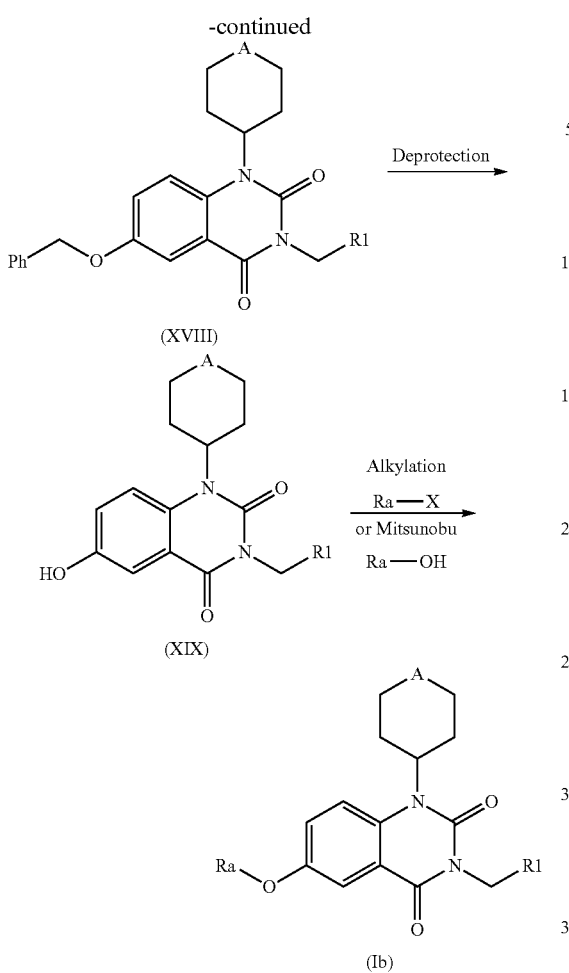

The compounds of formula (Ib) for which R₂ represents —ORa, Ra being as defined for the compounds of general formula (I), may be prepared according to Scheme 3.

The compounds of formula (XII) are obtained via an aromatic nucleophilic substitution reaction involving a compound of formula (XI) in which R' represents a group (C₁-C₆)alkyl, and benzyl alcohol in the presence of a base. Reduction of the nitro group of the compounds of formula (XII) leads to the corresponding anilino derivatives (XIII). A reductive amination reaction with a compound of formula (III) in which A is as defined in the general formula (I), in acidic medium and in the presence of a reducing agent such as sodium triacetoxyborohydride, gives the compounds of formula (XIV), which, via a hydrogenolysis reaction in basic medium, gives the compounds of formula (XV). This is followed by an acylation reaction with a compound of formula (VII), leading to the production of compounds of formula (XVI) and then a second acylation reaction with an alkyl or aryl chloroformate leads to the production of compounds of formula (XVII), and finally an intramolecular cyclization reaction in the presence of a base gives the compounds of formula (XVIII). The compounds of formula (XIX), obtained by deprotection of the benzyloxy group of the compounds of formula (XVIII), are then subjected, for example, to an alkylation reaction with an alkylating agent of the type Ra-X in which Ra is as defined for the compounds of general formula (I) and X represents a leaving group (for instance a halogen atom), in the presence of a base such as caesium carbonate (Cs₂CO₃), or alternatively to a Mitsunobu reaction (Synthesis 1981, 1) with an alcohol of the type Ra-OH, Ra being as defined for the compound of general formula (I), to give the compounds of formula (Ib).

Scheme 4

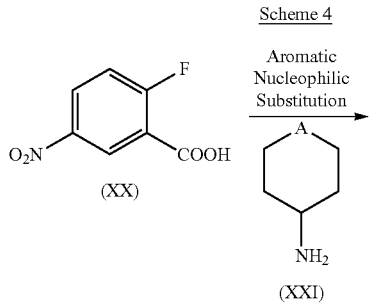

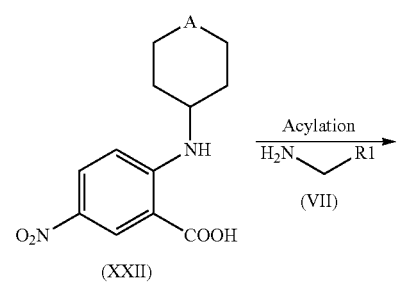

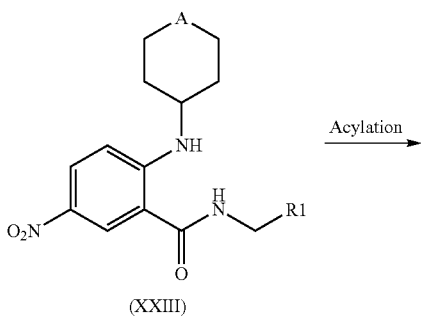

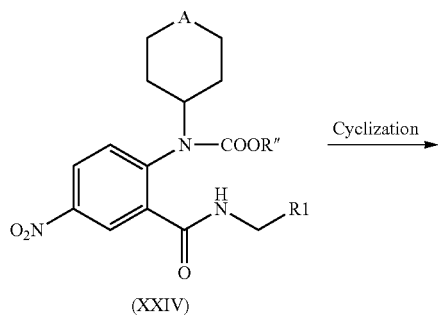

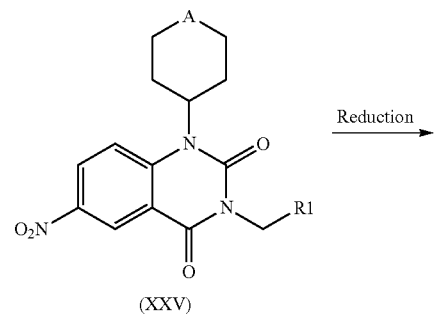

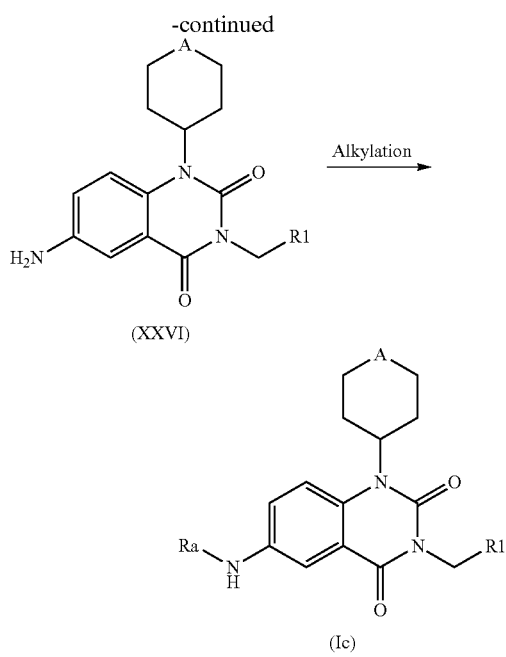

The compounds of formula (Ic) in which $R_2$ represents —NHRa, Ra, A and $R_1$ being as defined for the compound of general formula (I), may be prepared according to Scheme 4.

A nucleophilic substitution reaction between a compound of formula (XX) and a compound of formula (XXI) leads to the compounds of formula (XXII), which are then converted into compounds of formula (XXV) via the sequence of reactions equivalent to those described in the preceding schemes, namely (i) a first acylation reaction of the compounds of formula (XXII) with an amine of formula (VII), with $R_1$ as defined for the general formula (I), leading to the production of the compounds of formula (XXIII), (ii) a second acylation reaction with an alkyl or aryl chloroformate to form the compounds of formula (XXIV) and then (iii) a cyclization reaction leading to the formation of the said compounds of formula (XXV). The compounds of formula (XXVI), obtained via reduction of the nitro group of the compounds of formula (XXV) to amine, are then subjected to an alkylation reaction with an alkylating agent of the type Ra—X in which Ra is as defined for the compounds of general formula (I) and X represents a leaving group (for instance a halogen atom) in the presence of a base such as caesium carbonate ($Cs_2CO_3$) to give the compounds of formula (Ic).

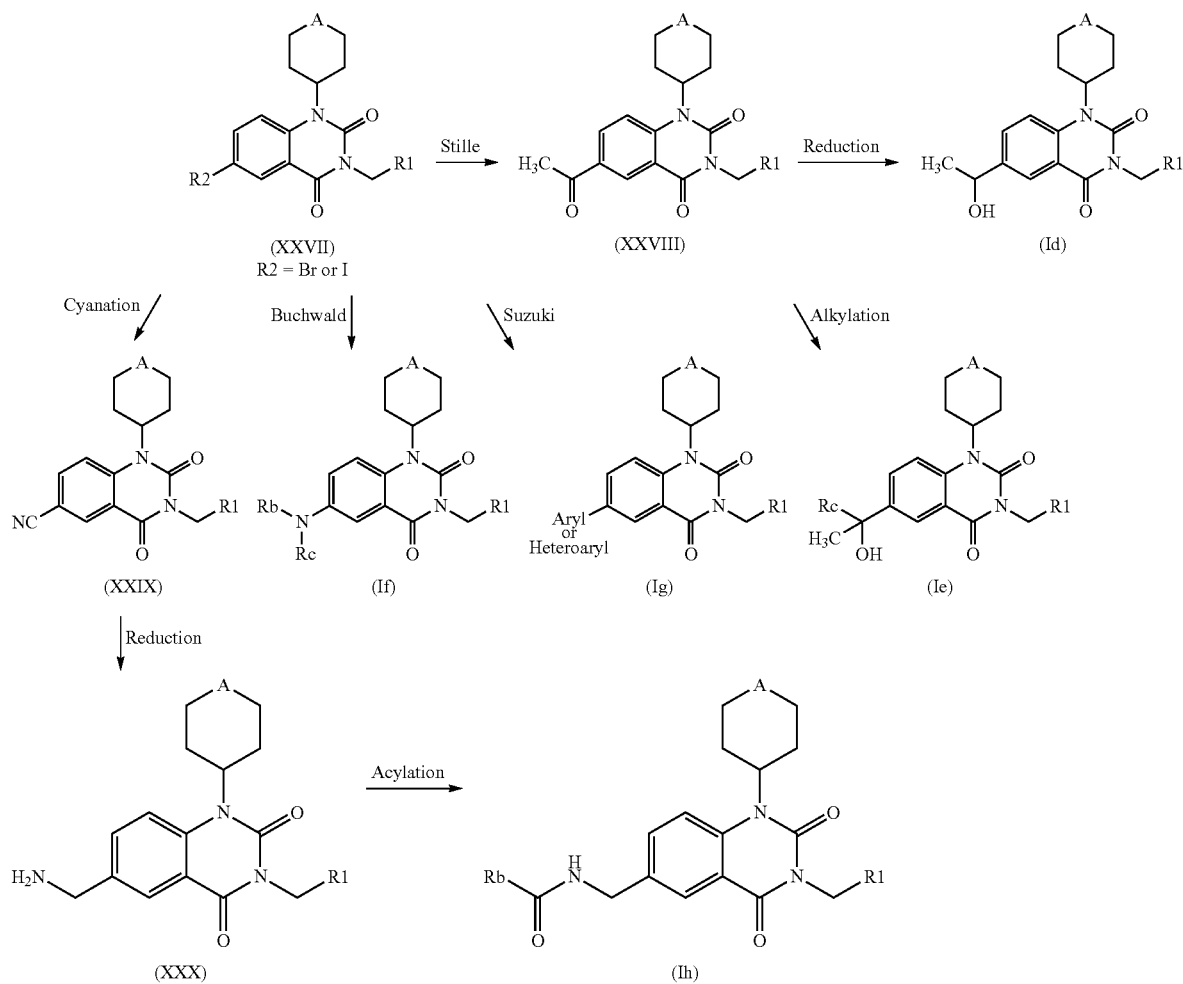

Scheme 5

The compounds of formulae (Id), (Ie), (If), (Ig) and (Ih) in which A, $R_1$, Rb and Rc are as defined for the compound of general formula (I) may be prepared according to Scheme 5. They are obtained from the compounds of formula (XXVII) in which $R_2$ represents a halogen atom, preferably a bromine or iodine atom.

The compounds of formula (XXVIII) are obtained from the compounds of formula (XXVII) via a reaction of Stille type (see, for example, Chemical Review 2007, 107, 133-173). Reduction or alkylation of the carbonyl group makes it possible to obtain the compounds of formulae (Id) and (Ie), respectively.

The compounds of formulae (If) and (Ig) are obtained from the compounds of formula (XXVII) via a reaction of Buchwald or Suzuki type (see, for example, Chemical Review 2007, 107, 133-173), respectively.

The compounds of formula (XXIX), obtained via a cyanation reaction (see, for example, Chemical Review 2007, 107, 133-173) on compounds of formula (XXVII), lead to the compounds of formula (XXX) via a reduction reaction. Finally, an acylation reaction of the compounds of formula (XXX) leads to the compounds of formula (Ih).

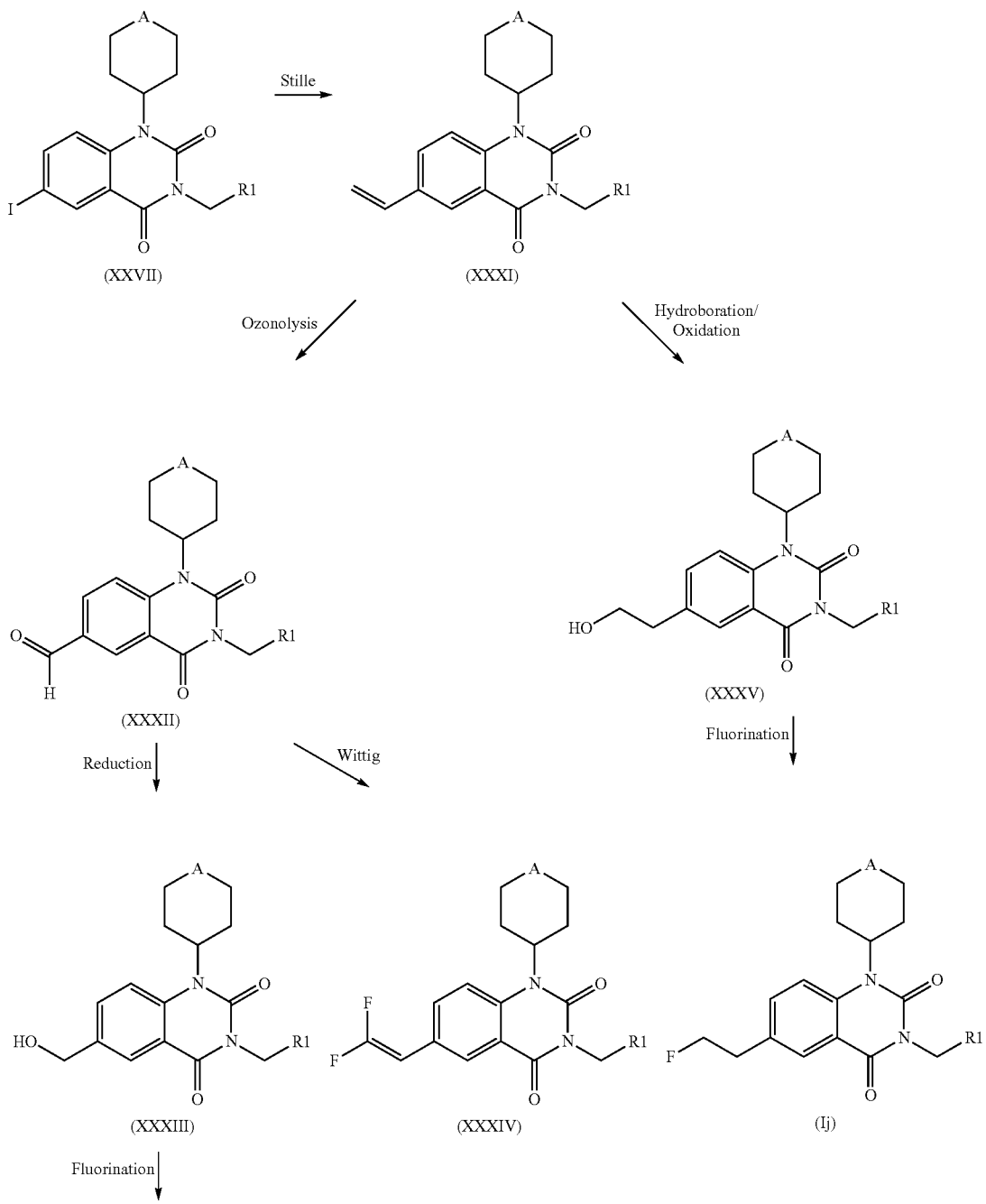

Scheme 6

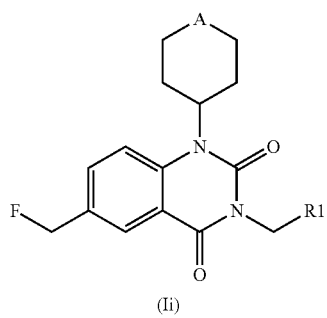

(Ii)

The compounds of formulae (Ii) and (Ij) in which A and $R_1$ are as defined in the general formula (I) and $R_2$ is as indicated in Scheme 6 may be prepared according to Scheme 6.

The compounds of formula (XXXI), obtained from the compounds of formula (XXVII) via a Stille reaction, lead to the aldehydes of formula (XXXII) via an ozonolysis reaction. The compounds of formula (XXXIII) are obtained via a reduction reaction on the said aldehydes of formula (XXXII) using, for example, boron hydrides as reducing agent. The compounds of formula (Ii) are obtained from the compounds of formula (XXXIII) via a fluorination reaction using, for example, DAST as fluorinating agent. The compounds of formula (XXXIV) are obtained from the compounds of formula (XXXII) via a reaction of Wittig type.

Finally, the compounds of formula (XXXV), obtained from the compounds of formula (XXXI) via a hydroboration/oxidation reaction, are converted into compounds of formula (I) via a fluorination reaction.

Scheme 7

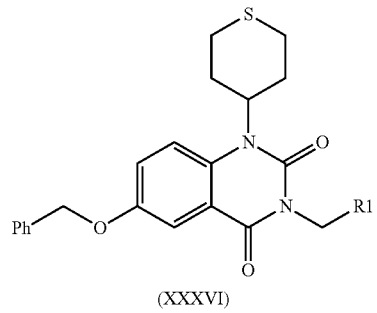

(XXXVI)

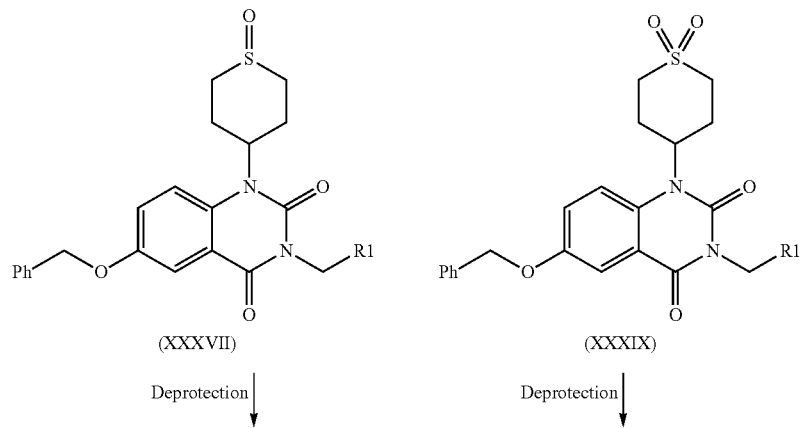

-continued

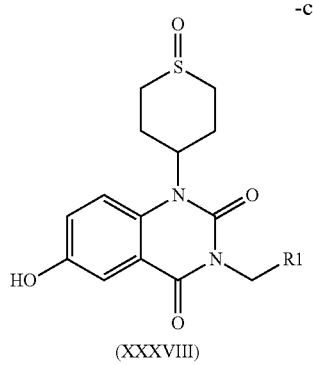

(XXXVIII)

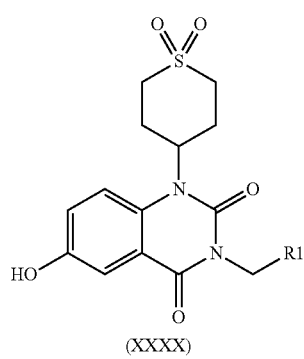

(XXXX)

Alkylation ↓

Alkylation ↓

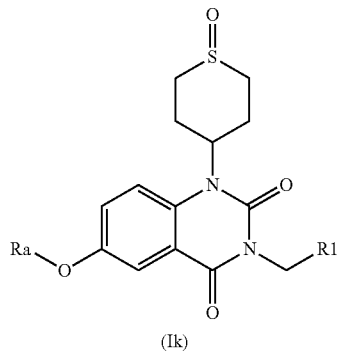

(Ik)

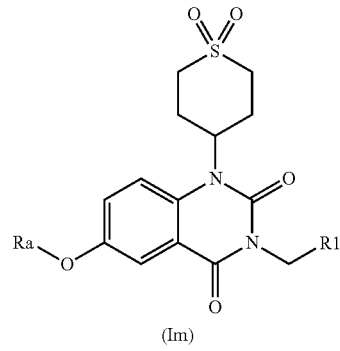

(Im)

The compounds of formulae (Ik) and (Im) for which A represents a group SO or $SO_2$, respectively, may be prepared according to Scheme 7. For the sake of clarity, the group $R_2$ of general formula (I) has been chosen as indicated in Scheme 7.

Oxidation of the compounds of formula (XXXVI) in the presence of potassium periodate leads to the sulfoxide derivatives of formula (XXXVII). The benzyloxy group is deprotected, for example via a hydrogenolysis reaction, to give the compounds of formula (XXXVIII), which, via an alkylation reaction with an alkylating agent of the type Ra—X in which Ra is as defined for the compound of general formula (I) and X represents a leaving group (for instance a halogen atom) in the presence of a base such as caesium carbonate ($Cs_2CO_3$), leads to the compounds of formula (Ik).

By analogy, the sulfone derivatives of formula (Im) may be prepared according to the same synthetic scheme, with the exception of the oxidation step, which may be performed with Oxone® to give the compounds of formula (XXXIX).

The numbers of the illustrated compounds refer to those given in Table 1 below, which illustrates the chemical structures and the physical properties of a number of compounds according to the invention.

The software used for the nomenclature of the named compounds in the present invention is ACD/Name® (www.acd-labs.com).

TABLE 1

| Compound No. | STRUCTURE | NOMENCLATURE | NMR | MASS |
|---|---|---|---|---|
| 1 | 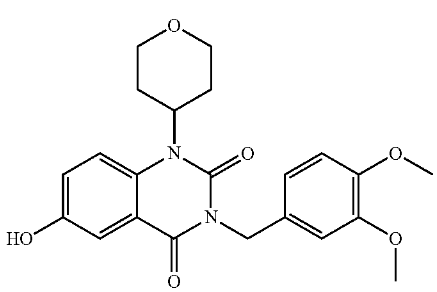 [SMILES: COc1ccc(Cn2c(=O)c3cc(O)ccc3n(C3CCOCC3)c2=O)cc1OC] | 3-(3,4-dimethoxybenzyl)-6-hydroxy-1-(tetrahydro-2H-pyran-4-yl)quinazoline-2,4(1H,3H)-dione | 1H NMR (600 MHz, DMSO-$d_6$) δ ppm 1.61 (d, 2 H) 2.68 (qd, 2 H) 3.50 (t, 2 H) 3.70 (s, 3 H) 3.71 (s, 3 H) 3.95 (dd, 2 H) 4.69 (br. t, 1 H) 5.03 (s, 2 H) 6.82 (dd, 1 H) 6.87 (d, 1 H) 6.98 (d, 1 H) 7.18 (dd, 1 H) 7.40 (d, 1 H) 7.60 (d, 1 H) 10.20 (br. s., 1 H) | 413 |

TABLE 1-continued

| Compound No. | STRUCTURE | NOMENCLATURE | NMR | MASS |
|---|---|---|---|---|
| 2 | 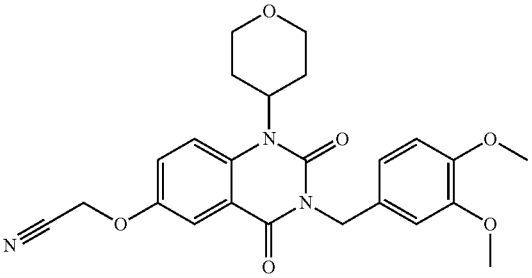 | {[3-(3,4-dimethoxybenzyl)-2,4-dioxo-1-(tetrahydro-2H-pyran-4-yl)-1,2,3,4-tetrahydroquinazolin-6-yl]oxy}acetonitrile | 1H NMR (600 MHz, DMSO-$d_6$) δ ppm 1.65 (d, 2 H) 2.67 (qd, 2 H) 3.51 (t, 2 H) 3.57 (br. s., 1 H) 3.70 (s, 3 H) 3.71 (s, 3 H) 3.95 (dd, 2 H) 4.71 (br. t., 1 H) 4.88 (s, 2 H) 5.04 (s, 2 H) 6.82 (d, 1 H) 6.85 (d, 1 H) 6.99 (s, 1 H) 7.40 (dd, 1 H) 7.62 (d, 1 H) 7.75 (d, 1 H) | 452 |
| 3 | 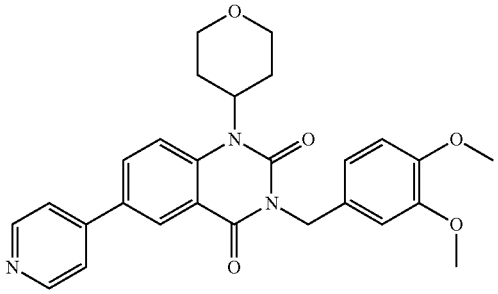 [SMILES: COc1ccc(Cn2c(=O)c3cc(-c4ccncc4)ccc3n(C3CCOCC3)c2=O)cc1OC] | 3-(3,4-dimethoxybenzyl)-6-pyridin-4-yl-1-(tetrahydro-2H-pyran-4-yl)quinazoline-2,4(1H,3H)-dione hydrochloride | 1H NMR (600 MHz, DMSO-$d_6$) δ ppm 1.70 (d, 2 H) 2.71 (qd, 2 H) 3.57 (t, 2 H) 3.71 (s, 3 H) 3.72 (s, 3 H) 3.98 (dd, 2 H) 4.86 (t, 1 H) 5.09 (s, 2 H) 6.88 (s, 2 H) 7.02 (s, 1 H) 8.01 (d, 1 H) 8.36 (d, 3 H) 8.63 (d, 1 H) 8.90 (d, 2 H) | 474 |
| 4 | 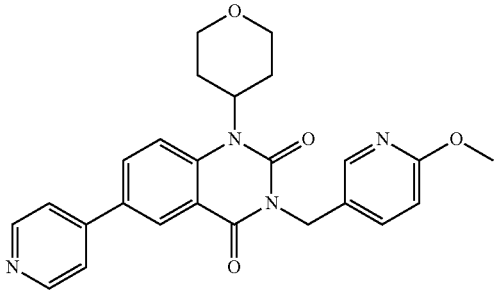 [SMILES: COc1ccc(Cn2c(=O)c3cc(-c4ccncc4)ccc3n(C3CCOCC3)c2=O)cn1] | 3-[(6-methoxypyridin-3-yl)methyl]-6-pyridin-4-yl-1-(tetrahydro-2H-pyran-4-yl)quinazoline-2,4(1H,3H)-dione | 1H NMR (600 MHz, DMSO-$d_6$) δ ppm 1.69 (d, 2 H) 2.70 (dq, 2 H) 3.55 (t, 2 H) 3.81 (s, 3 H) 3.97 (dd, 2 H) 4.83 (t, 1 H) 5.09 (s, 2 H) 6.77 (d, 1 H) 7.72 (dd, 1 H) 7.78 (d, 2 H) 7.93 (d, 1 H) 8.20 (dd, 1 H) 8.22 (d, 1 H) 8.44 (d, 1 H) 8.66 (d, 2 H) | 445 |
| 5 | 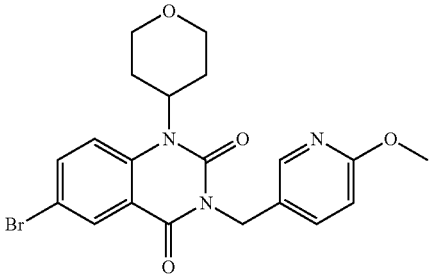 [SMILES: COc1ccc(Cn2c(=O)c3cc(Br)ccc3n(C3CCOCC3)c2=O)cn1] | 6-bromo-3-[(6-methoxypyridin-3-yl)methyl]-1-(tetrahydro-2H-pyran-4-yl)quinazoline-2,4(1H,3H)-dione | 1H NMR (600 MHz, DMSO-$d_6$) δ ppm 1.64 (d, 2 H) 2.63 (qd, 2 H) 3.50 (t, 2 H) 3.80 (s, 3 H) 3.94 (dd, 2 H) 4.73 (br. t., 1 H) 5.03 (s, 2 H) 6.75 (d, 1 H) 7.68 (dd, 1 H) 7.76 (d, 1 H) 7.89 (dd, 1 H) 8.12 (d, 1 H) 8.18 (s, 1 H) | 446 |
| 6 | 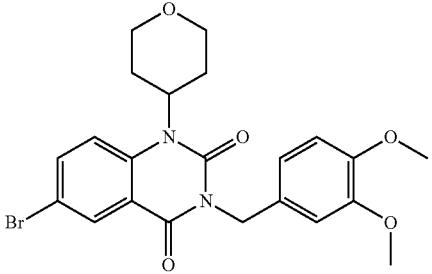 [SMILES: COc1ccc(Cn2c(=O)c3cc(Br)ccc3n(C3CCOCC3)c2=O)cc1OC] | 6-bromo-3-(3,4-dimethoxybenzyl)-1-(tetrahydro-2H-pyran-4-yl)quinazoline-2,4(1H,3H)-dione | 1H NMR (600 MHz, DMSO-$d_6$) δ ppm 1.64 (d, 2 H) 2.65 (qd, 2 H) 3.50 (t, 2 H) 3.70 (s, 3 H) 3.70 (s, 3 H) 3.94 (dd, 2 H) 4.72 (br. t, 1 H) 5.03 (s, 2 H) 6.82-6.84 (m, 1 H) 6.84-6.86 (m, 1 H) 6.98 (s, 1 H) 7.76 (d, 1 H) 7.89 (dd, 1 H) 8.12 (d, 1 H) | 475 |

TABLE 1-continued

| Compound No. | STRUCTURE | NOMENCLATURE | NMR | MASS |
|---|---|---|---|---|
| 7 | 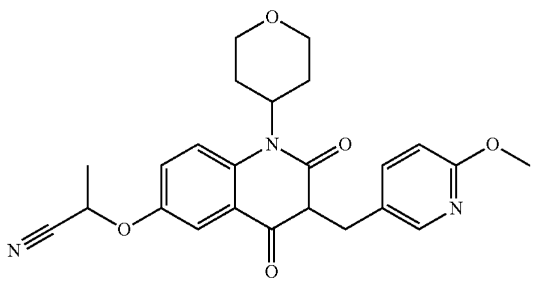 [SMILES: COc1ccc(CC2C(=O)c3cc(OC(C)C#N)ccc3N(C3CCOCC3)C2=O)cn1] | 2-({3-[(6-methoxypyridin-3-yl)methyl]-2,4-dioxo-1-(tetrahydro-2H-pyran-4-yl)-1,2,3,4-tetrahydroquinazolin-6-yl}oxy)propanenitrile | 1H NMR (600 MHz, DMSO-$d_6$) δ ppm 1.65 (d, 2 H) 1.71 (d, 3 H) 2.67 (qd, 2 H) 3.52 (t, 2 H) 3.81 (s, 3 H) 3.95 (dd, 2 H) 4.74 (br. t., 1 H) 5.06 (s, 2 H) 5.59 (q, 1 H) 6.77 (d, 1 H) 7.50 (dd, 1 H) 7.70 (dd, 1 H) 7.74 (d, 1 H) 7.82 (d, 1 H) 8.20 (d, 1 H) | 437 |
| 8 | 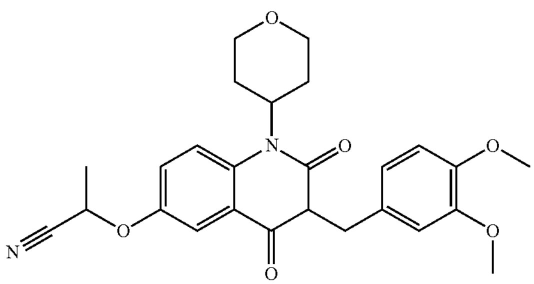 | 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrile | 1H NMR (600 MHz, DMSO-$d_6$) δ ppm 1.64 (d, 2 H) 1.70 (d, 3 H), 2.67 (qd, 2 H) 3.51 (t, 2 H) 3.70 (s, 3 H) 3.70 (s, 3 H) 3.94 (dd, 2 H) 4.72 (t, 1 H) 5.05 (s, 2 H) 5.58 (q, 1 H) 6.83 (m, 1 H) 6.86 (m, 4 H) 6.99 (s, 1 H) 7.49 (dd, 1 H) 7.73 (d, 1 H) 7.81 (d, 1 H) | 466 |
| 9 | 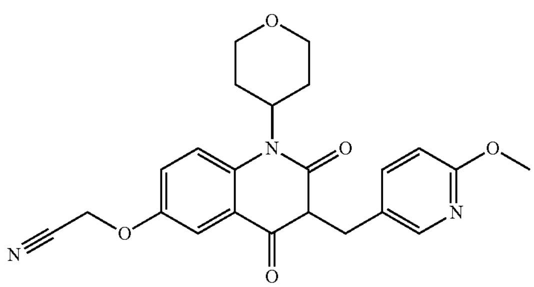 [SMILES: COc1ccc(CC2C(=O)c3cc(OCC#N)ccc3N(C3CCOCC3)C2=O)cn1] | ({3-[(6-methoxypyridin-3-yl)methyl]-2,4-dioxo-1-(tetrahydro-2H-pyran-4-yl)-1,2,3,4-tetrahydroquinazolin-6-yl}oxy)acetonitrile | 1H NMR (600 MHz, DMSO-$d_6$) δ ppm 1.65 (dd, 2 H) 2.67 (qd, 2 H) 3.52 (t, 2 H) 3.81 (s, 3 H) 3.95 (dd, 2 H) 4.74 (br. t., 1 H) 5.06 (s, 2 H) 5.28 (s, 2 H) 6.76 (d, 1 H) 7.49 (dd, 1 H) 7.70 (m, 2 H) 7.81 (d, 1 H) 8.20 (d, 1 H) | 423 |
| 10 | 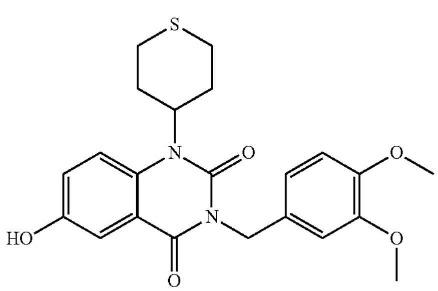 | 3-(3,4-dimethoxybenzyl)-6-hydroxy-1-(tetrahydro-2H-thiopyran-4-yl)quinazoline-2,4(1H,3H)-dione | 1H NMR (600 MHz, DMSO-$d_6$) δ ppm 1.98 (d, 2 H) 2.72 (br. m., 4 H) 2.92 (t, 2 H) 3.69 (s, 3 H) 3.70 (s, 3 H) 4.31 (br. m., 1 H) 5.02 (s, 2 H) 6.79-6.81 (d, 1 H) 6.84-6.86 (d, 1 H) 6.97 (s, 1 H) 7.18 (dd, 1 H) 7.41 (d, 1 H) 7.57 (d, 1 H) 9.78 (br. s., 1 H) | 429 |
| 11 | 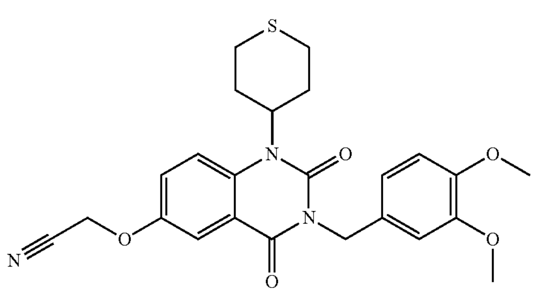 | {[3-(3,4-dimethoxybenzyl)-2,4-dioxo-1-(tetrahydro-2H-thiopyran-4-yl)-1,2,3,4-tetrahydroquinazolin-6-yl]oxy}acetonitrile | 1H NMR (600 MHz, DMSO-$d_6$) δ ppm 2.02 (d, 2 H) 2.70 (m, 4 H) 2.95 (br. t., 2 H) 3.70 (s, 3 H) 3.71 (s, 3 H) 4.40 (m, 1 H) 5.05 (s, 2 H) 5.28 (s, 2 H) 6.82-6.85 (d, 1 H) 6.85-6.88 (d, 1 H) 6.99 (s, 1 H) 7.49 (dd, 1 H) 7.70 (d, 1 H) 7.76 (d, 1 H) | 468 |

TABLE 1-continued

| Compound No. | STRUCTURE | NOMENCLATURE | NMR | MASS |
|---|---|---|---|---|
| 12 | 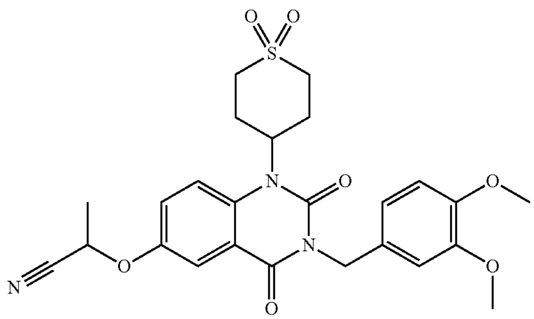 | 2-{[3-(3,4-dimethoxybenzyl)-1-(1,1-dioxido-tetrahydro-2H-thiopyran-4-yl)-2,4-dioxo-1,2,3,4-tetrahydroquinazolin-6-yl]oxy}propanenitrile | 1H NMR (500 MHz, DMSO-d<sub>6</sub>) δ ppm 1.74 (d, 3 H) 2.10 (d, 2 H) 3.17 (m, 4 H) 3.54 (t, 2 H) 3.73 (s, 3 H) 3.74 (s, 3 H) 4.83 (br. s., 1 H) 5.08 (s, 2 H) 5.65 (q, 1 H) 6.89 (m, 2 H) 7.03 (s, 1 H) 7.59 (dd, 1 H) 7.77 (d, 1 H) 7.85 (d, 1 H) | 514 |
| 13 | 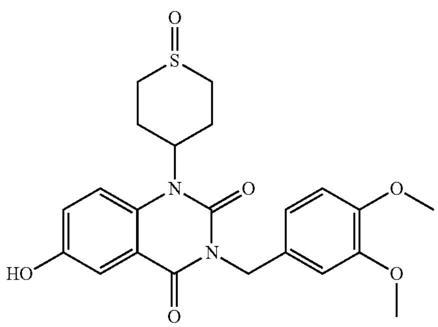 [SMILES: COc1ccc(Cn2c(=O)c3cc(O)ccc3n(C3CCS(=O)CC3)c2=O)cc1OC] | 3-(3,4-dimethoxybenzyl)-6-hydroxy-1-(1-oxido-tetrahydro-2H-thiopyran-4-yl)quinazoline-2,4(1H,3H)-dione | 1H NMR (500 MHz, DMSO-d<sub>6</sub>) δ ppm 1.48 (d, 1.2 H) 1.74 (d, 0.8 H) 2.54-2.81 (m, 4 H) 3.12 (br. t, 2 H) 3.48 (s, 6 H) 4.29 (br. s., 0.4 H) 4.45 (br. s., 0.6 H) 4.78 (s, 0.8 H) 4.81 (s, 1.2 H) 6.56-6.65 (m, 2 H) 6.73 (d, 0.4 H) 6.76 (d, 0.6 H) 6.98 (dd, 1 H) 7.19 (d, 0.4 H) 7.21 (d, 0.6 H) 7.43 (d, 1 H) 9.68 (br, s, 1 H) | 445 |
| 14 | 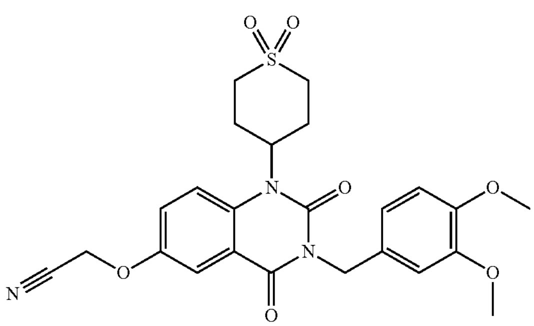 [SMILES: COc1ccc(Cn2c(=O)c3cc(OCC#N)ccc3n(C3CCS(=O)(=O)CC3)c2=O)cc1OC] | {[3-(3,4-dimethoxybenzyl)-1-(1,1-dioxido-tetrahydro-2H-thiopyran-4-yl)-2,4-dioxo-1,2,3,4-tetrahydroquinazolin-6-yl]oxy}acetonitrile | 1H NMR (500 MHz, DMSO-d<sub>6</sub>) δ ppm 2.06 (d, 2 H) 3.07 (br. m., 2 H) 3.14 (br. d, 2 H) 3.51 (br. t, 2 H) 3.71 (s, 3 H) 3.72 (s, 3 H) 4.80 (br. s., 1 H) 5.05 (s, 2 H) 5.30 (s, 2 H) 6.79-6.89 (m, 2 H) 7.00 (s, 1 H) 7.55 (dd, 1 H) 7.71 (d, 1 H) 7.82 (d, 1 H) | 500 |
| 15 | 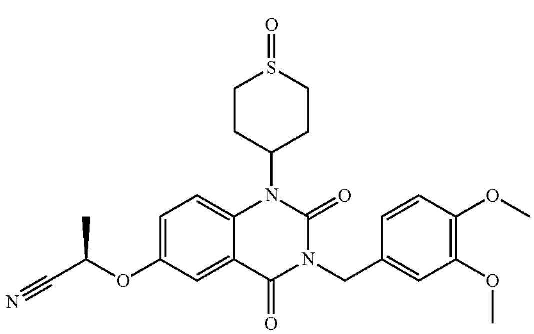 [SMILES: COc1ccc(Cn2c(=O)c3cc(O[C@H](C)C#N)ccc3n(C3CCS(=O)CC3)c2=O)cc1OC] | 2-{[3-(3,4-dimethoxybenzyl)-1-(1-oxidotetrahydro-2H-thiopyran-4-yl)-2,4-dioxo-1,2,3,4-tetrahydro-quinazolin-6-yl]oxy}propanenitrile (isomer 1) | 1H NMR (500 MHz, DMSO-d<sub>6</sub>) δ ppm 1.72 (d, 3 H) 1.76 (d, 2 H) 2.92 (t, 2 H) 3.03 (d, 2 H) 3.24 (br. s., 2 H) 3.71 (s, 3 H) 3.72 (s, 3 H) 4.62 (br. s., 1 H) 5.07 (s, 2 H) 5.61 (q, 1 H) 6.87 (s, 2 H) 7.01 (s, 1 H) 7.55 (dd, 1 H) 7.76 (d, 1 H) 7.82 (br. d., 1 H) | 498 |

TABLE 1-continued

| Compound No. | STRUCTURE | NOMENCLATURE | NMR | MASS |
|---|---|---|---|---|
| 16 | 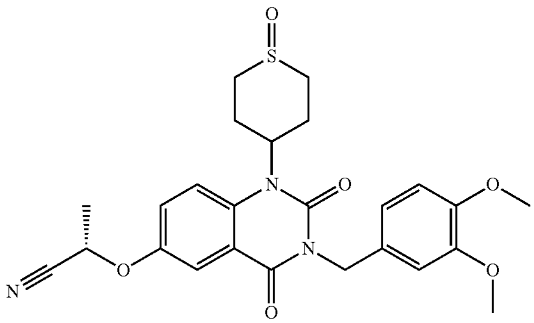 [SMILES: COc1ccc(Cn2c(=O)c3cc(O[C@@H](C)C#N)ccc3n(C3CCS(=O)CC3)c2=O)cc1OC] | 2-{[3-(3,4-dimethoxybenzyl)-1-(1-oxidotetrahydro-2H-thiopyran-4-yl)-2,4-dioxo-1,2,3,4-tetrahydro-quinazolin-6-yl]oxy}propanenitrile (isomer 2) | 1H NMR (500 MHz, DMSO-$d_6$) δ ppm 1.71 (d, 3 H) 2.01 (d, 2 H) 2.81 (dt, 2 H) 2.99 (t, 2 H) 3.36 (d, 2 H) 3.70 (s, 3 H) 3.71 (s, 3 H) 4.75 (br. s., 1 H) 5.03 (s, 2 H) 5.61 (q, 1 H) 6.83 (dd, 1 H) 6.85 (d, 1 H) 6.97 (s, 1 H) 7.53 (dd, 1 H) 7.73 (d, 1 H) 7.85 (d, 1 H) | 498 |
| 17 | 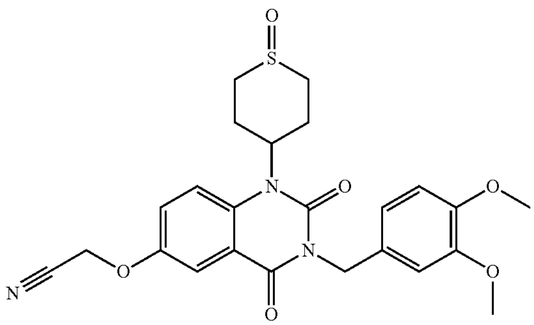 [SMILES: COc1ccc(Cn2c(=O)c3cc(OCC#N)ccc3n(C3CCS(=O)CC3)c2=O)cc1OC] | {[3-(3,4-dimethoxybenzyl)-1-(1-oxidotetrahydro-2H-thiopyran-4-yl)-2,4-dioxo-1,2,3,4-tetrahydro-quinazolin-6-yl]oxy}acetonitrile (isomer 1) | 1H NMR (500 MHz, DMSO-$d_6$) δ ppm 1.75 (d, 2 H) 2.91 (dt, 2 H) 3.03 (d, 2 H) 3.20 (br. s., 2 H) 3.71 (s, 3 H) 3.72 (s, 3 H) 4.65 (br. s, 1 H) 5.07 (s, 2 H) 5.29 (s, 2 H) 6.87 (s, 2 H) 7.00 (s, 1 H) 7.54 (dd, 1 H) 7.72 (d, 1 H) 7.82 (d, 1 H) | 484 |
| 18 | 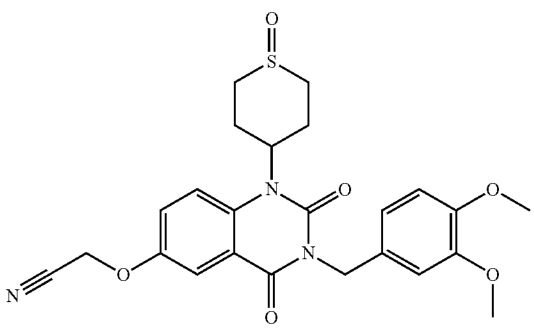 | {[3-(3,4-dimethoxybenzyl)-1-(1-oxidotetrahydro-2H-thiopyran-4-yl)-2,4-dioxo-1,2,3,4-tetrahydro-quinazolin-6-yl]oxy}acetonitrile (isomer 2) | 1H NMR (500 MHz, DMSO-$d_6$) δ ppm 2.00 (d, 2 H) 2.81 (dt, 2 H) 3.00 (t, 2 H) 3.36 (d, 2 H) 3.70 (s, 3 H) 3.71 (s, 3 H) 4.75 (br. s., 1 H) 5.03 (s, 2 H) 5.29 (s, 2 H) 6.82 (dd, 1 H) 6.85 (d, 1 H) 6.98 (d, 1 H) 7.52 (dd, 1 H) 7.69 (d, 1 H) 7.84 (d, 1 H) | 484 |
| 19 | 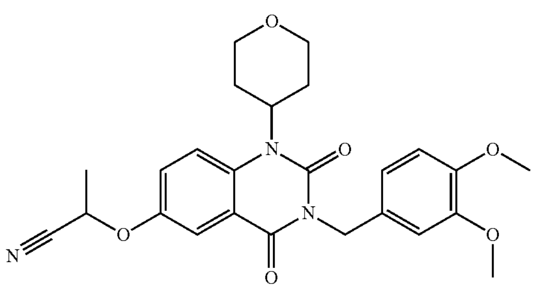 [SMILES: COc1ccc(Cn2c(=O)c3cc(OC(C)C#N)ccc3n(C3CCOCC3)c2=O)cc1OC] | 2-{[3-(3,4-dimethoxybenzyl)-2,4-dioxo-1-(tetrahydro-2H-pyran-4-yl)-1,2,3,4-tetrahydro-quinazolin-6-yl]oxy}propanenitrilemethane (1:1) (enantiomer 1) | 1H NMR (600 MHz, DMSO-$d_6$) δ ppm 1.64 (d, 2 H) 1.70 (d, 3 H) 2.67 (qd, 2 H) 3.51 (t, 2 H) 3.69 (s, 3 H) 3.70 (s, 3 H) 3.94 (dd, 2 H) 4.72 (t, 1 H) 5.04 (s, 2 H) 5.58 (q, 1 H) 6.83 (d, 1 H) 6.86 (d, 1 H) 6.99 (s, 1 H) 7.49 (dd, 1 H) 7.73 (d, 1 H) 7.81 (d, 1 H) | 466 |
| 20 | 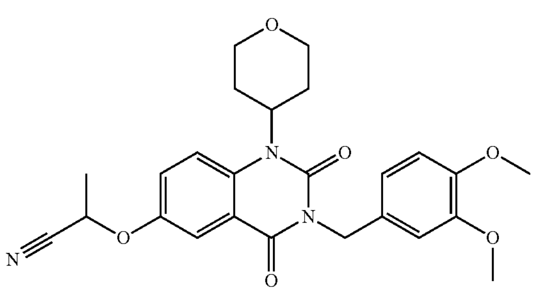 [SMILES: COc1ccc(Cn2c(=O)c3cc(OC(C)C#N)ccc3n(C3CCOCC3)c2=O)cc1OC] | 2-{[3-(3,4-dimethoxybenzyl)-2,4-dioxo-1-(tetrahydro-2H-pyran-4-yl)-1,2,3,4-tetrahydro-quinazolin-6-yl]oxy}propanenitrilemethane (1:1) (enantiomer 2) | 1H NMR (600 MHz, DMSO-$d_6$) δ ppm 1.64 (d, 2 H) 1.70 (d, 3 H) 2.67 (qd, 2 H) 3.51 (t, 2 H) 3.69 (s, 3 H) 3.70 (s, 3 H) 3.94 (dd, 2 H) 4.72 (br. t, 1 H) 5.04 (s, 2 H) 5.58 (q, 1 H) 6.83 (d, 1 H) 6.85 (d, 1 H) 6.99 (s, 1 H) 7.49 (dd, 1 H) 7.73 (d, 1 H) 7.81 (d, 1 H) | 466 |

TABLE 1-continued

| Compound No. | STRUCTURE | NOMENCLATURE | NMR | MASS |
|---|---|---|---|---|
| 21 | 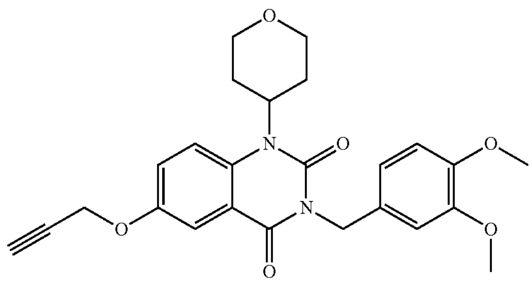 [SMILES: C#CCOc1ccc2c(c1)c(=O)n(Cc1ccc(OC)c(OC)c1)c(=O)n2C1CCOCC1] | 3-(3,4-dimethoxybenzyl)-6-(prop-2-yn-1-yloxy)-1-(tetrahydro-2H-pyran-4-yl)quinazoline-2,4(1H,3H)-dione | 1H NMR (600 MHz, DMSO-d6) δ ppm 1.63 (d, 2 H) 2.67 (qd, 2 H) 3.51 (t, 2 H) 3.57 (br. s, 1 H) 3.69 (s, 3 H) 3.70 (s, 3 H) 3.94 (dd, 2 H) 4.71 (br. t., 1 H) 4.88 (s, 2 H) 5.04 (s, 2 H) 6.82 (d, 1 H) 6.85 (d, 1 H) 6.99 (s, 1 H) 7.40 (dd, 1 H) 7.62 (d, 1 H) 7.75 (d, 1 H) | 451 |
| 22 | 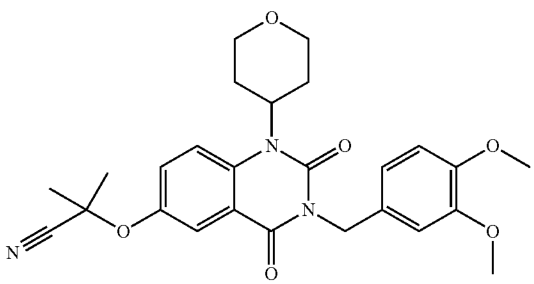 [SMILES: COc1ccc(Cn2c(=O)c3cc(OC(C)(C)C#N)ccc3n(C3CCOCC3)c2=O)cc1OC] | 2-{[3-(3,4-dimethoxybenzyl)-2,4-dioxo-1-(tetrahydro-2H-pyran-4-yl)-1,2,3,4-tetrahydro-quinazolin-6-yl]oxy}-2-methylpropanenitrile | 1H NMR (600 MHz, DMSO-d$_6$) δ ppm 1.66 (d, 2 H) 1.70 (s, 6 H) 2.68 (qd, 2 H) 3.51 (t, 2 H) 3.70 (s, 3 H) 3.71 (s, 3 H) 3.95 (dd, 2 H) 4.73 (t, 1 H) 5.03 (s, 2 H) 6.84 (d, 1 H) 6.86 (d, 1 H) 6.99 (s, 1 H) 7.55 (dd, 1 H) 7.82 (d, 1 H) 7.83 (s, 1 H) | 480 |
| 23 | 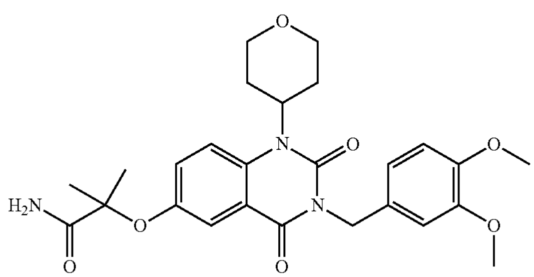 [SMILES: COc1ccc(Cn2c(=O)c3cc(OC(C)(C)C(N)=O)ccc3n(C3CCOCC3)c2=O)cc1OC] | 2-{[3-(3,4-dimethoxybenzyl)-2,4-dioxo-1-(tetrahydro-2H-pyran-4-yl)-1,2,3,4-tetrahydro-quinazolin-6-yl]oxy}-2-methylpropanamide | 1H NMR (600 MHz, DMSO-d$_6$) δ ppm 1.43 (s, 6 H) 1.63 (d, 2 H) 2.67 (qd, 2 H) 3.50 (t, 2 H) 3.69 (s, 3 H) 3.70 (s, 3 H) 3.94 (dd, 2 H) 4.70 (br. t., 1 H) 5.02 (s, 2 H) 6.82 (d, 1 H) 6.85 (d, 1 H) 6.98 (s, 1 H) 7.27 (s, 1 H) 7.33 (dd, 1 H) 7.55 (d, 1 H) 7.56 (s, 1 H) 7.72 (d, 1 H) | 498 |
| 24 | 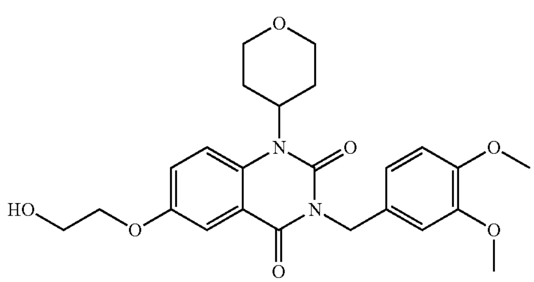 [SMILES: COc1ccc(Cn2c(=O)c3cc(OCCO)ccc3n(C3CCOCC3)c2=O)cc1OC] | 3-(3,4-dimethoxybenzyl)-6-(2-hydroxyethoxy)-1-(tetrahydro-2H-pyran-4-yl)quinazoline-2,4(1H,3H)-dione | 1H NMR (600 MHz, DMSO-d$_6$) δ ppm 1.63 (d, 2 H) 2.68 (qd, 2 H) 3.51 (t, 2 H) 3.70 (s, 3 H) 3.70 (s, 3 H) 3.72 (dt, 2 H) 3.94 (dd, 2 H) 4.05 (t, 2 H) 4.71 (br. t., 1 H) 4.86 (t, 1 H) 5.04 (s, 2 H) 6.82 (d, 1 H) 6.85 (d, 1 H) 6.99 (s, 1 H) 7.37 (dd, 1 H) 7.52 (d, 1 H) 7.72 (d, 1 H) | 457 |
| 25 | 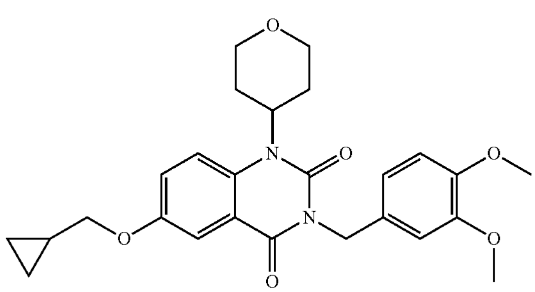 [SMILES: COc1ccc(Cn2c(=O)c3cc(OCC4CC4)ccc3n(C3CCOCC3)c2=O)cc1OC] | 6-(cyclopropylmethoxy)-3-(3,4-dimethoxybenzyl)-1-(tetrahydro-2H-pyran-4-yl)quinazoline-2,4(1H,3H)-dione | 1H NMR (600 MHz, DMSO-d$_6$) δ ppm 0.32-0.35 (m, 2 H) 0.55-0.58 (m, 2 H) 1.19-1.24 (m, 1 H) 1.62 (d, 2 H) 2.67 (qd, 2 H) 3.51 (t, 2 H) 3.69 (s, 3 H) 3.70 (s, 3 H) 3.88 (d, 2 H) 3.94 (dd, 2 H) 4.71 (t, 1 H) 5.04 (s, 2 H) 6.82 (d, 1 H) 6.85 (d, 1 H) 6.98 (s, 1 H) 7.37 (dd, 1 H) 7.49 (d, 1 H) 7.71 (d, 1 H) | 467 |

TABLE 1-continued

| Compound No. | STRUCTURE | NOMENCLATURE | NMR | MASS |
|---|---|---|---|---|
| 26 | 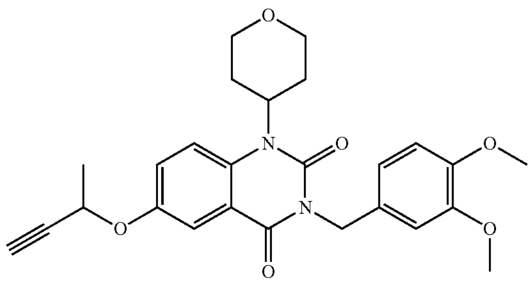 [SMILES: C#CC(C)Oc1ccc2c(c1)c(=O)n(Cc1ccc(OC)c(OC)c1)c(=O)n2C1CCOCC1] | 3-(3,4-dimethoxybenzyl)-6-[(1-methylprop-2-yn-1-yl)oxy]-1-(tetrahydro-2H-pyran-4-yl)quinazoline-2,4(1H,3H)-dione | 1H NMR (500 MHz, DMSO-$d_6$) δ ppm 1.70 (d, 3 H) 1.77 (d, 2 H) 2.81 (qd, 2 H) 3.64 (t, 2 H) 3.68 (d, 1 H) 3.83 (s, 3 H) 3.84 (s, 3 H) 4.08 (dd, 2 H) 4.85 (t, 1 H) 5.15 (d, 1 H) 5.19 (d, 1 H) 5.31 (qd, 1 H) 6.96 (dd, 1 H) 6.99 (d, 1 H) 7.12 (d, 1 H) 7.54 (dd, 1 H) 7.79 (d, 1 H) 7.88 (d, 1 H) | 465 |
| 27 | 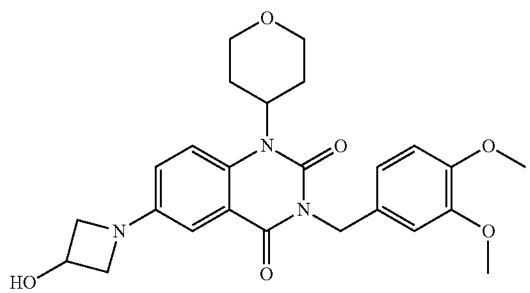 [SMILES: COc1ccc(Cn2c(=O)c3cc(N4CC(O)C4)ccc3n(C3CCOCC3)c2=O)cc1OC] | 3-(3,4-dimethoxybenzyl)-6-(3-hydroxyazetidin-1-yl)-1-(tetrahydro-2H-pyran-4-yl)quinazoline-2,4(1H,3H)-dione | 1H NMR (600 MHz, DMSO-$d_6$) δ ppm 1.60 (d, 2 H) 2.67 (qd, 2 H) 3.51 (m, 4 H) 3.69 (s, 3 H) 3.70 (s, 3 H) 3.94 (dd, 2 H) 4.11 (t, 2 H) 4.56 (tt, 1 H) 4.67 (br. t, 1 H) 5.03 (s, 2 H) 5.61 (d, 1 H) 6.81 (d, 1 H) 6.85 (d, 1 H) 6.90 (dd, 1 H) 6.98 (s, 1 H) 7.01 (d, 1 H) 7.61 (d, 1 H) | 468 |
| 28 | 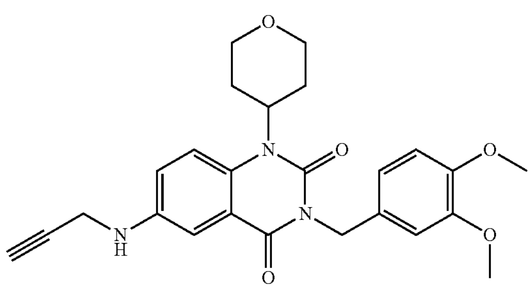 [SMILES: C#CCNc1ccc2c(c1)c(=O)n(Cc1ccc(OC)c(OC)c1)c(=O)n2C1CCOCC1] | 3-(3,4-dimethoxybenzyl)-6-(prop-2-yn-1-ylamino)-1-(tetrahydro-2H-pyran-4-yl)quinazoline-2,4(1H,3H)-dione | 1H NMR (500 MHz, DMSO-$d_6$) δ ppm 1.61 (d, 2 H) 2.69 (qd, 2 H) 3.06 (t, 1 H) 3.51 (t, 2 H) 3.70 (s, 3 H) 3.71 (s, 3 H) 3.92 (dd, 2 H) 3.95 (dd, 2 H) 4.61-4.74 (br. t, 1 H) 5.04 (s, 2 H) 6.26 (t, 1 H) 6.82 (dd, 1 H) 6.86 (d, 1 H) 6.99 (d, 1 H), 7.13 (dd, 1 H) 7.28 (d, 1 H) 7.59 (d, 1 H) | 450 |
| 29 | 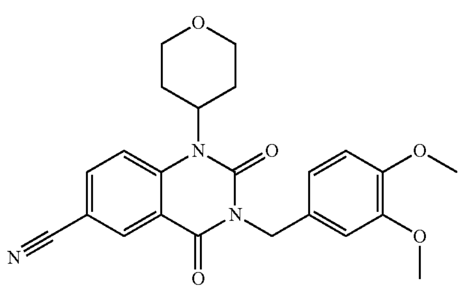 [SMILES: COc1ccc(Cn2c(=O)c3cc(C#N)ccc3n(C3CCOCC3)c2=O)cc1OC] | 3-(3,4-dimethoxybenzyl)-2,4-dioxo-1-(tetrahydro-2H-pyran-4-yl)-1,2,3,4-tetrahydroquinazoline-6-carbonitrile | 1H NMR (600 MHz, DMSO-$d_6$) δ ppm 1.67 (d, 2 H) 2.65 (qd, 2 H) 3.53 (t, 2 H) 3.71 (s, 3 H) 3.71 (s, 3 H) 3.95 (dd, 2 H) 4.78 (br. t, 1 H) 5.04 (s, 2 H) 6.86 (m, 2 H) 6.99 (s, 1 H) 7.97 (d, 1 H) 8.16 (dd, 1 H) 8.43 (d, 1 H) | 444 |
| 30 | 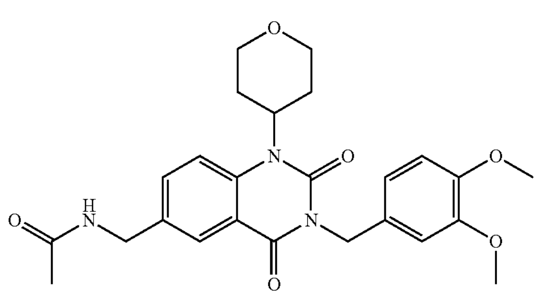 [SMILES: COc1ccc(Cn2c(=O)c3cc(CNC(C)=O)ccc3n(C3CCOCC3)c2=O)cc1OC] | N-{[3-(3,4-dimethoxybenzyl)-2,4-dioxo-1-(tetrahydro-2H-pyran-4-yl)-1,2,3,4-tetrahydroquinazolin-6-yl]methyl}acetamide | 1H NMR (500 MHz, DMSO-$d_6$) δ ppm 1.63 (d, 2 H) 1.86 (s, 3 H) 2.68 (qd, 2 H) 3.52 (t, 2 H) 3.70 (s, 3 H) 3.71 (s, 3 H) 3.96 (dd, 2 H) 4.29 (d, 2 H) 4.74 (br t, 1 H) 5.05 (s, 2 H) 6.81 (d, 1 H) 6.86 (d, 1 H) 6.98 (s, 1 H) 7.64 (d, 1 H) 7.74 (d, 1 H) 7.96 (s, 1 H) 8.43 (t, 1 H) | 468 |

TABLE 1-continued

| Compound No. | STRUCTURE | NOMENCLATURE | NMR | MASS |
|---|---|---|---|---|
| 31 | 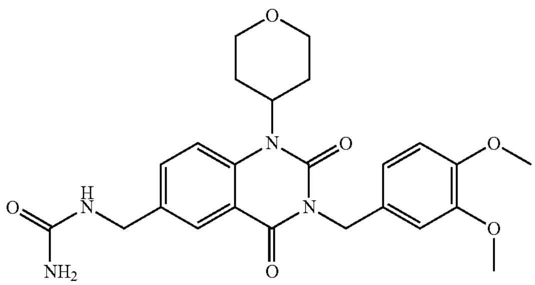 [SMILES: COc1ccc(Cn2c(=O)c3cc(CNC(N)=O)ccc3n(C3CCOCC3)c2=O)cc1OC] | 1-{[3-(3,4-dimethoxybenzyl)-2,4-dioxo-1-(tetrahydro-2H-pyran-4-yl)-1,2,3,4-tetrahydro-quinazolin-6-yl]methyl}urea | 1H NMR (500 MHz, DMSO-$d_6$) δ ppm 1.63 (d, 2 H) 2.68 (qd, 2 H) 3.52 (t, 2 H) 3.70 (s, 3 H) 3.71 (s, 3 H) 3.96 (dd, 2 H) 4.22 (d, 2 H) 4.74 (br. t, 1 H) 5.05 (s, 2 H) 5.56 (s, 2 H) 6.52 (t, 1 H) 6.82 (dd, 1 H) 6.86 (d, 1 H) 6.99 (d, 1 H) 7.64 (dd, 1 H) 7.73 (d, 1 H) 7.97 (d, 1 H) | 469 |
| 32 | 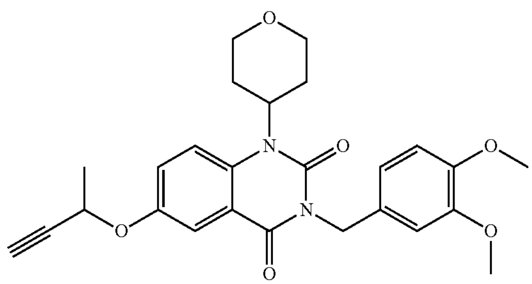 [SMILES: C#CC(C)Oc1ccc2c(c1)c(=O)n(Cc1ccc(OC)c(OC)c1)c(=O)n2C1CCOCC1] | 3-(3,4-dimethoxybenzyl)-6-[(1-methylprop-2-yn-1-yl)oxy]-1-(tetrahydro-2H-pyran-4-yl)quinazoline-2,4(1H,3H)-dione (enantiomer 1) | 1H NMR (500 MHz, DMSO-$d_6$) δ ppm 1.57 (d, 3 H) 1.64 (d, 2 H) 2.68 (qd, 2 H) 3.52 (t, 2 H) 3.55 (d, 1 H) 3.70 (s, 3 H) 3.71 (s, 3 H) 3.95 (dd, 2 H) 4.72 (br. t, 1 H) 5.02 (d, 1 H) 5.05 (d, 1 H) 5.18 (qd, 1 H) 6.83 (dd, 1 H) 6.86 (d, 1 H) 6.99 (d, 1 H) 7.41 (dd, 1 H) 7.66 (d, 1 H) 7.75 (d, 1 H) | 465 |
| 33 | 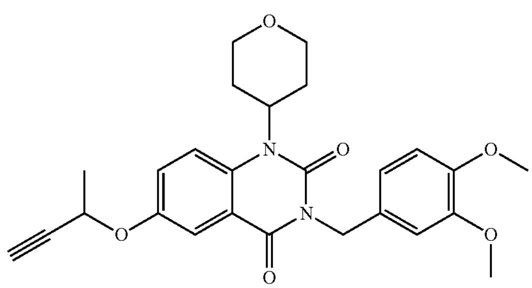 [SMILES: C#CC(C)Oc1ccc2c(c1)c(=O)n(Cc1ccc(OC)c(OC)c1)c(=O)n2C1CCOCC1] | 3-(3,4-dimethoxybenzyl)-6-[(1-methylprop-2-yn-1-yl)oxy]-1-(tetrahydro-2H-pyran-4-yl)quinazoline-2,4(1H,3H)-dione (enantiomer 2) | 1H NMR (500 MHz, DMSO-$d_6$) δ ppm 1.57 (d, 3 H) 1.64 (d, 2 H) 2.68 (qd, 2 H) 3.52 (t, 2 H) 3.55 (d, 1 H) 3.70 (s, 3 H) 3.71 (s, 3 H) 3.95 (dd, 2 H) 4.72 (br. t, 1 H) 5.02 (d, 1 H) 5.05 (d, 1 H) 5.18 (qd, 1 H) 6.83 (dd, 1 H) 6.86 (d, 1 H) 6.99 (d, 1 H) 7.41 (dd, 1 H) 7.66 (d, 1 H) 7.75 (d, 1 H) | 465 |
| 34 | 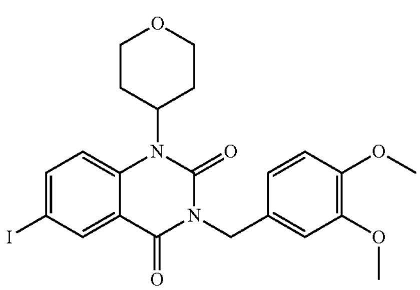 [SMILES: COc1ccc(Cn2c(=O)c3cc(I)ccc3n(C3CCOCC3)c2=O)cc1OC] | 3-(3,4-dimethoxybenzyl)-6-iodo-1-(tetrahydro-2H-pyran-4-yl)quinazoline-2,4(1H,3H)-dione | 1H NMR (500 MHz, DMSO-$d_6$) δ ppm 1.64 (d, 2 H) 2.65 (dq, 2 H) 3.51 (t, 2 H) 3.70 (s, 3 H) 3.71 (s, 3 H) 3.95 (dd, 2 H) 4.71 (br. t, 1 H) 5.03 (s, 2 H) 6.83 (d, 1 H) 6.86 (d, 1 H) 6.98 (s, 1 H) 7.62 (dd, 1 H) 8.03 (d, 1 H) 8.30 (d, 1 H) | 523 |
| 35 | 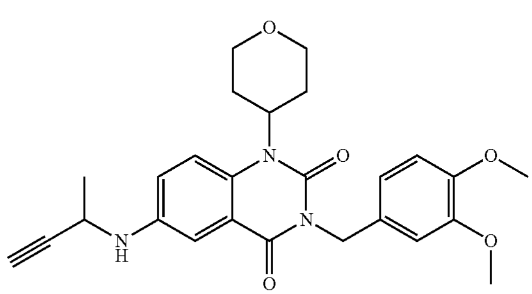 [SMILES: C#CC(C)Nc1ccc2c(c1)c(=O)n(Cc1ccc(OC)c(OC)c1)c(=O)n2C1CCOCC1] | 3-(3,4-dimethoxybenzyl)-6-[(1-methylprop-2-yn-1-yl)amino]-1-(tetrahydro-2H-pyran-4-yl)-quinazoline-2,4(1H,3H)-dione | 1H NMR (500 MHz, DMSO-$d_6$) δ ppm 1.43 (d, 3 H) 1.61 (d, 2 H) 2.69 (dq, 2 H) 3.06 (d, 1 H) 3.50 (t, 2 H) 3.70 (s, 3 H) 3.71 (s, 3 H) 3.95 (dd, 2 H) 4.18-4.27 (m, 1 H) 4.66 (br. t, 1 H) 4.99-5.08 (m, 2 H) 6.11 (d, 1 H) 6.82 (dd, 1 H) 6.86 (d, 1 H) 6.99 (d, 1 H) 7.15 (dd, 1 H) 7.32 (d, 1 H) 7.59 (d, 1 H) | 464 |

TABLE 1-continued

| Compound No. | STRUCTURE | NOMENCLATURE | NMR | MASS |
|---|---|---|---|---|
| 36 | 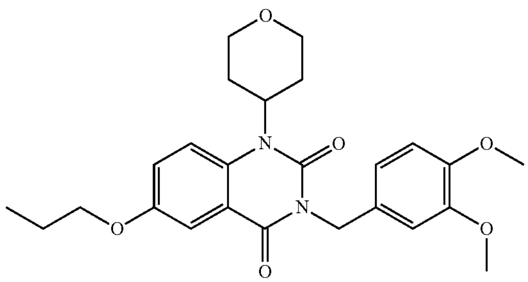 [SMILES: CCCOc1ccc2c(c1)c(=O)n(Cc1ccc(OC)c(OC)c1)c(=O)n2C1CCOCC1] | 3-(3,4-dimethoxybenzyl)-6-propoxy-1-(tetrahydro-2H-pyran-4-yl)quinazoline-2,4(1H,3H)-dione | 1H NMR (500 MHz, DMSO-d$_6$) δ ppm 0.98 (t, 3 H) 1.63 (d, 2 H) 1.74 (m, 2 H) 2.68 (qd, 2 H) 3.52 (t, 2 H) 3.70 (s, 3 H) 3.71 (s, 3 H) 3.95 (dd, 2 H) 3.99 (t, 2 H) 4.72 (br. s., 1 H) 5.05 (s, 2 H) 6.84 (d, 1 H) 6.86 (d, 1 H) 6.99 (d, 1 H) 7.36 (dd, 1 H) 7.51 (d, 1 H) 7.73 (d, 1 H) | 455 |
| 37 | 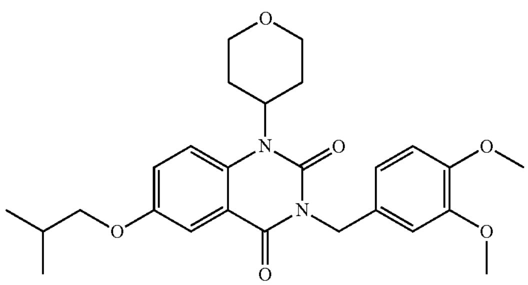 [SMILES: COc1ccc(Cn2c(=O)c3cc(OCC(C)C)ccc3n(C3CCOCC3)c2=O)cc1OC] | 3-(3,4-dimethoxybenzyl)-6-(2-methylpropoxy)-1-(tetrahydro-2H-pyran-4-yl)quinazoline-2,4(1H,3H)-dione | 1H NMR (500 MHz, DMSO-d$_6$) δ ppm 0.99 (d, 6H) 1.63 (d, 2 H) 2.03 (dt, 1 H) 2.68 (qd, 2 H) 3.52 (t, 2 H) 3.70 (s, 3 H) 3.71 (s, 3 H) 3.81 (d, 2 H) 3.95 (dd, 2 H) 4.72 (br. s., 1 H) 5.05 (s, 2 H) 6.83 (dd, 3 H) 6.86 (d, 1 H) 6.99 (d, 1 H) 7.37 (dd, 1 H) 7.51 (d, 1 H) 7.73 (d, 1 H) | 469 |
| 38 | 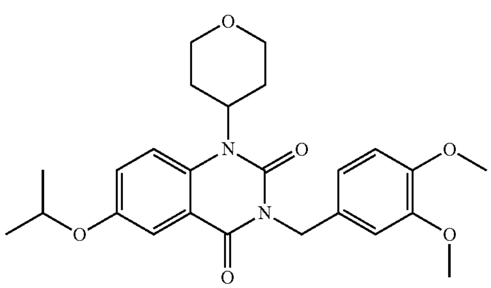 [SMILES: COc1ccc(Cn2c(=O)c3cc(OC(C)C)ccc3n(C3CCOCC3)c2=O)cc1OC] | 3-(3,4-dimethoxybenzyl)-6-(1-methylethoxy)-1-(tetrahydro-2H-pyran-4-yl)quinazoline-2,4(1H,3H)-dione | 1H NMR (500 MHz, DMSO-d$_6$) δ ppm 1.28 (d, 6 H) 1.63 (d, 2 H) 2.68 (qd, 2 H) 3.51 (t, 2 H) 3.70 (s, 3 H) 3.71 (s, 3 H) 3.95 (dd, 2 H) 4.64-4.69 (m, 1 H) 4.72 (br. s., 1 H) 5.04 (s, 2 H) 6.82-6.84 (dd, 1 H) 6.85-6.87 (d, 1 H) 6.99 (d, 1 H) 7.34 (dd, 1 H) 7.50 (d, 1 H) 7.72 (d, 1 H) | 455 |
| 39 | 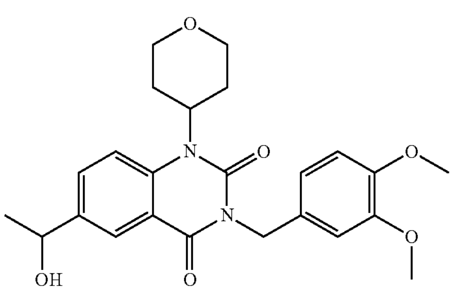 [SMILES: COc1ccc(Cn2c(=O)c3cc(C(C)O)ccc3n(C3CCOCC3)c2=O)cc1OC] | 3-(3,4-dimethoxybenzyl)-6-(1-hydroxyethyl)-1-(tetrahydro-2H-pyran-4-yl)quinazoline-2,4(1H,3H)-dione | 1H NMR (500 MHz, DMSO-d$_6$) δ ppm 1.33 (d, 3 H) 1.64 (d, 2 H) 2.69 (qd, 2 H) 3.52 (t, 2 H) 3.70 (s, 3 H) 3.71 (s, 3 H) 3.96 (dd, 2 H) 4.75 (br. s., 1 H) 4.80 (m, 1 H) 5.05 (s, 2 H) 5.31 (d, 1 H) 6.82 (dd, 1 H) 6.86 (d, 1 H) 6.99 (d, 1 H) 7.70-7.75 (m, 2 H) 8.06 (s, 1 H) | 441 |
| 40 | 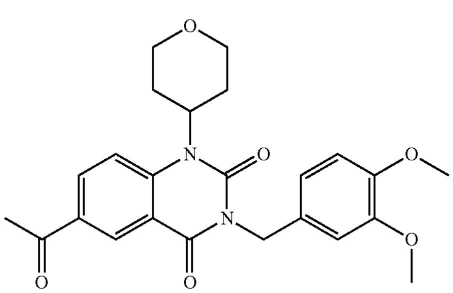 [SMILES: COc1ccc(Cn2c(=O)c3cc(C(C)=O)ccc3n(C3CCOCC3)c2=O)cc1OC] | 6-acetyl-3-(3,4-dimethoxybenzyl)-1-(tetrahydro-2H-pyran-4-yl)quinazoline-2,4(1H,3H)-dione | 1H NMR (500 MHz, DMSO-d$_6$) δ ppm 1.68 (d, 2 H) 2.63 (s, 3 H) 2.67 (dq, 2 H) 3.54 (t, 2 H) 3.70 (s, 3 H) 3.72 (s, 3 H) 3.96 (dd, 2 H) 4.82 (t, 1 H) 5.06 (s, 2 H) 6.85-6.88 (m, 2 H) 7.00 (s, 1 H) 7.90 (d, 1 H) 8.24 (dd, 1 H) 8.60 (d, 1 H) | 439 |

TABLE 1-continued

| Compound No. | STRUCTURE | NOMENCLATURE | NMR | MASS |
|---|---|---|---|---|
| 41 | 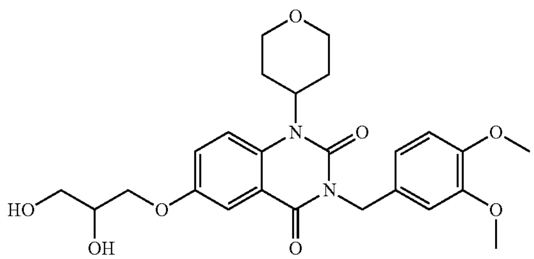 [SMILES: COc1ccc(Cn2c(=O)c3cc(OCC(O)CO)ccc3n(C3CCOCC3)c2=O)cc1OC] | 6-(2,3-dihydroxypropoxy)-3-(3,4-dimethoxybenzyl)-1-(tetrahydro-2H-pyran-4-yl)-quinazoline-2,4(1H,3H)-dione | 1H NMR (500 MHz, DMSO-$d_6$) δ ppm 1.66 (d, 2 H) 2.71 (dq, 2 H) 3.47 (t, 2 H) 3.54 (t, 2 H) 3.73 (br. s., 3 H) 3.73 (br. s., 3 H) 3.82 (br. m., 1 H) 3.89-4.02 (m, 3 H) 4.10 (dd, 1 H) 4.71 (br. s, 1 H) 4.75 (br. s, 1 H) 5.00 (d, 1 H) 5.07 (s, 2 H) 6.75-6.93 (m, 2 H) 7.02 (d, 1 H) 7.40 (dd, 1 H) 7.56 (d, 1 H) 7.76 (d, 1 H) | 487 |
| 42 | 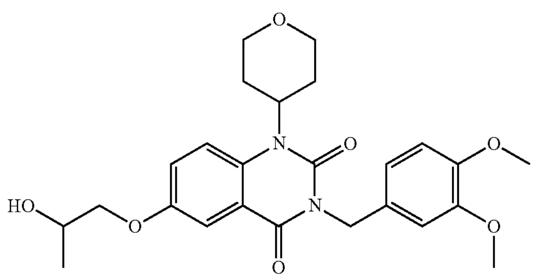 [SMILES: COc1ccc(Cn2c(=O)c3cc(OCC(C)O)ccc3n(C3CCOCC3)c2=O)cc1OC] | 3-(3,4-dimethoxybenzyl)-6-(2-hydroxypropoxy)-1-(tetrahydro-2H-pyran-4-yl)quinazoline-2,4(1H,3H)-dione | 1H NMR (500 MHz, DMSO-$d_6$) δ ppm 1.15 (d, 3 H) 1.63 (d, 2 H) 2.68 (dq, 2 H) 3.52 (t, 2 H) 3.70 (s, 3 H) 3.71 (s, 3 H) 3.87 (d, 2 H) 3.94-3.96 (m, 3 H) 4.72 (br. s., 1 H) 4.89 (d, 1 H) 5.05 (s, 2 H) 6.83 (dd, 1 H) 6.86 (d, 1 H) 6.99 (d, 1 H) 7.38 (dd, 1 H) 7.52 (d, 1 H) 7.73 (d, 1 H) | 471 |
| 43 | 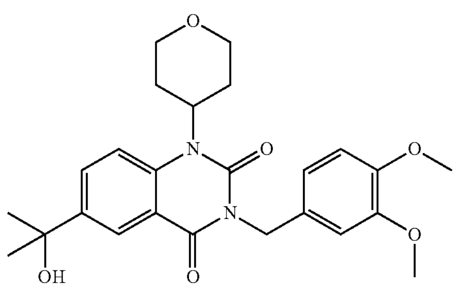 [SMILES: COc1ccc(Cn2c(=O)c3cc(C(C)(C)O)ccc3n(C3CCOCC3)c2=O)cc1OC] | 3-(3,4-dimethoxybenzyl)-6-(1-hydroxy-1-methylethyl)-1-(tetrahydro-2H-pyran-4-yl)-quinazoline-2,4(1H,3H)-dione | 1H NMR (500 MHz, DMSO-$d_6$) δ ppm 1.49 (s, 6 H) 1.69 (d, 2 H) 2.70 (dq, 2 H) 3.57 (t, 2 H) 3.70 (s, 3 H) 3.71 (s, 3 H) 4.01 (dd, 2 H) 4.80 (br. s., 1 H) 5.05 (s, 2 H) 5.25 (s, 1 H) 6.87 (dd, 1 H) 6.89 (d, 1 H) 7.04 (d, 1 H) 7.75 (d, 1 H) 7.88 (dd, 1 H) 8.21 (d, 1 H) | 455 |
| 44 | 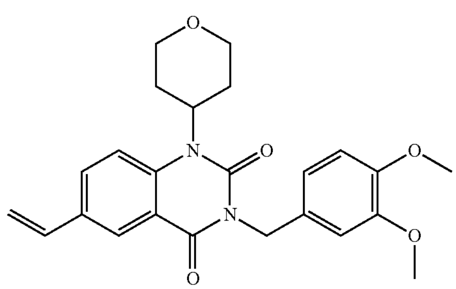 [SMILES: C=Cc1ccc2c(c1)c(=O)n(Cc1ccc(OC)c(OC)c1)c(=O)n2C1CCOCC1] | 3-(3,4-dimethoxybenzyl)-6-ethenyl-1-(tetrahydro-2H-pyran-4-yl)quinazoline-2,4(1H,3H)-dione | 1H NMR (500 MHz, DMSO-$d_6$) δ ppm 1.65 (d, 2 H) 2.68 (dq, 2 H) 3.53 (t, 2 H) 3.70 (s, 3 H) 3.71 (s, 3 H) 3.96 (dd, 2 H) 4.76 (br. t., 1 H) 5.05 (s, 2 H) 5.31 (d, 1 H) 5.89 (d, 1 H) 6.80-6.87 (m, 3 H) 7.00 (d, 1 H) 7.77 (d, 1 H) 7.90 (dd, 1 H) 8.11 (d, 1 H) | 423 |
| 45 | 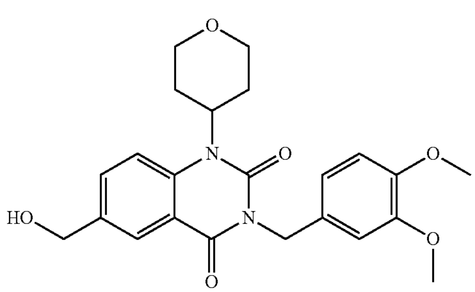 [SMILES: COc1ccc(Cn2c(=O)c3cc(CO)ccc3n(C3CCOCC3)c2=O)cc1OC] | 3-(3,4-dimethoxybenzyl)-6-(hydroxymethyl)-1-(tetrahydro-2H-pyran-4-yl)quinazoline-2,4(1H,3H)-dione | 1H NMR (500 MHz, DMSO-$d_6$) δ ppm 1.65 (d, 2 H) 2.68 (dq, 2 H) 3.58 (t, 2 H) 3.70 (s, 3 H) 3.71 (s, 3 H) 4.01 (dd, 2 H) 4.59 (d., 2 H) 4.79 (br. t., 1 H) 5.09 (s, 2 H) 5.35 (t, 1 H) 6.87 (m, 2 H) 7.03 (s, 1 H) 7.72 (d, 1 H) 7.78 (d, 1 H) 8.08 (s, 1 H) | 427 |

TABLE 1-continued

| Compound No. | STRUCTURE | NOMENCLATURE | NMR | MASS |
|---|---|---|---|---|
| 46 | 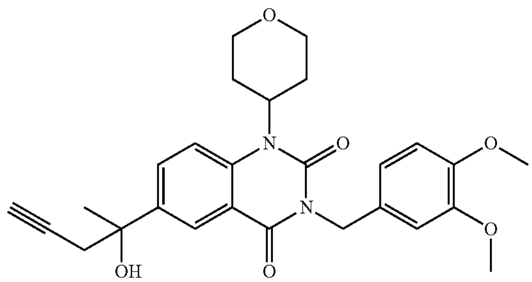 [SMILES: C#CCC(C)(O)c1ccc2c(c1)c(=O)n(Cc1ccc(OC)c(OC)c1)c(=O)n2C1CCOCC1] | 3-(3,4-dimethoxybenzyl)-6-(1-hydroxy-1-methylbut-3-yn-1-yl)-1-(tetrahydro-2H-pyran-4-yl)quinazoline-2,4(1H,3H)-dione | 1H NMR (500 MHz, DMSO-$d_6$) δ ppm 1.50 (s, 3 H) 1.62 (d, 2 H) 2.57 (t, 2 H) 2.66 (m, 2 H) 2.69 (m, 1 H) 3.49 (t, 2 H) 3.67 (s, 3 H) 3.68 (s, 3 H) 3.92 (dd, 2 H) 4.72 (br. s., 1 H) 5.02 (s, 2 H) 5.44 (s, 1 H) 6.78-6.81 (dd, 1 H) 6.81-6.84 (d, 1 H) 6.96 (d, 1 H) 7.69 (d, 1 H) 7.83 (dd, 1 H) 8.17 (d, 1 H) | 479 |
| 47 | 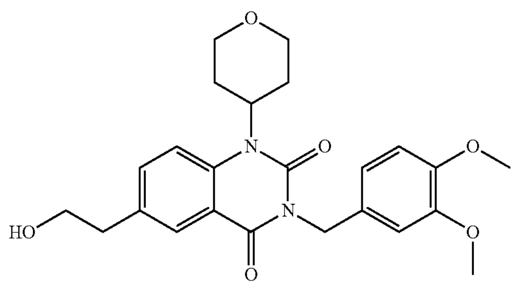 [SMILES: COc1ccc(Cn2c(=O)c3cc(CCO)ccc3n(C3CCOCC3)c2=O)cc1OC] | 3-(3,4-dimethoxybenzyl)-6-(2-hydroxyethyl)-1-(tetrahydro-2H-pyran-4-yl)quinazoline-2,4(1H,3H)-dione | 1H NMR (500 MHz, DMSO-$d_6$) δ ppm 1.61 (d, 2 H) 2.67 (qd, 2 H) 2.77 (t, 2 H) 3.50 (t, 2 H) 3.60 (dt, 2 H) 3.68 (s, 3 H) 3.69 (s, 3 H) 3.94 (dd, 2 H) 4.62 (t, 1 H) 4.72 (br. t, 1 H) 5.03 (s, 2 H) 6.80 (dd, 1 H) 6.84 (d, 1 H) 6.97 (d, 1 H) 7.62 (dd, 1 H) 7.67 (d, 1 H) 7.91 (d, 1 H) | 441 |
| 48 | 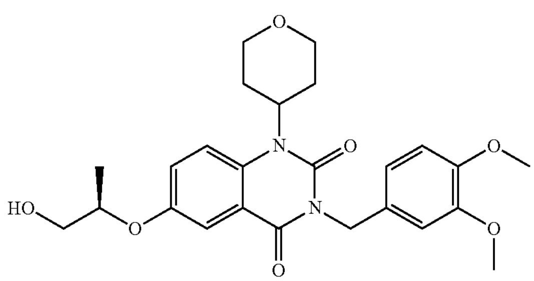 [SMILES: COc1ccc(Cn2c(=O)c3cc(O[C@H](C)CO)ccc3n(C3CCOCC3)c2=O)cc1OC] | 3-(3,4-dimethoxybenzyl)-6-[(1R)-2-hydroxy-1-methylethoxy]-1-(tetrahydro-2H-pyran-4-yl)-quinazoline-2,4(1H,3H)-dione | 1H NMR (500 MHz, DMSO-$d_6$) δ ppm 1.22 (d, 3 H) 1.64 (d, 2 H) 2.69 (qd, 2 H) 3.47-3.58 (m, 4 H) 3.71 (s, 3 H) 3.72 (s, 3 H) 3.96 (dd, 2 H) 4.47 (m, 1 H) 4.73 (t, 1 H) 4.89 (t, 1 H) 5.05 (s, 2 H) 6.84 (dd, 1 H) 6.87 (d, 1 H) 7.00 (d, 1 H) 7.38 (dd, 1 H) 7.56 (d, 1 H) 7.72 (d, 1 H) | 471 |
| 49 | 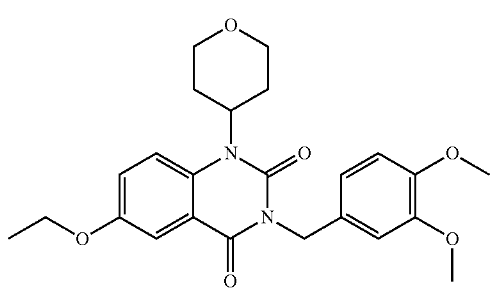 [SMILES: CCOc1ccc2c(c1)c(=O)n(Cc1ccc(OC)c(OC)c1)c(=O)n2C1CCOCC1] | 3-(3,4-dimethoxybenzyl)-6-ethoxy-1-(tetrahydro-2H-pyran-4-yl)quinazoline-2,4(1H,3H)-dione | 1H NMR (500 MHz, DMSO-$d_6$) δ ppm 1.34 (t, 3 H) 1.63 (d, 2 H) 2.68 (qd, 2 H) 3.51 (t, 2 H) 3.70 (s, 3 H) 3.71 (s, 3 H) 3.95 (dd, 2 H) 4.09 (q, 2 H) 4.72 (t, 1 H) 5.05 (s, 2 H) 6.82 (dd, 1 H) 6.86 (d, 1 H) 6.99 (d, 1 H) 7.36 (dd, 1 H) 7.50 (d, 1 H) 7.73 (d, 1 H) | 441 |
| 50 | 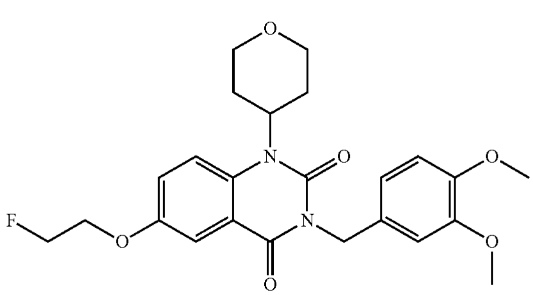 [SMILES: COc1ccc(Cn2c(=O)c3cc(OCCF)ccc3n(C3CCOCC3)c2=O)cc1OC] | 3-(3,4-dimethoxybenzyl)-6-(2-fluoroethoxy)-1-(tetrahydro-2H-pyran-4-yl)quinazoline-2,4(1H,3H)-dione | 1H NMR (500 MHz, DMSO-$d_6$) δ ppm 1.64 (d, 2 H) 2.68 (qd, 2 H) 3.52 (t, 2 H) 3.70 (s, 3 H) 3.71 (s, 3 H) 3.95 (dd, 2 H) 4.32 (dt, 2 H) 4.73 (br. t, 1 H) 4.75 (dt, 2 H) 5.05 (s, 2 H) 6.83 (dd, 1 H) 6.86 (d, 1 H) 7.00 (d, 1 H) 7.42 (dd, 1 H) 7.56 (d, 1 H) 7.76 (d, 1 H) | 459 |

TABLE 1-continued

| Compound No. | STRUCTURE | NOMENCLATURE | NMR | MASS |
|---|---|---|---|---|
| 51 | 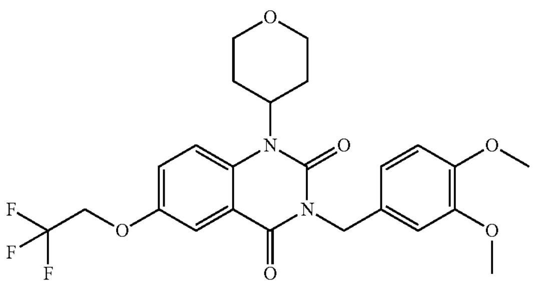 [SMILES: COc1ccc(Cn2c(=O)c3cc(OCC(F)(F)F)ccc3n(C3CCOCC3)c2=O)cc1OC] | 3-(3,4-dimethoxybenzyl)-1-(tetrahydro-2H-pyran-4-yl)-6-(2,2,2-trifluoroethoxy)quinazoline-2,4(1H,3H)-dione | 1H NMR (500 MHz, DMSO-$d_6$) δ ppm 1.70 (d, 2 H) 2.74 (qd, 2 H) 3.59 (t, 2 H) 3.77 (s, 3 H) 3.78 (s, 3 H) 4.01 (dd, 2 H) 4.80 (t, 1 H) 4.95 (q, 2 H) 5.12 (s, 2 H) 6.91 (dd, 1 H) 6.93 (d, 1 H) 7.06 (d, 1 H) 7.56 (dd, 1 H) 7.73 (d, 1 H) 7.86 (d, 1 H) | 495 |
| 52 | 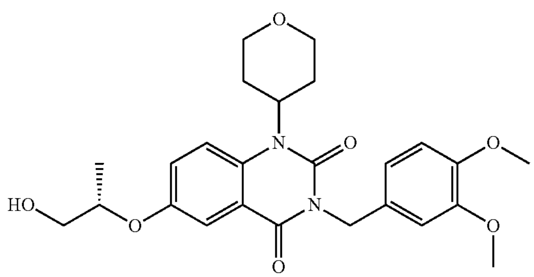 [SMILES: COc1ccc(Cn2c(=O)c3cc(O[C@@H](C)CO)ccc3n(C3CCOCC3)c2=O)cc1OC] | 3-(3,4-dimethoxybenzyl)-6-[(1S)-2-hydroxy-1-methylethoxy]-1-(tetrahydro-2H-pyran-4-yl)-quinazoline-2,4(1H,3H)-dione | 1H NMR (500 MHz, DMSO-$d_6$) δ ppm 1.21 (d, 3 H) 1.63 (d, 2 H) 2.68 (qd, 2 H) 3.46-3.57 (m, 4 H) 3.70 (s, 3 H) 3.71 (s, 3 H) 3.95 (dd, 2 H) 4.43-4.61 (m, 1 H) 4.72 (t, 1 H) 4.88 (t, 1 H) 5.05 (s, 2 H) 6.81-6.85 (m, 1 H) 6.85-6.87 (m, 1 H) 6.99 (s, 1 H) 7.37 (dd, 1 H) 7.55 (d, 1 H) 7.72 (d, 1 H) | 471 |
| 53 | 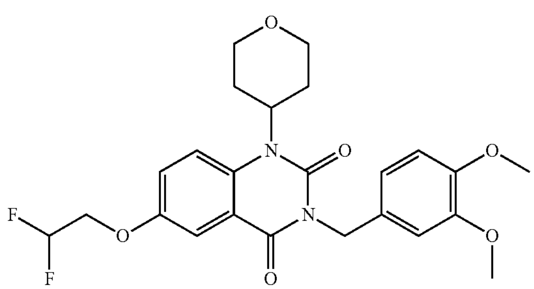 [SMILES: COc1ccc(Cn2c(=O)c3cc(OCC(F)F)ccc3n(C3CCOCC3)c2=O)cc1OC] | 6-(2,2-difluoroethoxy)-3-(3,4-dimethoxybenzyl)-1-(tetrahydro-2H-pyran-4-yl)quinazoline-2,4(1H,3H)-dione | 1H NMR (500 MHz, DMSO-$d_6$) δ ppm 1.64 (d, 2 H) 2.68 (qd, 2 H) 3.52 (t, 2 H) 3.70 (s, 3 H) 3.71 (s, 3 H) 3.95 (dd, 2 H) 4.42 (td, 2 H) 4.73 (t, 1 H) 5.05 (s, 2 H) 6.40 (tt, 1 H) 6.83 (dd, 1 H) 6.86 (d, 1 H) 7.00 (dd, 1 H) 7.45 (dd, 1 H) 7.60 (d, 1 H) 7.77 (d, 1 H) | 477 |
| 54 | 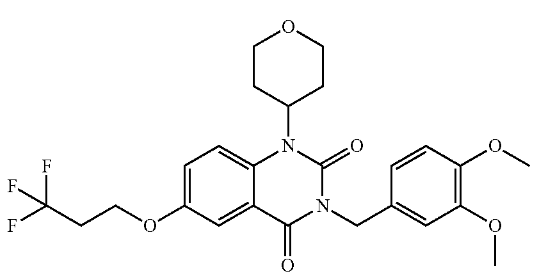 [SMILES: COc1ccc(Cn2c(=O)c3cc(OCCC(F)(F)F)ccc3n(C3CCOCC3)c2=O)cc1OC] | 3-(3,4-dimethoxybenzyl)-1-(tetrahydro-2H-pyran-4-yl)-6-(3,3,3-trifluoropropoxy)quinazoline-2,4(1H,3H)-dione | 1H NMR (500 MHz, DMSO-$d_6$) δ ppm 1.63 (d, 2 H) 2.68 (dq, 2 H) 2.80 (m, 2 H) 3.52 (t, 1 H) 3.70 (s, 3 H) 3.71 (s, 3 H) 3.95 (dd, 2 H) 4.29 (t, 2 H) 4.73 (t, 1 H) 5.05 (s, 2 H) 6.83 (dd, 1 H) 6.86 (d, 1 H) 7.00 (d, 1 H) 7.39 (dd, 1 H) 7.56 (d, 1 H) 7.75 (d, 1 H) | 509 |
| 55 | 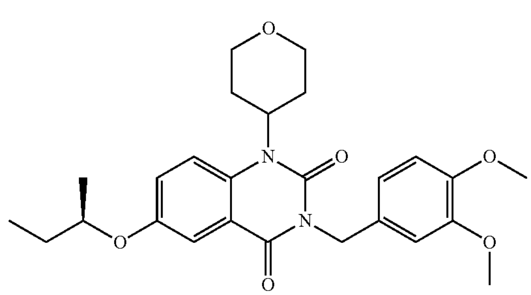 [SMILES: CC[C@@H](C)Oc1ccc2c(c1)c(=O)n(Cc1ccc(OC)c(OC)c1)c(=O)n2C1CCOCC1] | 3-(3,4-dimethoxybenzyl)-6-{[(1R)-1-methylpropyl]oxy}-1-(tetrahydro-2H-pyran-4-yl)-quinazoline-2,4(1H,3H)-dione | 1H NMR (500 MHz, DMSO-$d_6$) δ ppm 0.97 (t, 3 H) 1.28 (d, 3 H) 1.59-1.75 (m, 4 H) 2.72 (qd, 2 H) 3.55 (t, 2 H) 3.75 (s, 3 H) 3.75 (s, 3 H) 3.99 (dd, 2 H) 4.48 (m, 1 H) 4.76 (t, 1 H) 5.09 (s, 2 H) 6.87 (dd, 1 H) 6.91 (d, 1 H) 7.03 (d, 1 H) 7.39 (dd, 1 H) 7.54 (d, 1 H) 7.76 (d, 1 H) | 469 |

TABLE 1-continued

| Compound No. | STRUCTURE | NOMENCLATURE | NMR | MASS |
|---|---|---|---|---|
| 56 | 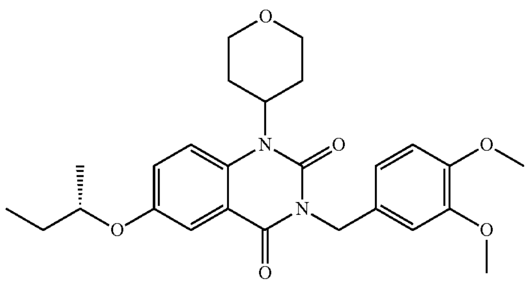 [SMILES: CC[C@H](C)Oc1ccc2c(c1)c(=O)n(Cc1ccc(OC)c(OC)c1)c(=O)n2C1CCOCC1] | 3-(3,4-dimethoxybenzyl)-6-{[(1S)-1-methylpropyl]oxy}-1-(tetrahydro-2H-pyran-4-yl)-quinazoline-2,4(1H,3H)-dione | 1H NMR (500 MHz, DMSO-$d_6$) δ ppm 0.92 (t, 3 H) 1.24 (d, 3 H) 1.51-1.75 (m, 4H) 2.68 (dq, 2 H) 3.51 (t, 2 H) 3.70 (s, 3 H) 3.71 (s, 3 H) 3.95 (dd, 2 H) 4.43 (m, 1 H) 4.72 (br. t, 1 H) 5.04 (s, 2 H) 6.83 (dd, 1 H) 6.86 (d, 1 H) 6.99 (d, 1 H) 7.35 (dd, 1 H) 7.50 (d, 1 H) 7.72 (d, 1 H) | 469 |
| 57 | 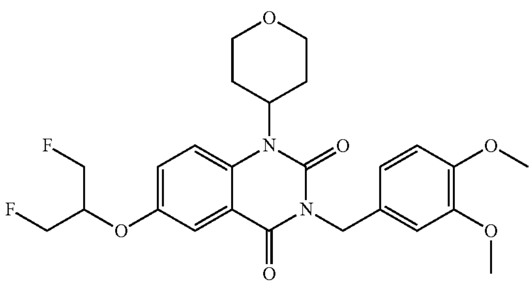 [SMILES: COc1ccc(Cn2c(=O)c3cc(OC(CF)CF)ccc3n(C3CCOCC3)c2=O)cc1OC] | 3-(3,4-dimethoxybenzyl)-6-[2-fluoro-1-(fluoromethyl)ethoxy]-1-(tetrahydro-2H-pyran-4-yl)quinazoline-2,4(1H,3H)-dione | 1H NMR (500 MHz, DMSO-$d_6$) δ ppm 1.64 (d, 2 H) 2.64-2.72 (m, 2 H) 3.52 (t, 2 H) 3.70 (s, 3 H) 3.71 (s, 3 H) 3.95 (dd, 2 H) 4.61-4.81 (m, 5 H) 5.01 (br. t, 1 H) 5.05 (s, 2 H) 6.83 (d, 1 H) 6.86 (d, 1 H) 6.99 (d, 1 H) 7.47 (dd, 1 H) 7.66 (d, 1 H) 7.76 (d, 1 H) | 491 |
| 58 | 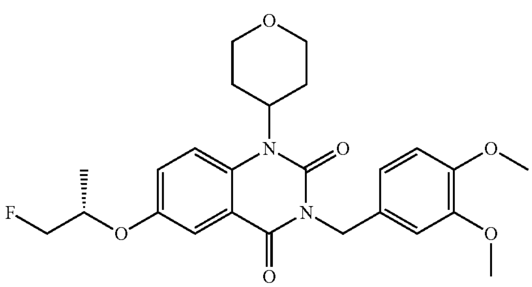 [SMILES: COc1ccc(Cn2c(=O)c3cc(O[C@@H](C)CF)ccc3n(C3CCOCC3)c2=O)cc1OC] | 3-(3,4-dimethoxybenzyl)-6-[(1S)-2-fluoro-1-methylethoxy]-1-(tetrahydro-2H-pyran-4-yl)-quinazoline-2,4(1H,3H)-dione | 1H NMR (600 MHz, DMSO-$d_6$) δ ppm 1.24 (d, 3 H) 1.63 (d, 2 H) 2.67 (qd, 2 H) 3.51 (t, 2 H) 3.69 (s, 3 H) 3.70 (s, 3 H) 3.94 (dd, 2 H) 4.54 (m, 2 H) 4.71 (br t, 1 H) 4.76-4.83 (m, 1 H) 5.04 (s, 2 H) 6.82 (d, 1 H) 6.85 (d, 1 H) 6.98 (s, 1 H) 7.39 (dd, 1 H) 7.56 (d, 1 H) 7.73 (d, 1 H) | 473 |
| 59 | 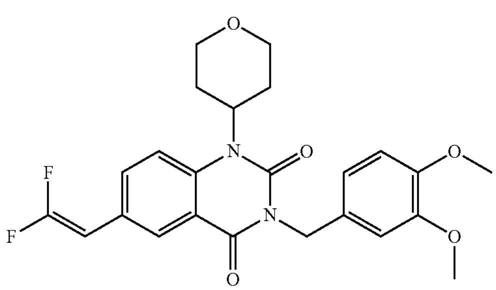 [SMILES: COc1ccc(Cn2c(=O)c3cc(C=C(F)F)ccc3n(C3CCOCC3)c2=O)cc1OC] | 6-(2,2-difluoroethenyl)-3-(3,4-dimethoxybenzyl)-1-(tetrahydro-2H-pyran-4-yl)quinazoline-2,4(1H,3H)-dione | 1H NMR (500 MHz, DMSO-$d_6$) δ ppm 1.65 (d, 2 H) 2.58-2.74 (m, 2 H) 3.52 (t, 2 H) 3.70 (br. s, 6 H) 3.96 (d, 2 H) 4.75 (br. s, 1 H) 5.05 (s, 2 H) 5.97 (dd, 1 H) 6.80-6.91 (m, 2 H) 6.99 (br. s, 1 H) 7.74 (d, 1 H) 7.82 (d, 1 H) 8.10 (br. s, 1 H) | 459 |
| 60 | 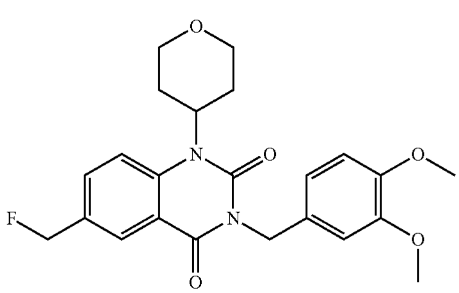 [SMILES: COc1ccc(Cn2c(=O)c3cc(CF)ccc3n(C3CCOCC3)c2=O)cc1OC] | 3-(3,4-dimethoxybenzyl)-6-(fluoromethyl)-1-(tetrahydro-2H-pyran-4-yl)quinazoline-2,4(1H,3H)-dione | 1H NMR (600 MHz, DMSO-$d_6$) δ ppm 1.67 (d, 2 H) 2.69 (qd, 2 H) 3.53 (t, 2 H) 3.70 (s, 3 H) 3.71 (s, 3 H) 3.96 (dd, 2 H) 4.78 (br. t, 1 H) 5.06 (s, 2 H) 5.49 (d, 1 H) 6.84 (d, 1 H) 6.86 (d, 1 H) 7.00 (s, 1 H) 7.80-7.85 (m, 2 H) 8.14 (s, 1 H) | 429 |

TABLE 1-continued

| Compound No. | STRUCTURE | NOMENCLATURE | NMR | MASS |
|---|---|---|---|---|
| 61 | 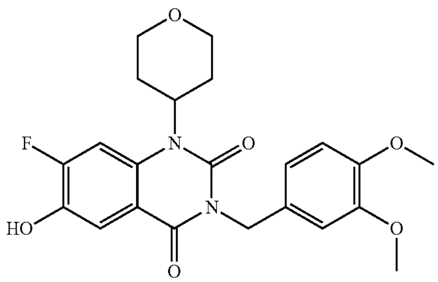 [SMILES: COc1ccc(Cn2c(=O)c3cc(O)c(F)cc3n(C3CCOCC3)c2=O)cc1OC] | 3-(3,4-dimethoxybenzyl)-7-fluoro-6-hydroxy-1-(tetrahydro-2H-pyran-4-yl)quinazoline-2,4(1H,3H)-dione | 1H NMR (600 MHz, DMSO-d$_6$) δ ppm 1.61 (d, 2 H) 2.68 (qd, 2 H) 3.55 (t, 2 H) 3.70 (s, 3 H) 3.71 (s, 3 H) 3.93 (dd, 2 H) 4.57 (br. t, 1 H) 5.03 (s, 2 H) 6.82 (dd, 1 H) 6.87 (d, 1 H) 6.98 (s, 1 H) 7.61 (d, 1 H) 7.74 (d, 1 H) 10.40 (br. s, 1 H) | 431 |
| 62 | 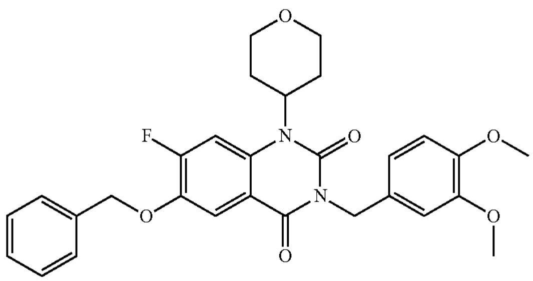 [SMILES: COc1ccc(Cn2c(=O)c3cc(OCc4ccccc4)c(F)cc3n(C3CCOCC3)c2=O)cc1OC] | 6-(benzyloxy)-3-(3,4-dimethoxybenzyl)-7-fluoro-1-(tetrahydro-2H-pyran-4-yl)quinazoline-2,4(1H,3H)-dione | 1H NMR (600 MHz, DMSO-d$_6$) δ ppm 1.65 (d, 2 H) 2.68-2.72 (m, 2 H) 3.55 (dd, 2 H) 3.70 (s, 3 H) 3.71 (s, 3 H) 3.93 (dd, 2 H) 4.60 (br. s, 1 H) 5.06 (s, 2 H) 5.28 (s, 2 H) 6.83 (dd, 1 H) 6.87 (d, 1 H) 6.99 (s, 1 H) 7.35 (t, 1 H) 7.42 (t, 2 H) 7.48 (dd, 2 H) 7.79 (d, 1 H) 7.87 (d, 1 H) | 521 |
| 63 | 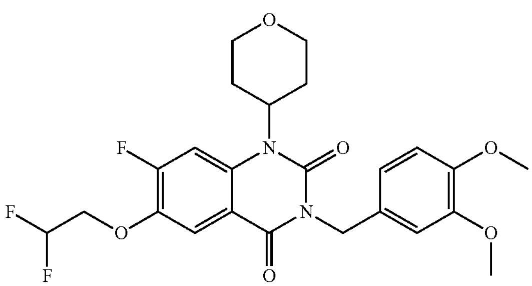 [SMILES: COc1ccc(Cn2c(=O)c3cc(OCC(F)F)c(F)cc3n(C3CCOCC3)c2=O)cc1OC] | 6-(2,2-difluoroethoxy)-3-(3,4-dimethoxybenzyl)-7-fluoro-1-(tetrahydro-2H-pyran-4-yl)quinazoline-2,4(1H,3H)-dione | 1H NMR (500 MHz, DMSO-d$_6$) δ ppm 1.64 (d, 2 H) 2.68 (qd, 2 H) 3.55 (t, 2 H) 3.72 (s, 3 H) 3.73 (s, 3 H) 3.93 (dd, 2 H) 4.53 (td, 2 H) 4.61 (br. t, 1 H) 5.05 (s, 2 H) 6.44 (tt, 1 H) 6.83 (dd, 1 H) 6.87 (d, 1 H) 7.00 (d, 1 H) 7.80 (d, 1 H) 7.92 (d, 1 H) | 495 |
| 64 | 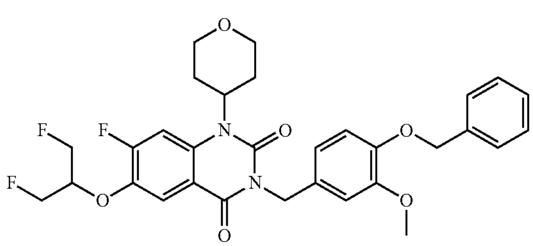 [SMILES: COc1cc(Cn2c(=O)c3cc(OC(CF)CF)c(F)cc3n(C3CCOCC3)c2=O)ccc1OCc1ccccc1] | 3-[4-(benzyloxy)-3-methoxybenzyl]-6-[(1,3-difluoropropan-2-yl)oxy]-7-fluoro-1-(tetrahydro-2H-pyran-4-yl)quinazoline-2,4(1H,3H)-dione | 1H NMR (500 MHz, DMSO-d$_6$) δ ppm 1.59 (d, 2 H) 2.63-2.72 (m, 2 H) 3.50 (t, 2 H) 3.70 (s, 3 H) 3.71 (s, 3 H) 3.49 (t, 2 H) 3.94 (dd, 5 H) 4.64 (br. t, 1 H) 5.02 (s, 2 H) 5.30 (s, 2 H) 6.83 (d, 1 H) 6.80 (dd, 1 H) 6.86 (d, 1 H) 6.98 (d, 1 H) 7.03 (dd, 1 H) 7.26 (dd, 1 H) | 585 |
| 65 | 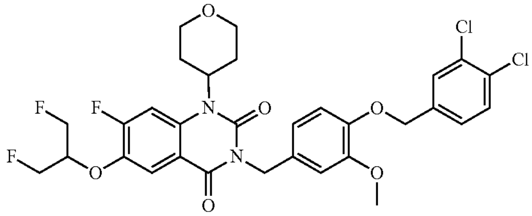 [SMILES: COc1cc(Cn2c(=O)c3cc(OC(CF)CF)c(F)cc3n(C3CCOCC3)c2=O)ccc1OCc1ccc(Cl)c(Cl)c1] | 3-{4-[(3,4-dichlorobenzyl)oxy]-3-methoxybenzyl}-6-[(1,3-difluoropropan-2-yl)oxy]-7-fluoro-1-(tetrahydro-2H-pyran-4-yl)quinazoline-2,4(1H,3H)-dione | 1H NMR (600 MHz, DMSO-d$_6$) δ ppm 1.62 (d, 2 H) 2.63-2.70 (m, 2 H) 3.53 (t, 2 H) 3.74 (s, 3 H) 3.92 (dd, 2 H) 4.58 (br. t, 1 H) 4.65 (dd, 1 H) 4.72 (dd, 2 H) 4.80 (dd, 1 H) 5.01 (m, 1 H) 5.05 (d, 2 H) 5.10 (d, 2 H) 6.79 (d, 1 H) 6.91 (dd, 1 H) 7.02 (d, 1 H) 7.39 (dd, 1 H) 7.62 (dd, 1 H) 7.66 (d, 1 H) 7.85 (dd, 1 H) 7.88 (d, 1 H) | 653 |

TABLE 1-continued

| Compound No. | STRUCTURE | NOMENCLATURE | NMR | MASS |
|---|---|---|---|---|
| 66 | 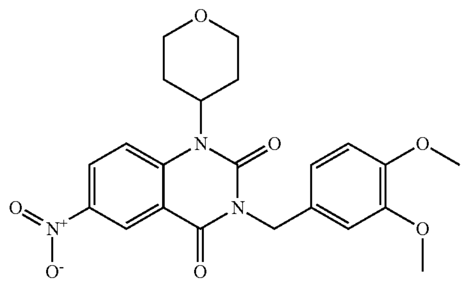 [SMILES: COc1ccc(Cn2c(=O)c3cc([N+](=O)[O-])ccc3n(C3CCOCC3)c2=O)cc1OC] | 3-(3,4-dimethoxybenzyl)-6-nitro-1-(tetrahydro-2H-pyran-4-yl)quinazoline-2,4(1H,3H)-dione | 1H NMR (500 MHz, DMSO-$d_6$) δ ppm 1.69 (d, 2 H) 2.66 (qd, 2 H) 3.54 (t, 2 H) 3.70 (s, 3 H) 3.71 (s, 3 H) 3.97 (dd, 2 H) 4.84 (br. t, 1 H) 5.06 (s, 2 H) 6.87 (s, 2 H) 7.01 (s, 1 H) 8.02 (d, 1 H) 8.49 (dd, 1 H) 8.75 (d, 1 H) | 442 |
| 67 | 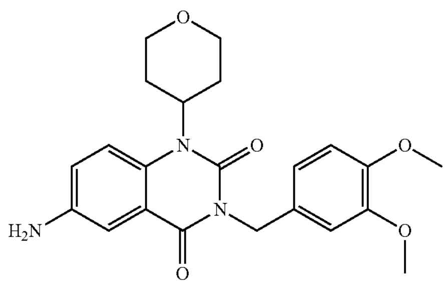 [SMILES: COc1ccc(Cn2c(=O)c3cc(N)ccc3n(C3CCOCC3)c2=O)cc1OC] | 6-amino-3-(3,4-dimethoxybenzyl)-1-(tetrahydro-2H-pyran-4-yl)quinazoline-2,4(1H,3H)-dione | 1H NMR (500 MHz, DMSO-$d_6$) δ ppm 1.59 (d, 2 H) 2.68 (qd, 2 H) 3.49 (t, 2 H) 3.70 (s, 3 H) 3.71 (s, 3 H) 3.95 (dd, 2 H) 4.64 (br. t, 1 H) 5.03 (s, 2 H) 5.30 (s, 2 H) 6.81 (dd, 1 H) 6.86 (d, 1 H) 6.98 (d, 1 H) 7.03 (dd, 1 H) 7.26 (d, 1 H) 7.48 (d, 1 H) | 412 |
| 68 | 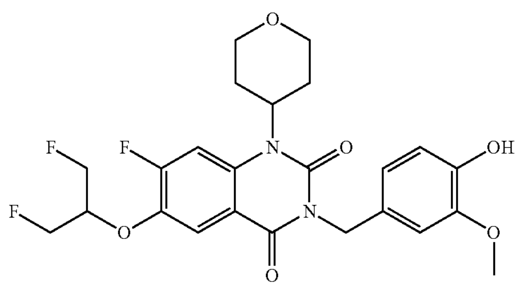 [SMILES: COc1cc(Cn2c(=O)c3cc(OC(CF)CF)c(F)cc3n(C3CCOCC3)c2=O)ccc1O] | 6-[(1,3-difluoropropan-2-yl)oxy]-7-fluoro-3-(4-hydroxy-3-methoxybenzyl)-1-(tetrahydro-2H-pyran-4-yl)quinazoline-2,4(1H,3H)-dione | 1H NMR (500 MHz, DMSO-$d_6$) δ ppm 1.63 (d, 2 H) 2.63-2.72 (m, 2 H) 3.54 (t, 2 H) 3.72 (s, 3 H) 3.92 (dd, 2 H) 4.60 (br. t, 1 H) 4.65 (m, 1 H) 4.73 (m, 2 H) 4.81 (dd, 1 H) 4.99 (s, 2 H) 5.09 (br. m, 1 H) 6.67 (d, 1 H) 6.72 (dd, 1 H) 6.96 (d, 1 H) 7.86 (d, 1 H) 7.89 (s, 1 H) 8.88 (s, 1 H) | 495 |

EXAMPLES

The procedures and examples that follow describe the preparation of certain compounds in accordance with the invention. These procedures and examples are not limiting, and serve merely to illustrate the present invention.

A person skilled in the art can without difficulty adapt the teaching below to the compounds of general formula (I). He will be capable of selecting, in the light of his general knowledge and of the literature, the appropriate protecting groups for introducing all the groups or functions described in the present invention.

In the procedures and examples below:
the mass spectra are acquired on a quadrupolar spectrometer of Platform LCZ type (Waters) or of ZQ 4000 type (Waters) in positive electrospray ionization mode;
the NMR (nuclear magnetic resonance) spectra are acquired on a Fourier transform spectrometer (Brüker), at a temperature of 300 K (exchangeable protons not recorded);
s=singlet;
d=doublet;
m=multiplet;
br=broad signal;
t=triplet;
q=quartet;
DMSO-$d_6$=deuterated dimethyl sulfoxide;
$CDCl_3$=deuterated chloroform.

The solvent mixtures are quantified as volume ratios.
The NMR and mass spectra confirm the structures of the compounds obtained according to the examples below.

In the examples that follow, the following abbreviations are used:

| | |
|---|---|
| ACN: | acetonitrile |
| EtOAc: | ethyl acetate |
| AcOH: | acetic acid |
| DAST: | (diethylamino)sulfur trifluoride |
| DBU: | 1,8-diazabicyclo[5.4.0]undec-7-ene |
| DCM: | dichloromethane |
| DCE: | 1,2-dichloroethane |
| DEAD: | diethyl azodicarboxylate |
| DIAD: | diisopropyl azodicarboxylate |
| DIEA: | diisopropylamine |
| DMF: | N,N-dimethylformamide |
| PE: | petroleum ether |
| $Et_2O$: | diethyl ether |
| EtOH: | ethanol |
| HBTU: | O-(benzotriazol-1-yl)-N,N,N',N'-tetramethyluronium hexafluorophosphate |
| IBCF: | isobutyl chloroformate |
| MeOH: | methanol |
| $NaBH(OAc)_3$: | sodium triacetoxyborohydride |
| RT: | room temperature |

| | |
|---|---|
| min: | minute |
| THF: | tetrahydrofuran |
| NEt₃: | triethylamine |
| TFA: | trifluoroacetic acid |

Example 1

Compound 6

Synthesis of 6-bromo-3-(3,4-dimethoxybenzyl)-1-(tetrahydro-2H-pyran-4-yl)quinazoline-2,4(1H,3H)-dione

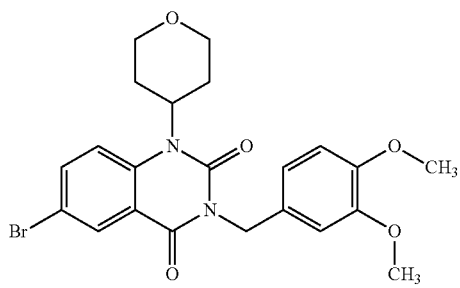 [SMILES: COc1ccc(Cn2c(=O)c3cc(Br)ccc3n(C3CCOCC3)c2=O)cc1OC]

Step 1.1:

5-bromo-2-(tetrahydro-2H-pyran-4-ylamino)benzoic acid

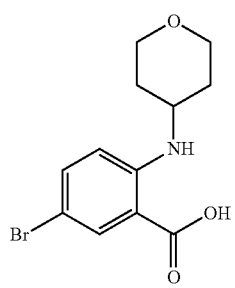 [SMILES: O=C(O)c1cc(Br)ccc1NC1CCOCC1]

A mixture of 5 g of 2-amino-5-bromobenzoic acid, 9.27 g of tetrahydro-4H-pyran-4-one and 32 g of Na₂SO₄ in 50 ml of acetic acid is stirred overnight at room temperature. The reaction mixture is filtered. A further 9.27 g of tetrahydro-4H-pyran-4-one and 32 g of Na₂SO₄ are added and the resulting mixture is stirred overnight at room temperature. This mixture is filtered and 9.81 g of NaBH(OAc)₃ are added. The resulting mixture is allowed to cool to room temperature over 2 hours. The reaction medium is evaporated under reduced pressure and the residue is taken up in EtOAc. It is washed with aqueous 1N HCl solution. The organic phase is dried over Na₂SO₄, filtered and evaporated under reduced pressure to give 3.35 g of the expected product.

Step 1.2:

5-bromo-N-(3,4-dimethoxybenzyl)-2-(tetrahydro-2H-pyran-4-ylamino)benzamide

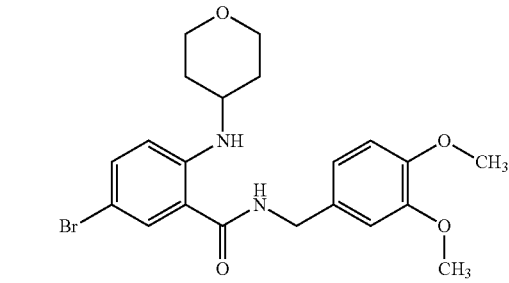 [SMILES: COc1ccc(CNC(=O)c2cc(Br)ccc2NC2CCOCC2)cc1OC]

A mixture of 1 g of the compound obtained in Step 1.1, 0.646 g of veratrylamine, 1.152 g of DIEA and 1.69 g of HBTU in 50 ml of DMF is stirred for 2 days at room temperature. The reaction medium is evaporated under reduced pressure. The residue is chromatographed on silica gel, eluting with a DCM/EtOAc mixture from (100/0, v/v) to (80/20, v/v) to give 1.2 g of a solid, which is used without purification in the following step.

Step 1.3:

6-bromo-3-(3,4-dimethoxybenzyl)-1-(tetrahydro-2H-pyran-4-yl)quinazoline-2,4(1H,3H)-dione

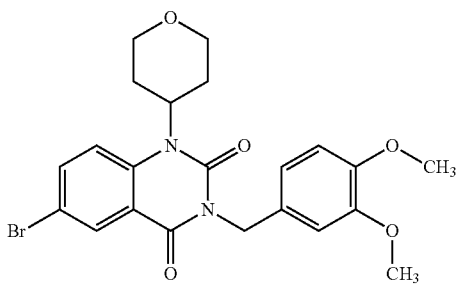 [SMILES: COc1ccc(Cn2c(=O)c3cc(Br)ccc3n(C3CCOCC3)c2=O)cc1OC]

A mixture of 1.67 g of IBCF, 1.1 g of the compound obtained in Step 1.2, 3.23 g of NaOH and 0.83 g of tetrabutylammonium hemisulfate in 150 ml of DCE is stirred overnight. The reaction medium is filtered and evaporated under reduced pressure. The residue is chromatographed on silica gel, eluting with a DCM/EtOAc mixture from (100/0, v/v) to (80/20, v/v) to give 0.649 g of the expected product.

Example 2

Compound 34

Synthesis of 3-(3,4-dimethoxybenzyl)-6-iodo-1-(tetrahydro-2H-pyran-4-yl)quinazoline-2,4(1H,3H)-dione

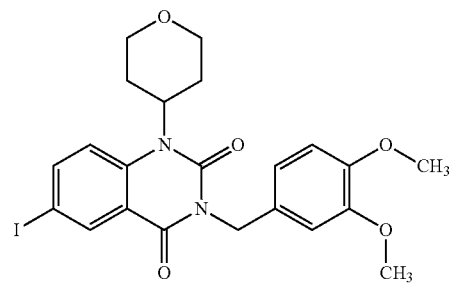

Step 2.1:

N-(3,4-dimethoxybenzyl)-5-iodo-2-(tetrahydro-2H-pyran-4-ylamino)benzamide

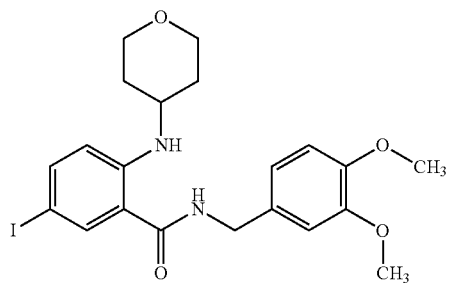 [SMILES: COc1ccc(CNC(=O)c2cc(I)ccc2NC2CCOCC2)cc1OC]

A mixture of 14.22 g of 5-iodo-2-(tetrahydro-2H-pyran-4-ylamino)benzoic acid, 18.4 g of HBTU, 21.28 g of DIEA and 9.18 g of veratrylamine in 200 ml of DMF is stirred overnight at room temperature. The reaction medium is evaporated under reduced pressure. The residue is taken up in 3000 mL of EtOAc. The solution is washed with aqueous 0.5N HCl solution, with saturated aqueous $NaHCO_3$ solution, and then with saturated aqueous NaCl solution. The organic phase is dried over $MgSO_4$, filtered and evaporated under reduced pressure to give 18 g of the expected product.

Step 2.2:

3-(3,4-dimethoxybenzyl)-6-iodo-1-(tetrahydro-2H-pyran-4-yl)quinazoline-2,4(1H,3H)-dione

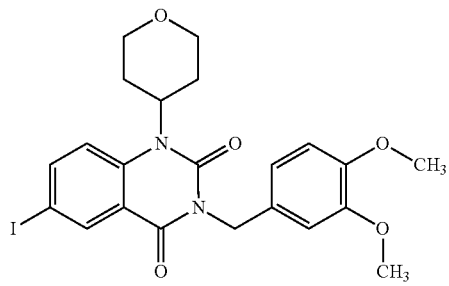 [SMILES: COc1ccc(Cn2c(=O)c3cc(I)ccc3n(C3CCOCC3)c2=O)cc1OC]

2.9 g of NaOH are added to a solution of 18 g of the compound obtained in Step 2.1 in 200 ml of DCE and the mixture is left to react for 30 minutes at room temperature. 1.5 g of NaH are added and the mixture is left to react for 30 minutes at room temperature. 51.1 g of IBCF are added and the reaction mixture is heated for 4 hours at 80° C. The resulting mixture is evaporated under reduced pressure and the residue is taken up in 200 ml of DMF. 8.7 g of NaOH and 12.3 g of tetrabutylammonium hemisulfate are added. The mixture is heated for 4 hours at 80° C. and then overnight at room temperature. The residue is chromatographed on silica gel, eluting with a DCM/EtOAc mixture from (100/0, v/v) to (80/20, v/v) to give 9 g of the expected product.

Example 3

Compound 11

Synthesis of {[3-(3,4-dimethoxybenzyl)-2,4-dioxo-1-(tetrahydro-2H-thiopyran-4-yl)-1,2,3,4-tetrahydro-quinazolin-6-yl]oxy}acetonitrile

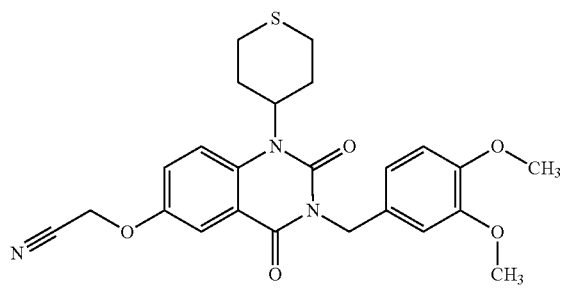 [SMILES: COc1ccc(Cn2c(=O)c3cc(OCC#N)ccc3n(C3CCSCC3)c2=O)cc1OC]

Step 3.1:

5-(benzyloxy)-N-(3,4-dimethoxybenzyl)-2-(tetrahydro-2H-thiopyran-4-ylamino)benzamide

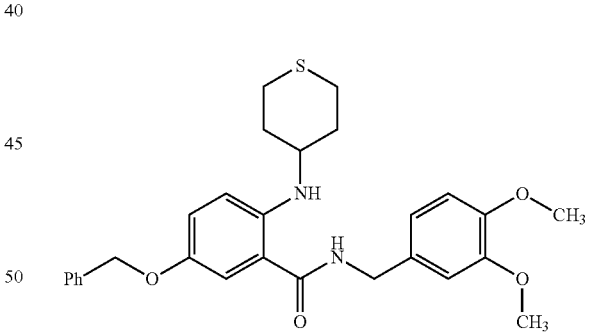

A mixture of 0.235 g of 2-amino-5-(benzyloxy)-N-(3,4-dimethoxybenzyl)benzamide, 0.090 g of tetrahydro-4H-thiopyran-4-one and 0.78 g of sodium triacetoxyborohydride in 0.5 ml of acetic acid is irradiated in a microwave field for 5 minutes at 130° C. 1N HCl is added and the mixture is extracted with EtOAc. The organic phase is dried over $MgSO_4$ and filtered, and the filtrate is evaporated under reduced pressure. The residue is chromatographed on silica gel, eluting with a heptane/EtOAc mixture from (90/10, v/v) to (20/80, v/v) to give 0.2 g of the expected product.

Step 3.2:

6-(benzyloxy)-3-(3,4-dimethoxybenzyl)-1-(tetrahydro-2H-thiopyran-4-yl)quinazoline-2,4(1H,3H)-dione

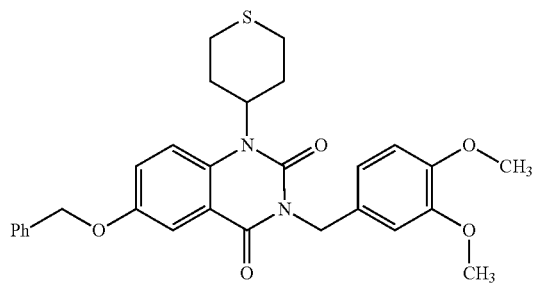 [SMILES: COc1ccc(Cn2c(=O)c3cc(OCc4ccccc4)ccc3n(C3CCSCC3)c2=O)cc1OC]

A mixture of 2.5 g of the compound obtained in Step 3.1, and 6.7 g of NaOH in 100 ml of DCE is stirred for 30 minutes at room temperature. 2.77 g of IBCF are then added and the mixture is stirred for 2 hours at room temperature. The same amounts of NaOH and IBCF are again added and the resulting mixture is stirred overnight at room temperature. Since the reaction is not complete, 6.7 g of NaOH, 1.39 g of IBCF and 0.05 g of tetrabutylammonium sulfate are added, and the mixture is then stirred for 3 days at room temperature. The resulting mixture is filtered, and the filtrate is evaporated under reduced pressure. The residue is chromatographed on silica gel, eluting with a DCM/EtOAc mixture from (100/0, v/v) to (80/20, v/v) to give 2.07 g of the expected product.

Step 3.3:

3-(3,4-dimethoxybenzyl)-6-hydroxy-1-(tetrahydro-2H-thiopyran-4-yl)quinazoline-2,4(1H,3H)-dione

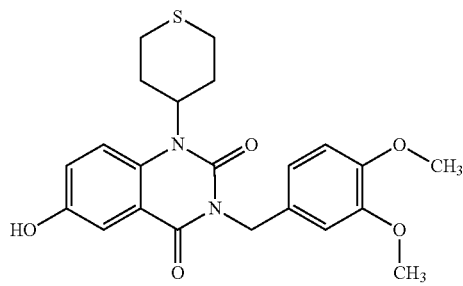 [SMILES: COc1ccc(Cn2c(=O)c3cc(O)ccc3n(C3CCSCC3)c2=O)cc1OC]

A mixture of 0.200 g of the compound obtained in Step 3.2, and 1.22 g of formic acid is irradiated in a microwave field for 2 minutes at 180° C. The reaction mixture is taken up in EtOAc and then evaporated under reduced pressure. The residue is chromatographed on silica gel, eluting with a CH$_2$Cl$_2$/MeOH mixture from (100/0, v/v) to (97/3, v/v) to give the expected product.

Step 3.4:

{[3-(3,4-dimethoxybenzyl)-2,4-dioxo-1-(tetrahydro-2H-thiopyran-4-yl)-1,2,3,4-tetrahydroquinazolin-6-yl]oxy}acetonitrile

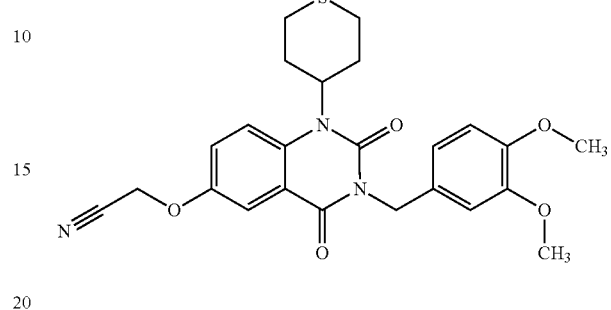

A mixture of 0.16 g of the compound obtained in Step 3.3, 0.054 g of bromoacetonitrile and 0.243 g of Cs$_2$CO$_3$ in 1 ml of DMF is irradiated in a microwave field for 15 minutes at 100° C. The reaction mixture is evaporated under reduced pressure. The residue is taken up in DCM, washed with water, dried over Na$_2$SO$_4$ and filtered, and the filtrate is evaporated under reduced pressure. The residue is chromatographed on silica gel, eluting with an EtOAc/DCM mixture from (10/90, v/v) to (20/80, v/v) to give 0.138 mg of the expected product.

Example 4

Compound 63

Synthesis of 6-(2,2-difluoroethoxy)-3-(3,4-dimethoxybenzyl)-7-fluoro-1-(tetrahydro-2H-pyran-4-yl)quinazoline-2,4(1H,3H)-dione

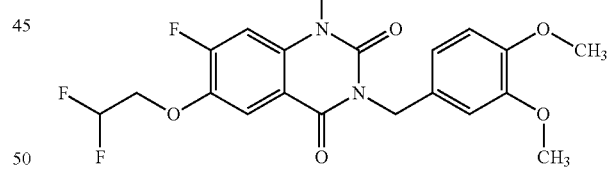

Step 4.1:

Ethyl 5-(benzyloxy)-4-fluoro-2-nitrobenzoate

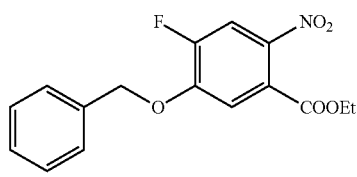 [SMILES: CCOC(=O)c1cc(OCc2ccccc2)c(F)cc1[N+](=O)[O-]]

8.25 g of Verkade base are added to a solution of 2.61 g of benzyl alcohol in 20 ml of THF. The mixture is stirred for 10 minutes at room temperature, and a solution of 5.3 g of ethyl 4,5-difluoro-2-nitrobenzoate and 2.55 g of Et$_3$N in 150 ml of THF is added to this solution. The mixture is stirred for 1 hour at room temperature. The reaction medium is evaporated under reduced pressure. The residue is taken up in DCM and washed three times with aqueous 1N HCl solution, and then with water. The organic phase is dried over MgSO$_4$ and filtered, and the filtrate is evaporated under reduced pressure. The residue is chromatographed on silica gel, eluting with a PE/DCM mixture from (100/0, v/v) to (0/100, v/v) to give 4.5 g of the expected product.

Step 4.2:

Ethyl 2-amino-5-(benzyloxy)-4-fluorobenzoate

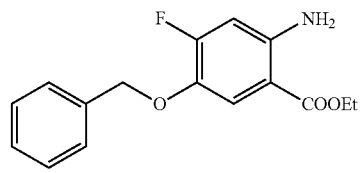 [SMILES: CCOC(=O)c1cc(OCc2ccccc2)c(F)cc1N]

1.76 g of NH$_4$Cl dissolved in 21 ml of water are added to a mixture heated to 90° C. of 7.0 g of the compound obtained in Step 4.1, and 4.44 g of Fe(0) in 400 ml of isopropanol and 100 ml of THF. The reaction mixture is heated for 4 hours at 90° C. A further 0.88 g of NH$_4$Cl is added and the mixture is heated for 2 hours at 90° C. The resulting mixture is filtered while hot and the filtrate is evaporated under reduced pressure. The residue is taken up in EtOAc and washed twice with saturated NaHCO$_3$ solution. The organic phase is dried over MgSO$_4$ and filtered, and the filtrate is evaporated under reduced pressure. The residue is chromatographed on silica gel, eluting with a PE/EtOAc mixture from (100/0, v/v) to (40/60, v/v) to give 5.2 g of the expected product.

Step 4.3:

Ethyl 5-(benzyloxy)-4-fluoro-2-(tetrahydro-2H-pyran-4-ylamino)benzoate

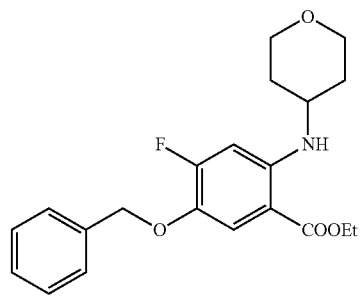 [SMILES: CCOC(=O)c1cc(OCc2ccccc2)c(F)cc1NC1CCOCC1]

A mixture of 10.5 g of the compound obtained in Step 4.2, 29.07 g of tetrahydro-4H-pyran-4-one and 51.56 g of Na$_2$SO$_4$ in 360 ml of acetic acid is stirred overnight at room temperature. 34.62 g of sodium triacetoxyborohydride are then added and the mixture is stirred for 3 hours at room temperature. The resulting mixture is evaporated under reduced pressure and the residue is taken up in EtOAc. This solution is washed with water and then 4 times with saturated aqueous NaHCO$_3$ solution. The resulting solution is dried over MgSO$_4$ and filtered, and the filtrate is evaporated under reduced pressure. The residue is chromatographed on silica gel, eluting with a PE/EtOAc mixture from (100/0, v/v) to (50/50, v/v) to give 10.55 g of the expected product.

Step 4.4:

5-(benzyloxy)-4-fluoro-2-(tetrahydro-2H-pyran-4-ylamino)benzoic acid

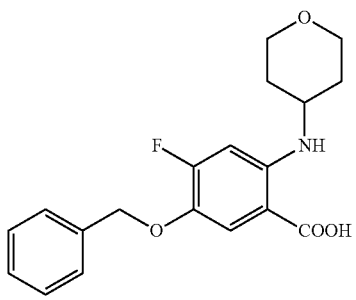 [SMILES: O=C(O)c1cc(OCc2ccccc2)c(F)cc1NC1CCOCC1]

A mixture of 1.0 g of the compound obtained in Step 4.3 and 0.45 g of KOH in 16 ml of isopropanol and 4 ml of water is irradiated in a microwave field for 20 minutes at 130° C. The reaction medium is evaporated under reduced pressure. Water is added, the resulting mixture is acidified with aqueous 1N HCl solution to pH 3 and this mixture is extracted with EtOAc. The organic phase is dried over Na$_2$SO$_4$ and filtered, and the filtrate is evaporated under reduced pressure to give 0.91 g of the expected product.

Step 4.5:

5-(benzyloxy)-N-(3,4-dimethoxybenzyl)-4-fluoro-2-(tetrahydro-2H-pyran-4-ylamino)benzamide

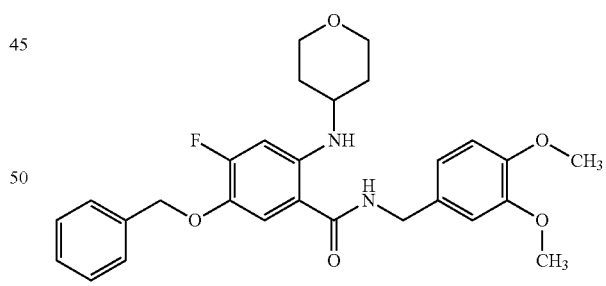

A mixture of 14 g of the compound obtained in Step 4.4, 7.46 g of veratrylamine, 19.99 g of HBTU and 13.1 g of DIEA in 300 ml of DMF is stirred for 2 hours at room temperature. The solvent is evaporated off under reduced pressure and the residue is taken up in DCM. The resulting solution is washed twice with saturated aqueous NaHCO$_3$ solution. The organic phase is dried over Na$_2$SO$_4$ and filtered, and the filtrate is evaporated under reduced pressure. The residue is chromatographed on silica gel, eluting with a PE/EtOAc mixture from (90/10, v/v) to (40/60, v/v) to give 16 g of the expected product.

Step 4.6:

6-(benzyloxy)-3-(3,4-dimethoxybenzyl)-7-fluoro-1-(tetrahydro-2H-pyran-4-yl)quinazoline-2,4(1H,3H)-dione

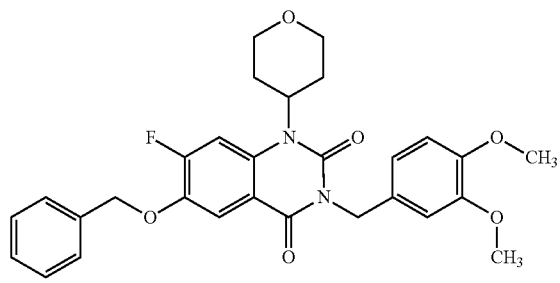 [SMILES: COc1ccc(Cn2c(=O)c3cc(OCc4ccccc4)c(F)cc3n(C3CCOCC3)c2=O)cc1OC]

A mixture of 1.0 g of the compound obtained in Step 4.5, 1.223 g of 4-nitrophenyl chloroformate and 0.915 g of DIEA in 15 ml of THF is irradiated in a microwave field for 15 minutes at 80° C. 0.616 g of DBU is then added and the mixture is stirred for 1 hour at room temperature. The reaction medium is evaporated under reduced pressure. The residue is taken up in EtOAc and washed twice with saturated aqueous $NaHCO_3$ solution, then with aqueous 1M $KHSO_4$ solution and then with water. The organic phase is dried over $Na_2SO_4$ and filtered, and the filtrate is evaporated under reduced pressure. The residue is chromatographed on silica gel, eluting with a DCM/EtOAc mixture from (100/0, v/v) to (60/40, v/v) to give 0.74 g of the expected product.

Step 4.7:

3-(3,4-dimethoxybenzyl)-7-fluoro-6-hydroxy-1-(tetrahydro-2H-pyran-4-yl)quinazoline-2,4(1H,3H)-dione

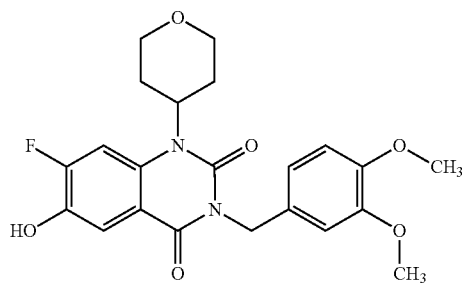 [SMILES: COc1ccc(Cn2c(=O)c3cc(O)c(F)cc3n(C3CCOCC3)c2=O)cc1OC]

A mixture of 0.2 g of the compound obtained in Step 4.6, 0.036 g of ammonium formate and 0.041 g of Pd/C (10%) in 4 ml of EtOH is irradiated in a microwave field for 5 minutes at 60° C. DCM is added, the mixture is filtered and the filtrate is evaporated under reduced pressure. The residue is chromatographed on silica gel, eluting with a PE/EtOAc mixture from (95/5, v/v) to (0/100, v/v) to give 0.11 g of the expected product.

Step 4.8:

6-(2,2-difluoroethoxy)-3-(3,4-dimethoxybenzyl)-7-fluoro-1-(tetrahydro-2H-pyran-4-yl)-quinazoline-2,4(1H,3H)-dione

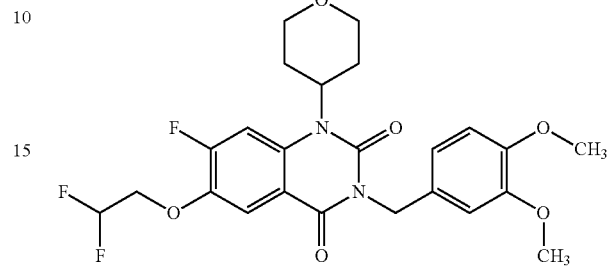

0.125 g of difluoroethanol, 0.47 g of tributylphosphine and 0.38 g of DIAD are successively added to a solution of 0.4 g of the compound obtained in Step 4.7 in 15 ml of THF. This mixture is stirred overnight at room temperature. The reaction medium is evaporated under reduced pressure. The residue is chromatographed on silica gel, eluting with a PE/EtOAc mixture from (100/0, v/v) to (30/70) to give 0.38 g of the expected product.

Example 5

Compound 50

Synthesis of 3-(3,4-dimethoxybenzyl)-6-(2-fluoroethoxy)-1-(tetrahydro-2H-pyran-4-yl)-quinazoline-2,4(1H,3H)-dione

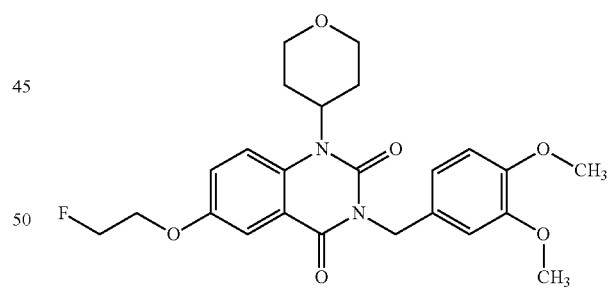

A mixture of 0.2 g of 3-(3,4-dimethoxybenzyl)-6-hydroxy-1-(tetrahydro-2H-pyran-4-yl)-quinazoline-2,4(1H,3H)-dione and 0.32 g of $Cs_2CO_3$ in 10 ml of DMF is irradiated in a microwave field for 1 minute at 100° C. 0.169 g of fluoroethanol are then added and the mixture is irradiated in a microwave field for 5 minutes at 140° C. The reaction medium is evaporated under reduced pressure. The residue is taken up in EtOAc and washed with water and then with saturated NaCl solution. The resulting solution is dried over $Na_2SO_4$, filtered and evaporated under reduced pressure. The residue is chromatographed on silica gel, eluting with a DCM/EtOAc mixture from (80/20, v/v) to give 0.212 g of the expected product.

Example 6

Compound 28

3-(3,4-dimethoxybenzyl)-6-(prop-2-yn-1-ylamino)-1-(tetrahydro-2H-pyran-4-yl)quinazoline-2,4(1H,3H)-dione

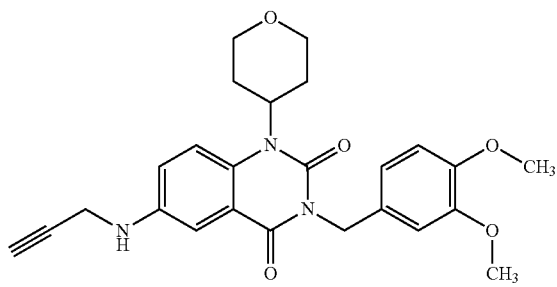 [SMILES: C#CCNc1ccc2c(c1)c(=O)n(Cc1ccc(OC)c(OC)c1)c(=O)n2C1CCOCC1]

Step 6.1:

5-nitro-2-(tetrahydro-2H-pyran-4-ylamino)benzoic acid

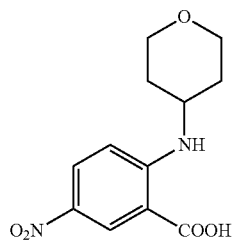 [SMILES: O=C(O)c1cc([N+](=O)[O-])ccc1NC1CCOCC1]

A mixture of 5.1 g of 2-fluoro-5-nitrobenzoic acid and 6.21 g of tetrahydro-2H-pyran-4-amine in 5 ml of DMF is irradiated in a microwave field for 15 minutes at 100° C. The mixture is irradiated a second time for 15 minutes at 100° C. The same reaction is repeated on identical amounts of reagents. All the reaction mixtures are pooled and the solvent is evaporated off under reduced pressure. The residue is recrystallized from EtOAc to give 6 g of expected product.

Step 6.2:

N-(3,4-dimethoxybenzyl)-5-nitro-2-(tetrahydro-2H-pyran-4-ylamino)benzamide

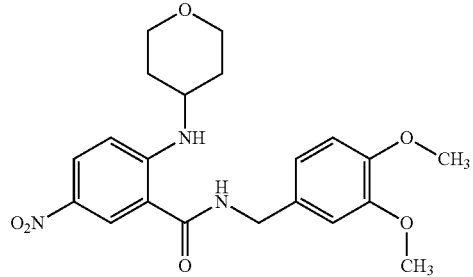 [SMILES: COc1ccc(CNC(=O)c2cc([N+](=O)[O-])ccc2NC2CCOCC2)cc1OC]

A mixture of 5.8 g of the compound obtained in Step 6.1, 7.02 g of DIEA and 12.38 g of HBTU is stirred for 30 minutes at room temperature. 4.37 g of veratrylamine are then added and the resulting mixture is stirred overnight at room temperature. The resulting mixture is evaporated under reduced pressure and the residue is taken up in EtOAc. This solution is washed with water and then sequentially with 1N HCl solution, with water, with saturated NaHCO₃ solution, with water and with saturated NaCl solution. The resulting solution is dried over Na₂SO₄ and filtered, and the solvent is evaporated off under reduced pressure. The residue is chromatographed on silica gel, eluting with an EtOAc/heptane mixture from (50/50, v/v) to (70/30, v/v) to give 7.7 g of the expected product.

Step 6.3:

3-(3,4-dimethoxybenzyl)-6-nitro-1-(tetrahydro-2H-pyran-4-yl)quinazoline-2,4(1H,3H)-dione

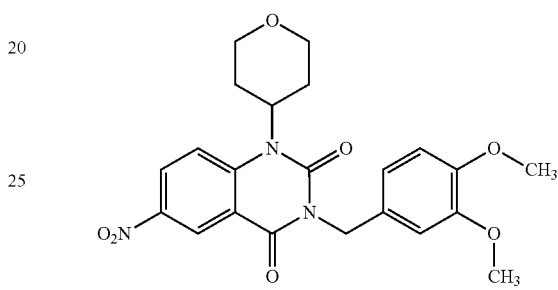

15.19 g of IBCF are added to a mixture of 7.7 g of the compound obtained in Step 6.2, 29.65 g of NaOH and 3.14 g of tetrabutylammonium sulfate in 618 ml of DCE. This mixture is stirred overnight at room temperature. The resulting mixture is filtered and the filtrate is washed with 1N HCl solution, with water and with saturated NaCl solution. The resulting solution is dried over Na₂SO₄ and filtered, and the solvent is evaporated off under reduced pressure. The residue is chromatographed on silica gel, eluting with an EtOAc/DCM mixture from (5/95, v/v) to (100/0, v/v) to give 7.35 g of the expected product.

Step 6.4:

6-amino-3-(3,4-dimethoxybenzyl)-1-(tetrahydro-2H-pyran-4-yl)quinazoline-2,4(1H,3H)-dione

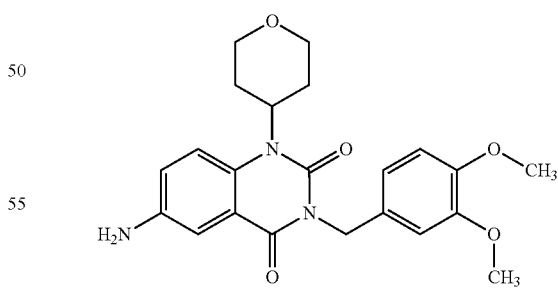

A mixture of 1 g of the compound obtained in Step 6.3, 0.36 g of ammonium formate and 0.24 g of Pd/C (10%) in 10 ml of EtOH purged beforehand with nitrogen is irradiated in a microwave field for 10 minutes at 80° C. The resulting mixture is filtered and the filtrate is evaporated under reduced pressure. The residue is chromatographed on silica gel, eluting with an EtOAc/DCM mixture from (0/100, v/v) to (100/0, v/v) to give the expected product.

Step 6.5:

3-(3,4-dimethoxybenzyl)-6-(prop-2-yn-1-ylamino)-1-(tetrahydro-2H-pyran-4-yl)quinazoline-2,4(1H,3H)-dione

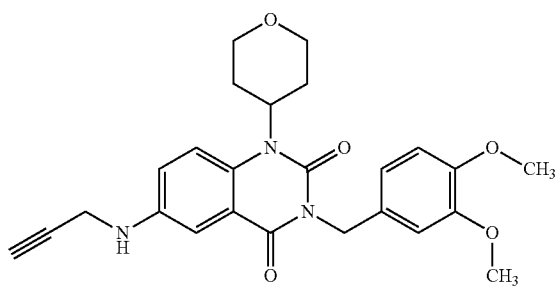 [SMILES: C#CCNc1ccc2c(c1)c(=O)n(Cc1ccc(OC)c(OC)c1)c(=O)n2C1CCOCC1]

A mixture of 0.25 g of the compound obtained in Step 6.4, 0.094 g of propargyl bromide, 0.12 g of K$_2$CO$_3$ and 0.009 g of sodium iodide in 8.25 ml of DMF is irradiated in a microwave field for 3 hours at 100° C. The resulting mixture is evaporated under reduced pressure. The residue is chromatographed on silica gel, eluting with an MeOH/DCM mixture from (0/100) to (2/98, v/v) to give 0.155 g of the expected product.

Example 7

Compound 39

Synthesis of 3-(3,4-dimethoxybenzyl)-6-(1-hydroxyethyl)-1-(tetrahydro-2H-pyran-4-yl)-quinazoline-2,4(1H,3H)-dione

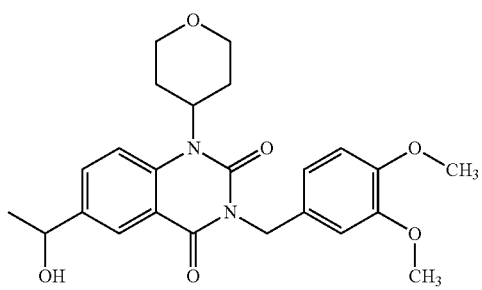 [SMILES: COc1ccc(Cn2c(=O)c3cc(C(C)O)ccc3n(C3CCOCC3)c2=O)cc1OC]

Step 7.1:

6-acetyl-3-(3,4-dimethoxybenzyl)-1-(tetrahydro-2H-pyran-4-yl)quinazoline-2,4(1H,3H)-dione

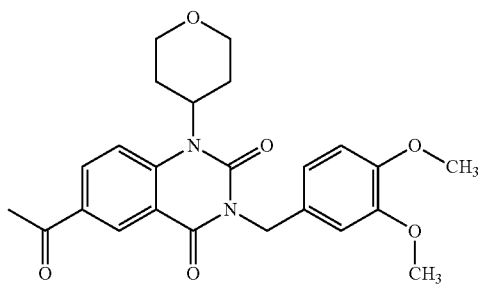 [SMILES: COc1ccc(Cn2c(=O)c3cc(C(C)=O)ccc3n(C3CCOCC3)c2=O)cc1OC]

A mixture of 1 g of 3-(3,4-dimethoxybenzyl)-6-iodo-1-(tetrahydro-2H-pyran-4-yl)-quinazoline-2,4(1H,3H)-dione, 1.3 ml of tributyl(1-ethoxyvinyl)tin and 0.04 g of Pd(PPh$_3$)$_4$ in 20 ml of toluene is heated for 1 hour at 130° C. and then stirred for 48 hours at room temperature. The solvent is evaporated off under reduced pressure. The residue is taken up in EtOAc and washed four times with 4N HCl and then with water. The organic phase is dried over Na$_2$SO$_4$, filtered and evaporated under reduced pressure. The residue is chromatographed on silica gel, eluting with a DCM/EtOAc mixture from (80/20, v/v) to give 0.84 g of the expected product.

Step 7.2:

3-(3,4-dimethoxybenzyl)-6-(1-hydroxyethyl)-1-(tetrahydro-2H-pyran-4-yl)quinazoline-2,4(1H,3H)-dione

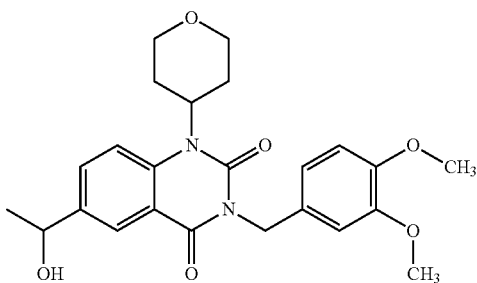 [SMILES: COc1ccc(Cn2c(=O)c3cc(C(C)O)ccc3n(C3CCOCC3)c2=O)cc1OC]

A mixture of 0.154 of the compound obtained in Step 7.1 and 0.026 g of NaBH$_4$ in 30 ml of MeOH is stirred for 2 hours at room temperature. Water is added and the mixture is neutralized with 1N HCl. The resulting mixture is evaporated under reduced pressure and the residue is taken up in DCM. This solution is filtered and evaporated under reduced pressure. The residue is chromatographed on silica gel, eluting with EtOAc to give 0.14 g of the expected product.

Example 8

Compound 43

Synthesis of 3-(3,4-dimethoxybenzyl)-6-(1-hydroxy-1-methylethyl)-1-(tetrahydro-2H-pyran-4-yl)quinazoline-2,4(1H,3H)-dione

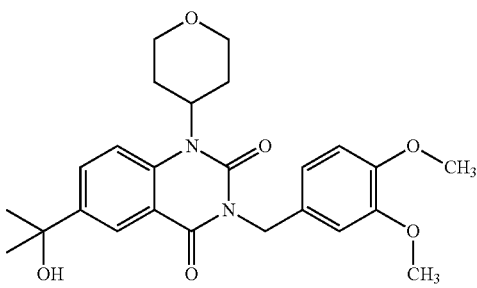 [SMILES: COc1ccc(Cn2c(=O)c3cc(C(C)(C)O)ccc3n(C3CCOCC3)c2=O)cc1OC]

0.1 g of 6-acetyl-3-(3,4-dimethoxybenzyl)-1-(tetrahydro-2H-pyran-4-yl)quinazoline-2,4(1H,3H)-dione is added to a solution of 0.143 g of methylmagnesium iodide in 1 ml of Et$_2$O. This mixture is stirred for 30 minutes at 0° C. and then overnight at room temperature. The reaction mixture is evaporated under reduced pressure. The residue is chromatographed on silica gel, eluting with EtOAc to give 0.01 g of the expected product.

Example 9

Compound 46

Synthesis of 3-(3,4-dimethoxybenzyl)-6-(1-hydroxy-1-methylbut-3-yn-1-yl)-1-(tetrahydro-2H-pyran-4-yl)quinazoline-2,4(1H,3H)-dione

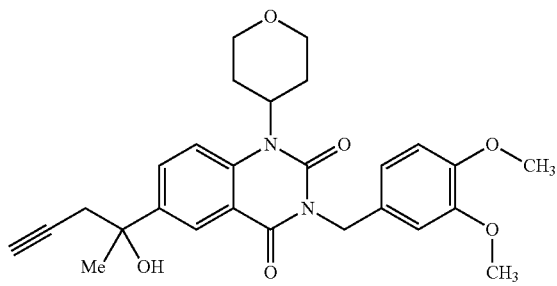 [SMILES: C#CCC(C)(O)c1ccc2c(c1)c(=O)n(Cc1ccc(OC)c(OC)c1)c(=O)n2C1CCOCC1]

Step 9.1:

3-(3,4-dimethoxybenzyl)-6-[1-hydroxy-1-methyl-4-(trimethylsilyl)but-3-yn-1-yl]-1-(tetrahydro-2H-pyran-4-yl)quinazoline-2,4(1H,3H)-dione

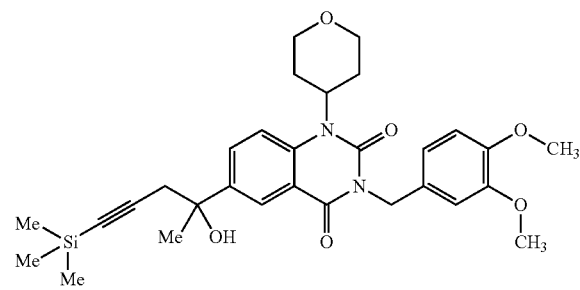 [SMILES: COc1ccc(Cn2c(=O)c3cc(C(C)(O)CC#C[Si](C)(C)C)ccc3n(C3CCOCC3)c2=O)cc1OC]

A mixture of 0.1 g of 6-acetyl-3-(3,4-dimethoxybenzyl)-1-(tetrahydro-2H-pyran-4-yl)-quinazoline-2,4(1H,3H)-dione, 0.057 g of potassium iodide, 0.01 g of lithium chloride, 0.019 g of gallium and 0.065 g of trimethylsilylpropargyl bromide in 1 ml of THF is refluxed for 2 hours and then left for 2 days at room temperature. The reaction mixture is filtered through Celite and evaporated under reduced pressure. The residue is chromatographed on silica gel, eluting with a DCM/EtOAc mixture from (70/30, v/v) to give 0.112 g of the expected product.

Step 9.2:

3-(3,4-dimethoxybenzyl)-6-(1-hydroxy-1-methylbut-3-yn-1-yl)-1-(tetrahydro-2H-pyran-4-yl)-quinazoline-2,4(1H,3H)-dione

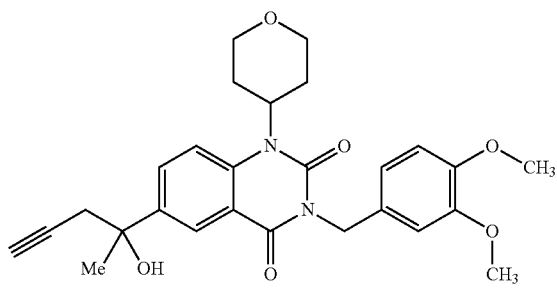 [SMILES: C#CCC(C)(O)c1ccc2c(c1)c(=O)n(Cc1ccc(OC)c(OC)c1)c(=O)n2C1CCOCC1]

A mixture of 0.112 g of the compound obtained in Step 9.1, 0.031 g of caesium fluoride and 0.003 g of tetrabutylammonium fluoride in 5 ml of DMF is stirred overnight at room temperature. The resulting mixture is evaporated under reduced pressure. The residue is taken up in DCM. This solution is washed with water, and the organic phase is dried over MgSO$_4$, filtered and evaporated under reduced pressure. The residue is chromatographed on silica gel, eluting with EtOAc to give 0.084 g of the expected product.

Example 10

Compound 27

Synthesis of 3-(3,4-dimethoxybenzyl)-6-(3-hydroxyazetidin-1-yl)-1-(tetrahydro-2H-pyran-4-yl)quinazoline-2,4(1H,3H)-dione

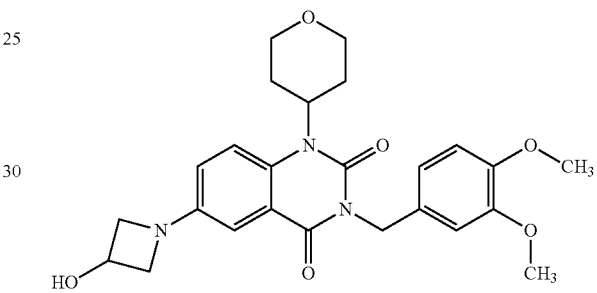

Step 10.1:

6-[3-(benzyloxy)azetidin-1-yl]-3-(3,4-dimethoxybenzyl)-1-(tetrahydro-2H-pyran-4-yl)-quinazoline-2,4(1H,3H)-dione

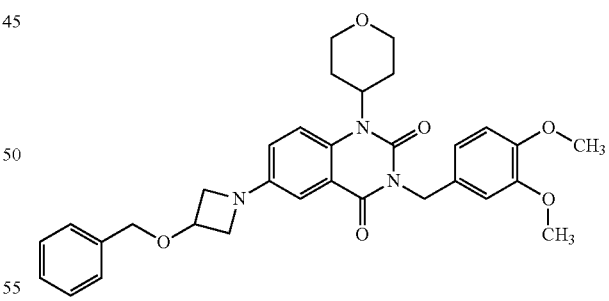

A mixture of 0.2 g of 6-bromo-3-(3,4-dimethoxybenzyl)-1-(tetrahydro-2H-pyran-4-yl)-quinazoline-2,4(1H,3H)-dione, 0.096 g of 3-benzyloxyazetidine, 0.006 g of palladium acetate, 0.055 g of sodium tert-butoxide and 0.01 ml of tributylphosphine in 4 ml of DMF is stirred for 4 days at room temperature. The reaction mixture is filtered and evaporated under reduced pressure. The residue is chromatographed on silica gel, eluting with a DCM/EtOAc mixture from (100/0, v/v) to (20/80, v/v) to give 0.041 g of the expected product.

Step 10.2:

3-(3,4-dimethoxybenzyl)-6-(3-hydroxyazetidin-1-yl)-1-(tetrahydro-2H-pyran-4-yl)-quinazoline-2,4(1H,3H)-dione

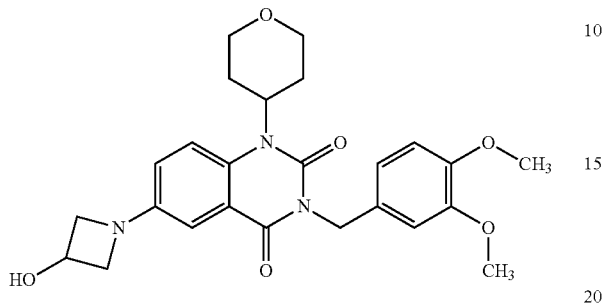

A mixture of 0.04 g of the compound obtained in Step 10.1, 0.007 g of ammonium formate and 0.008 g of Pd/C (10%) in 7.2 ml of EtOH is irradiated in a microwave field for 1 hour at 120° C. The reaction mixture is filtered and evaporated under reduced pressure. The residue is chromatographed on silica gel, eluting with a DCM/MeOH mixture from (100/0, v/v) to (95/5, v/v) to give 0.017 g of the expected product.

Example 11

Compound 3

Synthesis of 3-(3,4-dimethoxybenzyl)-6-pyridin-4-yl-1-(tetrahydro-2H-pyran-4-yl)-quinazoline-2,4(1H,3H)-dione hydrochloride

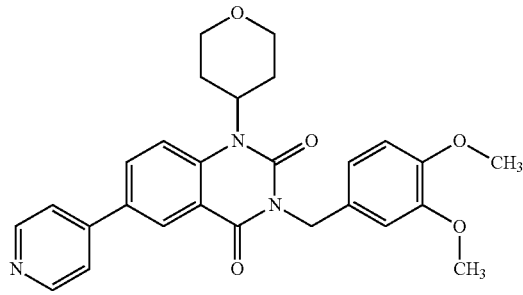 [SMILES: COc1ccc(Cn2c(=O)c3cc(-c4ccncc4)ccc3n(C3CCOCC3)c2=O)cc1OC]

A mixture of 0.25 g of 6-bromo-3-(3,4-dimethoxybenzyl)-1-(tetrahydro-2H-pyran-4-yl)-quinazoline-2,4(1H,3H)-dione, 0.0776 g of 4-pyridineboronic acid, 1 ml of aqueous 2N $K_2CO_3$ solution and 0.025 g of tetrakis(triphenylphosphine) palladium(0) in 10 ml of DMF is heated for 3 hours at 90° C. The reaction mixture is filtered and then evaporated under reduced pressure. The residue is chromatographed on silica gel, eluting with an MeOH/EtOAc mixture from (0/100, v/v) to (5/95, v/v) to give 0.17 g of the expected product in free base form. The product is dissolved in 1 ml of EtOAc, and 1 ml of $Et_2O$ is added, followed by addition of 0.5 ml of a 2N solution of HCl in $Et_2O$. 0.193 g of the hydrochloride of the expected product is obtained.

Example 12

Compound 30

Synthesis of N-{[3-(3,4-dimethoxybenzyl)-2,4-dioxo-1-(tetrahydro-2H-pyran-4-yl)-1,2,3,4-tetrahydroquinazolin-6-yl]methyl}acetamide

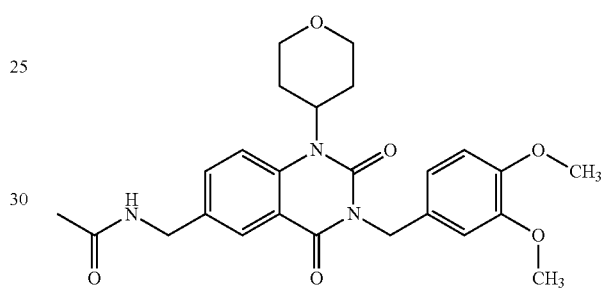

Step 12.1:

3-(3,4-dimethoxybenzyl)-2,4-dioxo-1-(tetrahydro-2H-pyran-4-yl)-1,2,3,4-tetrahydroquinazoline-6-carbonitrile

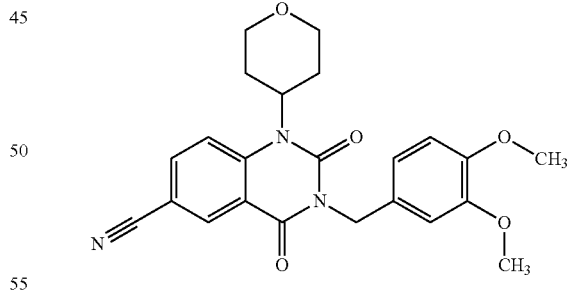

A mixture of 1.22 g of 6-bromo-3-(3,4-dimethoxybenzyl)-1-(tetrahydro-2H-pyran-4-yl)-quinazoline-2,4(1H,3H)-dione, 0.3 g of zinc cyanide and 0.089 g of tetrakis(triphenylphosphine)palladium(0) in 10 ml of DMF is irradiated in a microwave field for 3 minutes at 170° C. EtOAc is added and the mixture is washed six times with water. The resulting solution is dried over $Na_2SO_4$, filtered and evaporated under reduced pressure. The residue is chromatographed on silica gel, eluting with a DCM/EtOAc mixture from (100/0, v/v) to (80/20, v/v) to give 0.804 g of the expected product.

Step 12.2:

6-(aminomethyl)-3-(3,4-dimethoxybenzyl)-1-(tetrahydro-2H-pyran-4-yl)quinazoline-2,4(1H,3H)-dione

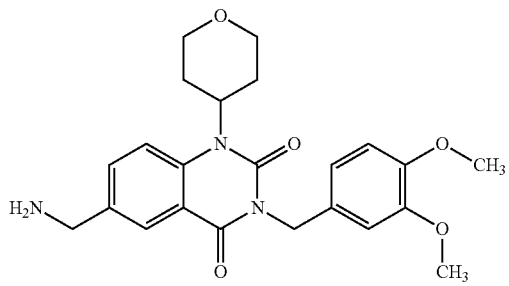 [SMILES: COc1ccc(Cn2c(=O)c3cc(CN)ccc3n(C3CCOCC3)c2=O)cc1OC]

A mixture of 0.55 g of the compound obtained in Step 12.1, and 2.94 ml of a 2M borane/dimethyl sulfide complex in THF, in 15 ml of THF is irradiated in a microwave field for 1 minute at 100° C. The reaction medium is taken up in DCM. 50 ml of 1N HCl are added and the mixture is stirred for 2 hours at room temperature. The resulting mixture is neutralized with 2N sodium hydroxide solution. This resulting mixture is extracted with DCM, dried over $Na_2SO_4$, filtered and evaporated under reduced pressure. The residue is chromatographed on an RP18 column, eluting with a water/ACN mixture from (90/10, v/v) to (50/50, v/v) to give 0.23 g of the expected product.

Step 12.3:

N-{[3-(3,4-dimethoxybenzyl)-2,4-dioxo-1-(tetrahydro-2H-pyran-4-yl)-1,2,3,4-tetrahydroquinazolin-6-yl]methyl}acetamide

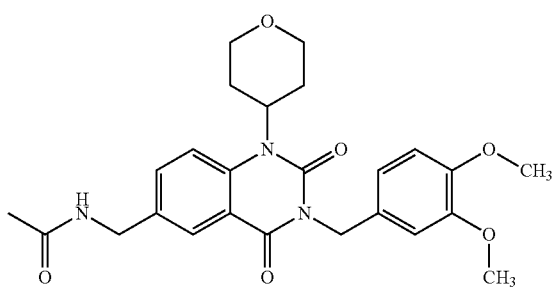 [SMILES: COc1ccc(Cn2c(=O)c3cc(CNC(C)=O)ccc3n(C3CCOCC3)c2=O)cc1OC]

0.066 g of acetic anhydride is added at 0° C. to a solution of 0.23 g of the compound obtained in Step 12.2 and 0.11 g of $Et_3N$ in 5 ml of DCM. The mixture is stirred at room temperature for 2 hours. The organic phase is washed with saturated $NH_4Cl$ solution, filtered and evaporated under reduced pressure. The residue is chromatographed on silica gel, eluting with a DCM/MeOH mixture from (99/1, v/v) to (95/5, v/v) to give 0.195 g of the expected product.

Example 13

Compound 31

Synthesis of 1-{[3-(3,4-dimethoxybenzyl)-2,4-dioxo-1-(tetrahydro-2H-pyran-4-yl)-1,2,3,4-tetrahydroquinazolin-6-yl]methyl}urea

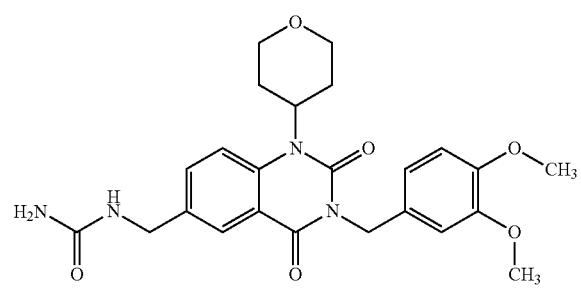 [SMILES: COc1ccc(Cn2c(=O)c3cc(CNC(N)=O)ccc3n(C3CCOCC3)c2=O)cc1OC]

A mixture of 0.1 g of 6-(aminomethyl)-3-(3,4-dimethoxybenzyl)-1-(tetrahydro-2H-pyran-4-yl)quinazoline-2,4(1H,3H)-dione and 0.025 g of potassium cyanate in 2 ml of acetic acid is irradiated in a microwave field for 4 minutes at 120° C. The resulting mixture is evaporated under reduced pressure. The residue is chromatographed on silica gel, eluting with a DCM/MeOH mixture from (100/0, v/v) to (93/7, v/v) to give 0.06 g of the expected product.

Example 14

Compound 60

Synthesis of 3-(3,4-dimethoxybenzyl)-6-(fluoromethyl)-1-(tetrahydro-2H-pyran-4-yl)quinazoline-2,4(1H,3H)-dione

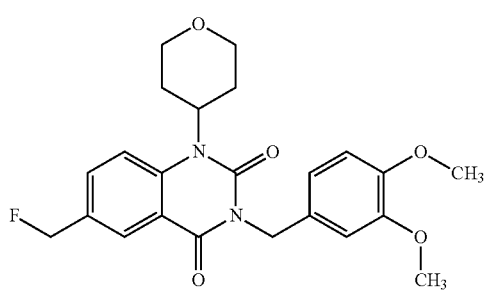 [SMILES: COc1ccc(Cn2c(=O)c3cc(CF)ccc3n(C3CCOCC3)c2=O)cc1OC]

Step 14.1:

3-(3,4-dimethoxybenzyl)-6-ethenyl-1-(tetrahydro-2H-pyran-4-yl)quinazoline-2,4(1H,3H)-dione

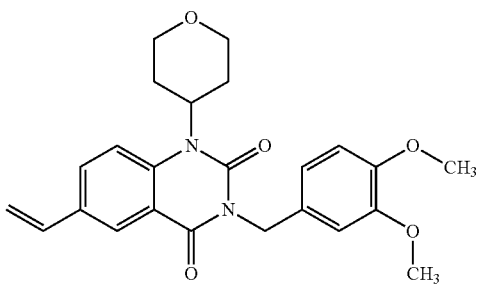 [SMILES: C=Cc1ccc2c(c1)c(=O)n(Cc1ccc(OC)c(OC)c1)c(=O)n2C1CCOCC1]

A mixture of 3.0 g of 3-(3,4-dimethoxybenzyl)-6-iodo-1-(tetrahydro-2H-pyran-4-yl)-quinazoline-2,4(1H,3H)-dione, 3.64 g of tributylvinyltin and Pd(PPh$_3$)$_4$ in 2 ml of toluene is irradiated in a microwave field for 30 minutes at 130° C. The reaction mixture is filtered and evaporated under reduced pressure. The residue is chromatographed on silica gel, eluting with a DCM/EtOAc mixture from (100/0, v/v) to (80/20, v/v) to give 1.4 g of the expected product.

Step 14.2:

3-(3,4-dimethoxybenzyl)-2,4-dioxo-1-(tetrahydro-2H-pyran-4-yl)-1,2,3,4-tetrahydro-quinazoline-6-carbaldehyde

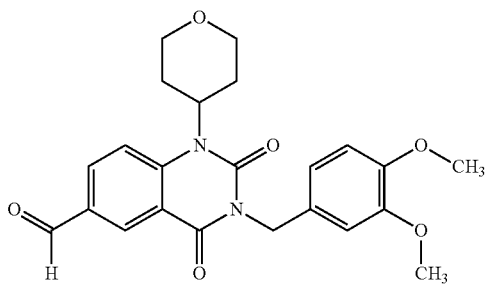 [SMILES: COc1ccc(Cn2c(=O)c3cc(C=O)ccc3n(C3CCOCC3)c2=O)cc1OC]

A stream of ozone is passed for 10 minutes through a solution of 1.4 g of the compound obtained in Step 14.1 in 100 ml of DCM cooled to −78° C. The reaction medium is degassed with nitrogen, 40 ml of dimethyl sulfide are added and the resulting mixture is stirred overnight at room temperature. The reaction medium is evaporated under reduced pressure. The residue is chromatographed on silica gel, eluting with a DCM/EtOAc mixture from (100/0, v/v) to (60/40, v/v) to give 0.58 g of the expected product.

Step 14.3:

3-(3,4-dimethoxybenzyl)-6-(hydroxymethyl)-1-(tetrahydro-2H-pyran-4-yl)quinazoline-2,4(1H,3H)-dione

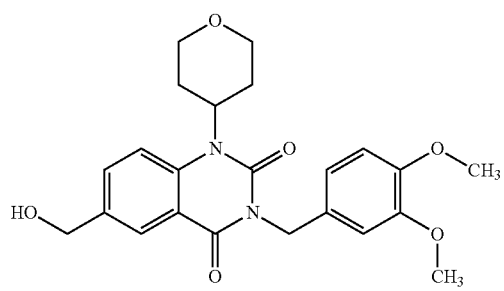 [SMILES: COc1ccc(Cn2c(=O)c3cc(CO)ccc3n(C3CCOCC3)c2=O)cc1OC]

A mixture of 0.575 g of the compound obtained in Step 14.2 and 0.077 g of NaBH$_4$ in a mixture of 20 ml of MeOH and 10 ml of THF is stirred for 30 minutes at room temperature. The reaction medium is evaporated under reduced pressure. The residue is taken up in DCM. This solution is washed with saturated NH$_4$Cl solution. The organic phase is dried over Na$_2$SO$_4$, filtered and evaporated under reduced pressure to give 0.554 g of the expected product.

Step 14.4:

3-(3,4-dimethoxybenzyl)-6-(fluoromethyl)-1-(tetrahydro-2H-pyran-4-yl)quinazoline-2,4(1H,3H)-dione

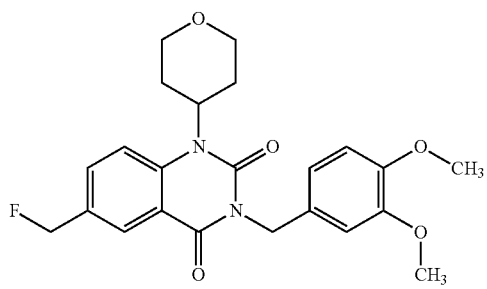 [SMILES: COc1ccc(Cn2c(=O)c3cc(CF)ccc3n(C3CCOCC3)c2=O)cc1OC]

0.11 ml of DAST is added dropwise to a solution of 0.1 g of the compound obtained in Step 14.3 in 2 ml of DCM cooled to −78° C. The reaction medium is stirred for 2 hours at −78° C. and then allowed to warm to room temperature. It is neutralized with saturated NaHCO$_3$ solution. The resulting mixture is extracted with DCM. The organic phase is dried over Na$_2$SO$_4$, filtered and evaporated under reduced pressure. The residue is chromatographed on silica gel, eluting with a DCM/EtOAc mixture from (95/5, v/v) to (30/70, v/v) to give 0.032 g of the expected product.

Example 15

Compound 59

Synthesis of 6-(2,2-difluoroethenyl)-3-(3,4-dimethoxybenzyl)-1-(tetrahydro-2H-pyran-4-yl)-quinazoline-2,4(1H,3H)-dione

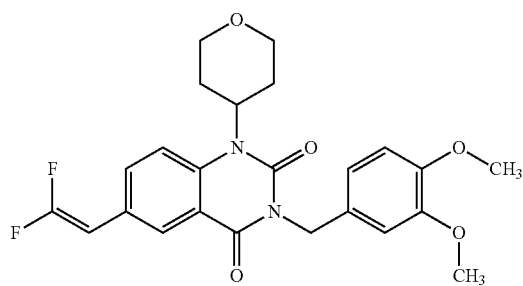 [SMILES: COc1ccc(Cn2c(=O)c3cc(C=C(F)F)ccc3n(C3CCOCC3)c2=O)cc1OC]

A solution of 0.121 mg of CBr$_2$F$_2$ and 0.096 g of HMPT in 0.5 ml of DME is added, at 0° C., to a solution of 0.12 g of 3-(3,4-dimethoxybenzyl)-2,4-dioxo-1-(tetrahydro-2H-pyran-4-yl)-1,2,3,4-tetrahydroquinazoline-6-carbaldehyde and 0.096 g of HMPT in 0.5 ml of DMF. This mixture is stirred overnight at room temperature. Aqueous 10% NaHCO$_3$ solution is added at 0° C. The resulting mixture is extracted with DCM. The organic phase is dried over Na$_2$SO$_4$, filtered and evaporated under reduced pressure. The residue is chromatographed on silica gel, eluting with a DCM/EtOAc mixture from (80/20, v/v) to give 0.023 g of the expected product.

Example 16

Compound 24

Synthesis of 3-(3,4-dimethoxybenzyl)-6-(2-hydroxyethyl)-1-(tetrahydro-2H-pyran-4-yl)-quinazoline-2,4(1H,3H)-dione

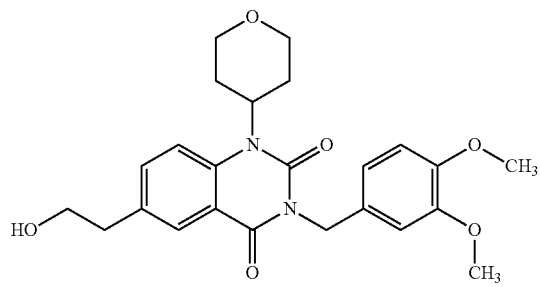 [SMILES: COc1ccc(Cn2c(=O)c3cc(CCO)ccc3n(C3CCOCC3)c2=O)cc1OC]

0.95 ml of a 1N solution of BH$_3$-THF complex in THF is added, at 0° C., to a mixture of 0.1 g of 3-(3,4-dimethoxybenzyl)-6-ethenyl-1-(tetrahydro-2H-pyran-4-yl)quinazoline-2,4(1H,3H)-dione in 2 ml of THF. The reaction medium is allowed to warm to room temperature and is stirred for 1 hour. 2 ml of 1N sodium hydroxide and then 2 ml of 30% aqueous hydrogen peroxide solution are added. The resulting mixture is refluxed for 1 hour and then extracted with DCM. The organic phase is dried over Na$_2$SO$_4$, filtered and evaporated under reduced pressure. The residue is chromatographed on silica gel, eluting with a DCM/EtOAc mixture from (80/20, v/v) to (40/60) to give 0.057 g of the expected product.

Example 17

Isomers 17 and 18

Synthesis of {[3-(3,4-dimethoxybenzyl)-1-(1-oxidotetrahydro-2H-thiopyran-4-yl)-2,4-dioxo-1,2,3,4-tetrahydroquinazolin-6-yl]oxy}acetonitrile

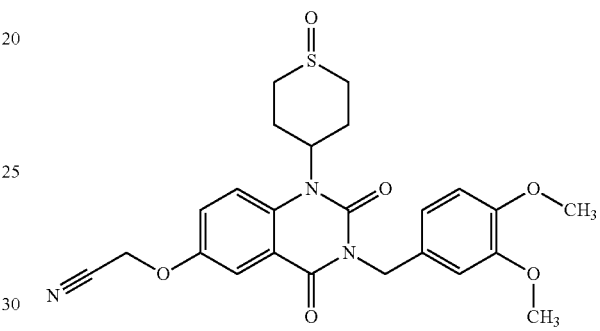

Step 17.1:

6-(benzyloxy)-3-(3,4-dimethoxybenzyl)-1-(1-oxidotetrahydro-2H-thiopyran-4-yl)-quinazoline-2,4(1H, 3H)-dione

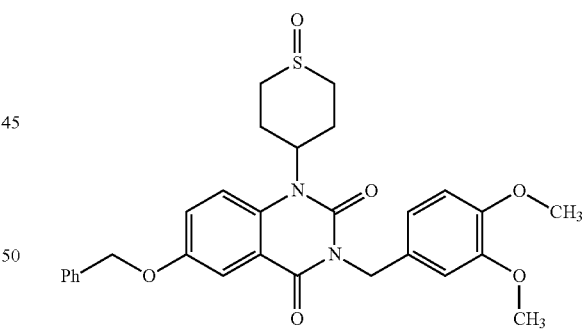

A mixture of 0.9 g of 6-(benzyloxy)-3-(3,4-dimethoxybenzyl)-1-(tetrahydro-2H-thiopyran-4-yl)quinazoline-2,4(1H, 3H)-dione and 0.445 g of sodium periodate in 20 ml of an MeOH/EtOH/water mixture (5/5/1, v/v/v) is stirred overnight at room temperature. The resulting mixture is evaporated under reduced pressure. Water is added and the resulting mixture is extracted with DCM. The organic phase is dried over Na$_2$SO$_4$. The resulting mixture is filtered, and the filtrate is evaporated under reduced pressure. The residue is chromatographed on silica gel, eluting with a DCM/MeOH mixture from (100/0, v/v) to (95/5, v/v) to give 0.99 g of the expected product.

Step 17.2:

3-(3,4-dimethoxybenzyl)-6-hydroxy-1-(1-oxidotetrahydro-2H-thiopyran-4-yl)quinazoline-2,4(1H,3H)-dione

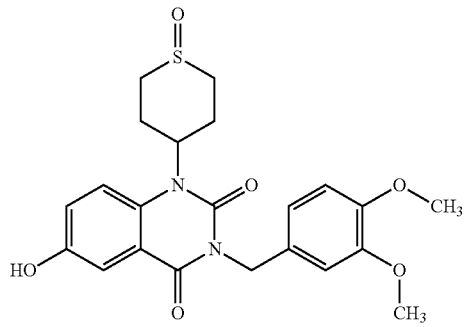 [SMILES: COc1ccc(Cn2c(=O)c3cc(O)ccc3n(C3CCS(=O)CC3)c2=O)cc1OC]

A mixture of 0.57 g of the compound of Step 17.1 and 10 ml of formic acid is irradiated in a microwave field for 3 minutes at 140° C. The reaction mixture is evaporated under reduced pressure. The residue is chromatographed on an RP18 column, eluting with an ACN/water mixture from (10/90, v/v) to (50/50, v/v) to give 0.443 g of the expected product in the form of a mixture of two isomers.

Step 17.3:

{[3-(3,4-dimethoxybenzyl)-1-(1-oxidotetrahydro-2H-thiopyran-4-yl)-2,4-dioxo-1,2,3,4-tetrahydro-quinazolin-6-yl]oxy}acetonitrile

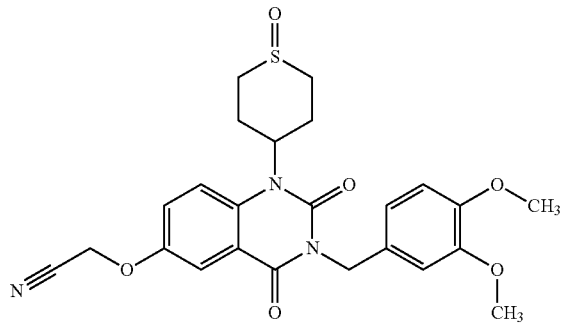 [SMILES: COc1ccc(Cn2c(=O)c3cc(OCC#N)ccc3n(C3CCS(=O)CC3)c2=O)cc1OC]

A mixture of 0.265 g of the compound obtained in Step 17.2, 0.086 g of bromoacetonitrile and 0.39 g of Cs$_2$CO$_3$ in 1 ml of DMF is irradiated in a microwave field for 15 minutes at 100° C. The reaction mixture is evaporated under reduced pressure. The residue is taken up in DCM, washed with water, dried over Na$_2$SO$_4$ and filtered, and the filtrate is evaporated under reduced pressure. The residue is chromatographed on silica gel, eluting with an MeOH/DCM mixture from (0.5/99.5, v/v) to (5/95, v/v) to give 128 mg of the less polar isomer (compound 17) and 98 mg of the more polar isomer (compound 18).

Example 18

Compound 14

Synthesis of {[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}acetonitrile

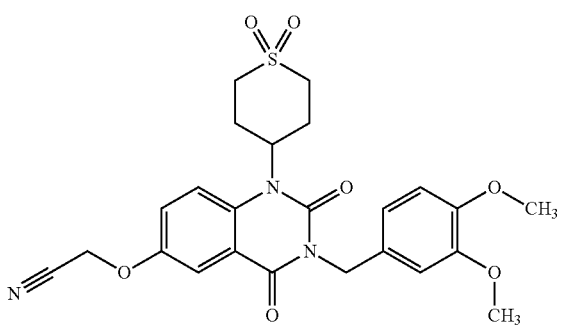 [SMILES: COc1ccc(Cn2c(=O)c3cc(OCC#N)ccc3n(C3CCS(=O)(=O)CC3)c2=O)cc1OC]

Step 18.1:

6-(benzyloxy)-3-(3,4-dimethoxybenzyl)-1-(1,1-dioxidotetrahydro-2H-thiopyran-4-yl)-quinazoline-2,4(1H,3H)-dione

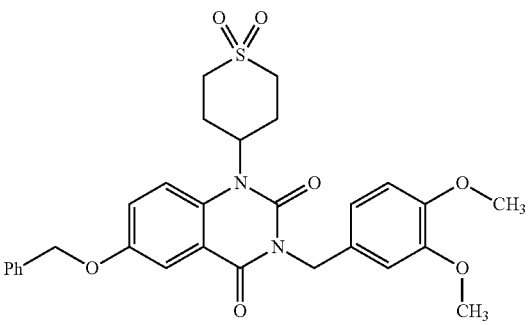 [SMILES: COc1ccc(Cn2c(=O)c3cc(OCc4ccccc4)ccc3n(C3CCS(=O)(=O)CC3)c2=O)cc1OC]

0.55 g of 6-(benzyloxy)-3-(3,4-dimethoxybenzyl)-1-(tetrahydro-2H-thiopyran-4-yl)-quinazoline-2,4(1H,3H)-dione and 0.196 g of Oxone® in 100 ml of an MeOH/water mixture (10/1) (v/v) is stirred at room temperature overnight. The resulting mixture is evaporated under reduced pressure. Water is added and the resulting mixture is extracted with DCM. The organic phase is dried over Na$_2$SO$_4$. The resulting solution is filtered and the filtrate is then evaporated under reduced pressure. The residue is chromatographed on silica gel, eluting with a heptane/EtOAc mixture from (50/50, v/v) to (0/100, v/v) to give 0.454 g of the expected product.

Step 18.2:

3-(3,4-dimethoxybenzyl)-1-(1,1-dioxidotetrahydro-2H-thiopyran-4-yl)-6-hydroxyquinazoline-2,4(1H,3H)-dione

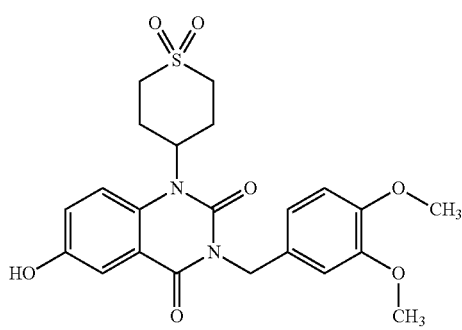 [SMILES: COc1ccc(Cn2c(=O)c3cc(O)ccc3n(C3CCS(=O)(=O)CC3)c2=O)cc1OC]

A mixture of 0.42 g of the compound obtained in Step 18.1 and 3.66 g of formic acid is irradiated in a microwave field for 10 minutes at 180° C. The reaction mixture is evaporated under reduced pressure. The residue is chromatographed on silica gel, eluting with a DCM/MeOH mixture from (100/0, v/v) to (90/10, v/v), to give the expected product.

Step 18.3:

{[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}acetonitrile

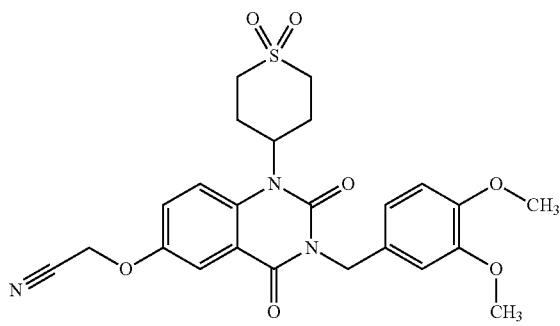

A mixture of 0.055 g of the compound obtained in Step 18.2, 0.017 g of bromoacetonitrile and 0.078 g of $Cs_2CO_3$ in 2 ml of DMF is irradiated in a microwave field for 15 minutes at 100° C. The reaction mixture is evaporated under reduced pressure. The residue is taken up in DCM, washed with water, dried over $Na_2SO_4$ and filtered, and the filtrate is evaporated under reduced pressure. The residue is chromatographed on silica gel, eluting with an MeOH/DCM mixture from (0.5/99.5, v/v) to (5/95, v/v), to give 0.043 g of the expected product.

The invention relates to a process for synthesizing a compound of general formula (I), the said process using an intermediate of formula (VIII), (X), (XVI), (XVII), (XVIII) and/or (XXIV), and also such synthetic intermediates defined previously.

The compounds according to the invention underwent pharmacological trials that showed their value as therapeutically active substances.

1) Measurement of the Inhibitory Activity of the Compounds According to the Invention with Respect to PDE7

The capacity of the compounds of formula (I) to inhibit PDE7 is measured by means of an enzymatic test based on separating radioactive cAMP (substrate of PDE7) from radioactive 5'-AMP (product of the enzymatic reaction) by thin-layer chromatography on polyethyleneimine (PEI) cellulose, after stopping the enzymatic reaction. The 5'-AMP is quantitatively extracted from the PEI cellulose and its radioactivity is measured using a liquid scintillation counter.

The inhibitory activity of the compounds of formula (I) on PDE7 is represented by the inhibition constant $IC_{50}$, defined as the concentration of test compound (inhibitor) in the trial that can reduce the enzymatic activity of PDE7 by 50%. The lower the $IC_{50}$ values, the greater the inhibitory power of the compounds.

Materials

[$^3$H]-cAMP (NET 275; 25 to 40 Ci/mmol) was purchased from Perkin-Elmer (NEN Life Sciences, Boston, United States), rolipram was purchased from Sigma (St Louis, Mo., United States), and the plastic polyethyleneimine cellulose F sheets for thin-layer chromatography were purchased from Merck (Darmstadt, Germany). All the other products are of commercial origin.

Enzyme

Human PDE7 was partially purified from the cell line HUT-78 by following a method similar to that described by Bloom and Beavo (Proc. Natl. Acad. Sci. USA, (1996) 93, 14188-14192). The enzyme preparation obtained is stored at −80° C. in a buffer containing 20 mM of Tris-HCl (pH 7.0), 5 mM of $MgCl_2$, 4 mM of EDTA, 1 mM of dithiothreitol and 20% glycerol. Since the partially purified PDE7 is contaminated with PDE4, it is necessary to add 10 µm of rolipram (selective PDE4 inhibitor) in the enzymatic test to totally inhibit the PDE4 activity. The Michaelis constant (Km) of PDE7 for cAMP, measured using the radiochemical test described hereinbelow, is 21 nM.

Solutions of Compounds in Accordance with the Invention

The compounds of formula (I) to be tested as PDE7 inhibitors are dissolved in DMSO to a concentration of 10 mM. These solutions are then serially diluted in DMSO to obtain solutions of desired concentrations. These solutions are then diluted 20-fold in the test buffer to give solutions containing 5% DMSO. These solutions are finally diluted 5-fold in the enzymatic test.

The solution of rolipram (added to the test to totally inhibit the contaminant PDE4 activity) is prepared in an identical manner and provides 1% of DMSO to the enzymatic test.

PDE7 Enzymatic Test

The test is performed in 1.5-ml Eppendorf tubes containing 40 mM of Tris-HCl (pH 7.5), 15 mM of $MgCl_2$, 1 mM of EGTA, 0.5 mg/ml of bovine serum albumin, 0.25 µCi of [$^3$H]-cAMP (corresponding to a cAMP concentration of between 60 and 100 nM), 10 µM of rolipram and PDE7 in a final volume of 100 µl. The test is performed in the absence (control sample) or in the presence (treated sample) of compounds tested as PDE7 inhibitors. The final concentration of DMSO in the test is 2%. The reaction is initiated by adding enzyme and the samples are maintained at room temperature for 30 minutes. The enzymatic dilution is adjusted so as to obtain a degree of conversion of 10% to 15%. The enzymatic reaction is stopped by immersing the stoppered Eppendorf tubes in a water bath at 100° C. for 3 minutes. Blanks (reaction stopped immediately after adding the enzyme) are included in each experiment. The samples are then centrifuged at 10 000×g for 1 minute and a 10 µl aliquot portion of the supernatant is deposited 2 cm from the bottom edge of a sheet of PEI cellulose onto which 10 μg of cAMP and 10 μg of 5'-AMP have previously been deposited. To facilitate the migration and the subsequent cutting of the PEI cellulose strips containing the 5'-AMP, 18 migration paths 1 cm wide are delimited per plate by scraping the cellulose with a spatula over a width of 1 mm. The plates are developed over their entire length with a 0.30 M solution of LiCl in water by ascending chromatography. The 5'-AMP (Rf=0.20) and the cAMP (Rf=0.47) are visualized under UV light at 254 nm. The PEI cellulose bands containing the 5'-AMP are cut out and the nucleotide is extracted quantitatively into counting flasks with 2 ml of a solution containing 16 M of formic acid and 2 M of ammonium formate in water (rotary stirring for 15 minutes). After adding 10 ml of scintillation liquid (OptiPhase HiSafe 3 from Perkin-Elmer/Wallac), the radioactivity is counted using a liquid scintillation counter (Perkin-Elmer/Wallac model 1414). Each test is performed in duplicate. The radioactivity specifically associated with the 5'-AMP formed in the enzymatic reaction is obtained by subtracting the mean value of the blanks from the mean value of the controls (or of the treated samples).

The percentage of inhibition of PDE7 at a given concentration of the test compound (inhibitor) is calculated using the equation: I %=[mean value of the controls−mean value of the treated samples]×100/[mean value of the controls−mean value of the blanks].

The $IC_{50}$ is the concentration of test compound (inhibitor) in the test that can reduce the enzymatic activity of PDE7 by 50%.

Results

As non-limiting illustrative examples, the $IC_{50}$ values for the following PDE7-inhibiting quinazolinediones are indicated hereinbelow in Table 2. In these examples, the $IC_{50}$ values were measured at a cAMP concentration equal to about 4 times the value of the Km of the enzyme for cAMP.

TABLE 2

| No. | Compounds according to the invention | IC50 (in μM) |
|---|---|---|
| 2 | (structure) | 0.0089 |
| 9 | (structure) | 0.016 |
| 11 | (structure) | 0.0055 |
| 17 | (structure) | 0.0061 |
| 45 | (structure) | 0.061 |
| 60 | (structure) | 0.012 |
| 14 | (structure) | 0.23 |

2) Measurement of the Inhibitory Activity of the Compounds in Accordance with the Invention Towards PDE8

Using an enzymatic test equivalent to that described for PDE7, compound 64 inhibits PDE8 by 59% at 0.1 μM.

The compounds according to the invention showed their value as active therapeutic substances. The compound(s) of formula (I) according to the invention may thus be useful as medicaments or for the preparation of medicaments.

According to another of its aspects, the invention relates to medicaments or pharmaceutical compositions comprising at least one compound of formula (I) according to the invention or an addition salt of this compound with a pharmaceutically acceptable acid and optionally with at least one pharmaceutically acceptable excipient.

The compounds of formula (I) according to the invention may be useful as medicaments or for the preparation of a medicament intended especially for treating and/or preventing inflammatory or immuno-inflammatory diseases.

The compounds of formula (I) according to the invention may be useful as medicaments or for the preparation of a medicament especially for treating and/or preventing asthma, chronic obstructive pulmonary disease (COPD), allergic rhinitis, allergies, Crohn's disease, ulcerative colitis, myasthenia gravis, atopic dermatitis, psoriasis, disseminated lupus erythematosus, rheumatoid arthritis, diabetes and multiple sclerosis.

The compounds according to the invention may be useful in the context of treating and/or preventing organ graft rejection, in particular for preventing rejection and/or in the treatment of immuno-inflammatory reactions following such grafts, in the treatment and/or prevention of certain types of cancer, for instance osteosarcoma and adenocarcinoma, in the treatment and/or prevention of bone diseases, for instance osteopenia and osteoporosis, in the treatment and/or prevention of acute renal insufficiency, or in the treatment and/or prevention of pain, in particular neuropathic pain and visceral pain.

The compounds of formula (I) according to the invention may also be used as medicaments or for the preparation of a medicament intended for treating at least a cardiovascular disease and/or for preventing the onset of at least a cardiovascular disease.

Examples of cardiovascular diseases that may be mentioned include (i) coronary diseases, (ii) heart muscle diseases, (iii) heart valve diseases, (iv) pericardium diseases, (v) heart rhythm diseases and heart conduction diseases, and (vi) blood vessel diseases.

According to the invention, the compounds of formula (I) in accordance with the invention may be used as medicaments or for the preparation of a medicament for treating and/or preventing the onset of myocardial infarction, diseases associated with reperfusion lesions of heart muscle and/or skeletal muscle, pulmonary hypertension, hepatic fibrosis, arterial restenosis after angioplasty, with or without the insertion of a stent, atherosclerosis and complications thereof, for instance plaque rupture, aneurysm and coronary diseases, cardiac insufficiency, dilated cardiopathies and myocarditis of viral and/or bacterial origin.

The compounds of formula (I) according to the invention may be useful as medicaments or for the preparation of a medicament especially for treating and/or preventing disorders related to the central nervous system (abbreviated as CNS) and/or related to the peripheral nervous system (abbreviated as PNS).

The compounds of formula (I) according to the invention may be more particularly useful as medicaments or for the preparation of a medicament for treating and/or preventing psychiatric disorders and/or neurological disorders.

According to the invention, the compounds of formula (I) in accordance with the invention may be used as medicaments or for the preparation of a medicament for treating and/or preventing psychiatric disorders chosen from anxiety, depression, mood disorders, insomnia, delirium disorders, obsessive disorders, psychoses, schizophrenia-related disorders, attention deficit hyperactivity disorder (ADHD) in hyperkinetic children, disorders associated with the use of psychotropic substances, especially in the case of substance abuse and/or substance dependency, including alcohol dependency and/or nicotine dependency, migraine, stress, disorders related to diseases of psychosomatic origin, panic attacks, epilepsy, memory disorders, cognitive disorders, in particular senile dementia, disorders related to Alzheimer's disease, and also attention or vigilance disorders, ischaemia, disorders related to cranial trauma, and disorders related to acute or chronic neurodegenerative diseases, including chorea and Huntington's chorea.

According to the invention, the compounds of formula (I) in accordance with the invention may be used as medicaments or for the preparation of a medicament for treating and/or preventing neurological diseases, which may be reflected by movement anomalies or motor disorders, associated with a pathology chosen from dyskinesia, Parkinson's disease, post-encephalitic Parkinson's syndrome, dopa-sensitive dystonia, Shy-Drager's syndrome, periodic limb movement disorder (PLMD), periodic limb movements in sleep (PLMS), Tourette's syndrome, and restless leg syndrome (RLS).

According to the invention, the compounds of formula (I) may be used as medicaments or for manufacturing a medicament for treating at least one movement anomaly or motor disorder related to Parkinson's disease, the said movement anomaly or the said motor disorder being chosen in particular from resting tremor, rigour, bradykinesia and postural reflex deficiency.

According to the invention, the compounds of formula (I) may be used as medicaments or for the manufacture of a medicament for preventing and/or treating neurological disorders reflected by movement anomalies or motor disorders, associated with spinal column trauma, in particular in the treatment of spinal trauma. For the purposes of the present invention, the term "spinal column trauma" means acute or chronic pathologies with an external origin, which destroy the spinal tract and/or neurones, and which occur, for example, during a fall, a knock, crushing or a circulatory accident.

The compounds of formula (I) according to the invention may be used especially as medicaments or for the manufacture of a medicament for preventing and/or treating disorders:
  associated with schizophrenia, in particular (i) in the prevention and/or treatment of positive or negative symptoms and/or (ii) in the prevention and/or treatment of memory deficiency;
  associated with Parkinson's disease, in particular (i) in the symptomatic prevention and/or treatment of motor disorders, depression and/or cognitive disorders, and/or (ii) in its fundamental treatment (neuroprotective); and/or
  related to Alzheimer's disease, in particular (i) in the symptomatic prevention and/or treatment of cognitive disorders and/or behavioural disorders (aggressiveness, depression) and/or (ii) in its fundamental treatment (neuroprotective).

The use of the compounds of general formula (I) as medicaments or for the preparation of a medicament for treating the conditions, diseases or syndromes mentioned above forms an integral part of the invention, and in particular the compounds of formula (I) chosen from compounds 1 to 68 of Table 1 above.

According to another of its aspects, the present invention relates to pharmaceutical compositions comprising, as active principle, at least one compound of formula (I) according to the invention. These pharmaceutical compositions contain an effective dose of at least one compound of formula (I) according to the invention, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the complaints, disorders, syndromes or diseases mentioned above.

The appropriate unit forms of administration include oral-route forms such as tablets, soft or hard gel capsules, powders, granules and oral solutions or suspensions, sublingual, buccal, intratracheal, intraocular, intranasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention, in particular a compound of formula (I) chosen from compounds 1 to 68 of Table 1 above, in tablet form may comprise the following components:

| | |
|---|---|
| Compound of formula (I) according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.5 mg to 800 mg of active principle per individual, and more particularly from 0.5 mg to 200 mg, according to the pharmaceutical form.

There may be cases where higher or lower dosages are appropriate: such dosages do not depart from the scope of the invention. According to the usual practice, the dosage that is appropriate to each patient is determined by the doctor according to the mode of administration and the weight and response of the said patient.

According to another of its aspects, the present invention also relates to a method for treating and/or preventing the complaints, disorders, syndromes or diseases mentioned above, which comprises the administration to patient of an effective amount of at least one compound of formula (I) according to the invention and/or at least one salt, hydrate or solvate thereof.

The invention claimed is:

1. A compound of formula (I):

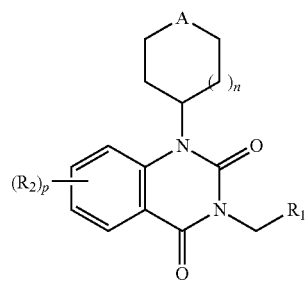

(I)

in which A represents either an oxygen or sulfur atom, or a sulfoxide function (SO function) or a sulfone function ($SO_2$ function);

n represents the value 1;

$R_2$ represents an atom or a group chosen from:
a hydrogen atom,
a halogen atom,
a cyano group,
a nitro group,
an aryl, arylalkyl or heteroaryl group,
a group ($C_1$-$C_6$)alkyl, optionally substituted with a function —$NH_2$, with one or more halogen atoms, with one or more hydroxyl groups, with an alkynyl group, with an alkenyl group, with a group —NHC(O)Rb and/or with a group —NHC(O)—NRbRc, Rb and Rc being defined below,
a group —ORa, Ra being defined below,
a group NRbRc, Rb and Rc being defined below,
a group C(O)($C_1$-$C_6$)alkyl,
an alkenyl group or an alkynyl group, the said groups being optionally substituted with at least one hydroxyl or with at least one halogen atom;
a group alkyl-S—,
alkyl-S(O)—, and
alkyl-S(O)$_2$—,
    p represents the value 1, 2 or 3, it being understood that when p is equal to 2 or 3, then the atoms $R_2$ or the groups $R_2$ may be, respectively, identical or different;
$R_1$ represents an aryl, arylalkyl or heteroaryl group, the said groups being optionally substituted with (i) an atom $R_3$ or a group $R_3$, or with (ii) 2 or 3 atoms and/or groups $R_3$, the said atoms or groups $R_3$ being, respectively, identical or different,
given that $R_3$ represents:
a hydrogen atom,
a halogen atom,
a hydroxyl group,
a cyano group,
a group —$SCF_3$,
a nitro group,
a group —S(O)$_{0-2}$-alkyl, a group —S(O)$_{0-2}$-heterocycloalkyl, a group —O—$SO_2$-aryl or O—$SO_2$-arylalkyl optionally substituted with one or more halogen atoms;
an alkyl-amino-alkyl group or a -cycloalkyl-amino-alkyl group, the said groups being optionally substituted on the terminal alkyl,
an optionally substituted sulfonamide group,
an aryl, arylalkyl or heteroaryl group, the said group being monocyclic or polycyclic and moreover being optionally substituted with a group ($C_1$-$C_6$)alkyl, with one or more hydroxyl groups, with one or more halogen atoms, with one or more cyano groups and/or with one or more groups ($C_1$-$C_6$)alkoxy,
a heterocycloalkyl group optionally substituted with a group ($C_1$-$C_6$)alkyl,
a group ($C_1$-$C_6$)alkyl optionally substituted with:
    one or more halogen atoms,
    an aryl or arylalkyl group that may be substituted with one or more halogen atoms, with one or more groups ($C_1$-$C_6$)alkoxy, with one or more groups ($C_1$-$C_6$)alkyl, with one or more cyano groups and/or with one or more hydroxyl groups,
    a heteroaryl group,
    one or more hydroxyl groups that may be substituted with an aryl or arylalkyl group, which is itself optionally substituted with one or more halogen atoms, or
    a heterocycloalkyl group optionally substituted with a group CO(O)Ra, or with a group ($C_1$-$C_6$)alkyl, Ra being defined below,
a group —C(O)NRbRc, Rb and Rc being defined below, a group —C(O)ORc, or a group —O—C(O)ORc, Rc being defined below, a group ($C_1$-$C_6$)alkoxy, optionally substituted with:
  an amino-alkyl group, an amino-cycloalkyl group,
  a cycloalkyl group,
  a heterocycloalkyl group,
  a monocyclic or polycyclic heteroaryl group,
  one or more hydroxyl groups,
  one or more halogen atoms,
  a group ($C_1$-$C_6$)alkoxy,
  a group —C(O)ORc, Rc being defined below,
  a group —C(O)NRbRc, Rb and Rc being defined below, and/or
  an aryl or arylalkyl group, which is itself optionally substituted with at least one atom and/or at least one group, the said atoms and groups being chosen from halogen atoms, a cyano group, groups ($C_1$-$C_6$)alkoxy, —O-haloalkyl groups and haloalkyl groups, a group —O-cycloalkyl, —O-aryl or —O-arylalkyl, or a group —O-heterocycloalkyl, the said groups being optionally substituted with:
  an aryl or arylalkyl group, which is itself optionally substituted with one or more halogen atoms, or with a group ($C_1$-$C_6$)alkyl,
  one or more halogen atoms, and/or
  a group ($C_1$-$C_6$)alkyl, which may itself be substituted with an aryl or arylalkyl group, a group —NH—CO—NH-aryl, a group —NH—CO—NH-arylalkyl, a group —NH—CO—NH-heteroaryl, or a group —NH—CO—NH—($C_1$-$C_6$)alkyl, the said aryl, arylalkyl, heteroaryl and alkyl being optionally substituted with at least one atom and/or at least one group, the said atoms and groups being chosen from halogen atoms, a cyano group, a nitro group, a hydroxyl group and groups ($C_1$-$C_6$)alkoxy, a group —N—($C_1$-$C_6$)alkyl, the group ($C_1$-$C_6$)alkyl possibly being substituted with at least one aryl or arylalkyl group optionally substituted with at least one halogen atom and/or with at least one group $SO_2$, or a group —NH—C(O)-aryl, a group —NH—C(O)-aralkyl or a group —NH—C(O)-heteroaryl, the said groups being optionally substituted with at least one halogen atom;

Ra represents:
  a hydrogen atom,
  a group ($C_1$-$C_6$)alkyl or a group ($C_1$-$C_6$)cycloalkyl, the said groups being optionally substituted with one or more halogen atoms, with one or more hydroxyl groups, with an aryl or arylalkyl group, with one or more cyano groups and/or with a group —C(O)NRbRc, Rb and Rc being defined below,
  a group ($C_2$-$C_6$)alkynyl,
  an aryl or arylalkyl group, Rb represents:
  a hydrogen atom,
  a group ($C_1$-$C_6$)alkyl optionally substituted with one or more halogen atoms, with one or more hydroxyl, cyano, amino, heterocycloalkyl or ($C_1$-$C_6$)alkoxy groups, or with an aryl or arylalkyl group optionally substituted with one or more halogen atoms,
  a group ($C_3$-$C_6$) cycloalkyl,
  a group ($C_2$-$C_6$) alkenyl or alkynyl,
  a group ($C_1$-$C_6$)alkoxy,
  an aryl or arylalkyl group optionally substituted with one or more halogen atoms;

Rc represents a hydrogen atom, or a group ($C_1$-$C_6$) alkyl optionally substituted with one or more halogen atoms;

given that in the groups —NRbRc, Rb and Rc may form with the nitrogen atom a heteroaryl or a heterocycloalkyl, the latter groups being optionally substituted;

in the form of the base or of an acid-addition salt.

2. The compound according to claim 1, which is:
compound 1: 3-(3,4-dimethoxybenzyl)-6-hydroxy1-(tetrahydro-2H-pyran-4-yl)quinazoline-2,4(1H,3H)-dione;
compound 2: {[3-(3,4-dimethoxybenzyl)-2,4-dioxo-1-(tetrahydro-2H-pyran-4-yl)1,2,3,4-tetrahydroquinazolin-6-yl]oxy}acetonitrile;
compound 3: 3-(3,4-dimethoxybenzyl)-6-pyridin-4-yl1-(tetrahydro-2H-pyran-4-yl)-quinazoline-2,4(1H,3H)-dione hydrochloride;
compound 4: 3[(6-methoxypyridin-3-yl)methyl]-6-pyridin-4-yl 1-(tetrahydro-2H-pyran-4-yl)-quinazoline-2,4 (1H,3H)-dione;
compound 5: 6-bromo-3[(6-methoxypyridin-3-yl)methyl] 1-(tetrahydro-2H-pyran-4-yl)-quinazoline-2,4(1H,3H)-dione;
compound 6: 6-bromo-3-(3,4-dimethoxybenzyl)1-(tetrahydro-2H-pyran-4-yl)quinazoline-2,4(1H,3H)-dione
compound 7: 2-({3[(6-methoxypyridin-3-yl)methyl]-2,4-dioxo1-(tetrahydro-2H-pyran-4-yl)-1,2,3,4-tetrahydroquinazolin-6-yl}oxy)propanenitrile
compound 8: 2-{[3-3,4-dimethoxybenzyl)-2,4-dioxo-1-(tetrahydro-2H-pyran-4-yl)1,2,3,4-tetrahydroquinazolin-6-yl]oxy}propanenitrile
compound 9:({3-[(6-methoxypyridin-3-yl)methyl]-2,4-dioxo-1-(tetrahydro-2H-pyran-4-yl)-1,2,3,4-tetrahydroquinazolin-6-yl}oxy)acetonitrile
compound 10: 3-(3,4-dimethoxybenzyl)-6-hydroxy-1-(tetrahydro-2H-thiopyran-4-yl)-quinazoline-2,4(1H, 3H)-dione
compound 11: {[3-(3,4-dimethoxybenzyl)-2,4-dioxo-1-(tetrahydro-2H-thiopyran-4-yl)-1,2,3,4-tetrahydroquinazolin-6-yl]oxy}acetonitrile
compound 12: 2{[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}propanenitrile
compound 13: 3-(3,4-dimethoxybenzyl)-6-hydroxy-1-(1-oxidotetrahydro-2H-thiopyran-4-yl)-quinazoline-2,4 (1H,3H)-dione
compound 14: {[3-(3,4-dimethoxybenzyl)-1-(1,1-dioxidotetrahydro-2H-thiopyran-4-yl)-2,4-dioxo-1,2,3,4-tetrahydroquinazolin-6-yl]oxy}acetonitrile
compound 15: 2{[3-(3,4-dimethoxybenzyl)-1-(1-oxidotetrahydro-2H-thiopyran-4-yl)-2,4-dioxo-1,2,3,4-tetrahydroquinazolin-6-yl]oxy}propanenitrile (isomer 1)
compound 16: 2{[3-(3,4-dimethoxybenzyl)-1-(1-oxidotetrahydro-2H-thiopyran-4-yl)-2,4-dioxo-1,2,3,4-tetrahydroquinazolin-6-yl]oxy}propanenitrile (isomer 2)
compound 17: {[3-(3,4-dimethoxybenzyl)-1-(1-oxidotetrahydro-2H-thiopyran-4-yl)-2,4-dioxo-1,2,3,4-tetrahydroquinazolin-6-yl]oxy}acetonitrile (isomer 1)
compound 18: {[3-(3,4-dimethoxybenzyl)-1-(1-oxidotetrahydro-2H-thiopyran-4-yl)-2,4-dioxo-1,2,3,4-tetrahydroquinazolin-6-yl]oxy}acetonitrile (isomer 2)
compound 19: 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrilemethane (1:1) (enantiomer 1)

compound 20: 2-{[3-(3,4-dimethoxybenzyl)-2,4-dioxo-1-(tetrahydro-2H-pyran-4-yl)-1,2,3,4-tetrahydroquinazolin-6-yl]oxy}propanenitrilemethane (1:1) (enantiomer 2)

compound 21:3-(3,4-dimethoxybenzyl)-6-(prop-2-yn-1-yloxy)-1-(tetrahydro-2H-pyran-4-yl)-quinazoline-2,4(1H,3H)-dione compound 22: 2{[3-(3,4-dimethoxybenzyl)-2,4-dioxo-1-(tetrahydro-2H-pyran-4-yl)-1,2,3,4-tetrahydroquinazolin-6-yl]oxy}-2-methylpropanenitrile compound 23: 2-{[3-(3,4-dimethoxybenzyl)-2,4-dioxo-1-(tetrahydro-2H-pyran-4-yl)-1,2,3,4-tetrahydroquinazolin-6-yl]oxy}-2-methylpropanamide compound 24: 3-(3,4-dimethoxybenzyl)-6-(2-hydroxyethoxy)-1-(tetrahydro-2H-pyran-4-yl)-quinazoline-2,4(1H,3H)-dione compound 25: 6-(cyclopropylmethoxy)-3-(3,4-dimethoxybenzyl)-1-(tetrahydro-2H-pyran-4-yl)quinazoline-2,4(1H,3H)-dione compound 26: 3-(3,4-dimethoxybenzyl)-6-[(1-methylprop-2-yn-1-yl)oxy]-1-(tetrahydro-2H-pyran-4-yl)quinazoline-2,4(1H,3H)-dione compound 27: 3-(3,4-dimethoxybenzyl)-6-(3-hydroxyazetidin-1-yl)-1-(tetrahydro-2H-pyran-4-yl)quinazoline-2,4(1H,3H)-dione compound 28: 3-(3,4-dimethoxybenzyl)-6-(prop-2-yn-1-ylamino)-1-(tetrahydro-2H-pyran-4-yl)quinazoline-2,4(1H,3H)-dione compound 29: 3-(3,4-dimethoxybenzyl)-2,4-dioxo-1-(tetrahydro-2H-pyran-4-yl)-1,2,3,4-tetrahydroquinazoline-6-carbonitrile compound 30: N{[3-(3,4-dimethoxybenzyl)-2,4-dioxo-1-(tetrahydro-2H-pyran-4-yl)-1,2,3,4-tetrahydroquinazolin-6-yl]methyl}acetamide compound 31: 1-{[3-(3,4-dimethoxybenzyl)-2,4-dioxo-1-(tetrahydro-2H-pyran-4-yl)-1,2,3,4-tetrahydroquinazolin-6-yl]methyl}urea compound 32: 3-(3,4-dimethoxybenzyl)-6-[(1-methylprop-2-yn-1-oxy]-1-(tetrahydro-2H-pyran-4-yl)quinazoline-2,4(1H,3H)-dione (enantiomer 1)

compound 33: 3-(3,4-dimethoxybenzyl)-6-[(1-methylprop-2-yn-1-yl)oxy]-1-(tetrahydro-2H-pyran-4-yl)quinazoline-2,4(1H,3H)-dione (enantiomer 2)

compound 34: 3-(3,4-dimethoxybenzyl)-6-iodo-1-(tetrahydro-2H-pyran-4-yl)quinazoline-2,4(1H,3H)-dione compound 35: 3-(3,4-dimethoxybenzyl)-6-[(1-methylprop-2-yn-1-yl)amino]-1-(tetrahydro-2H-pyran-4-yl)quinazoline-2,4(1H,3H)-dione compound 36: 3-(3,4-dimethoxybenzyl)-6-propoxy-1-(tetrahydro-2H-pyran-4-yl)quinazoline-2,4(1H,3H)-dione compound 37: 3-(3,4-dimethoxybenzyl)-6-(2-methylpropoxy)-1-(tetrahydro-2H-pyran-4-yl)-quinazoline-2,4(1H,3H)-dione compound 38: 3-(3,4-dimethoxybenzyl)-6-(1-methylethoxy)-1-(tetrahydro-2H-pyran-4-yl)-quinazoline-2,4(1H,3H)-dione compound 39: 3-(3,4-dimethoxybenzyl)-6-(1-hydroxyethyl)-1-(tetrahydro-2H-pyran-4-yl)-quinazoline-2,4(1H,3H)-dione compound 40: 6-acetyl-3-(3,4-dimethoxybenzyl)-1-(tetrahydro-2H-pyran-4-yl)quinazoline-2,4(1H,3H)-dione compound 41: 6-(2,3-dihydroxypropoxy)-3-(3,4-dimethoxybenzyl)-1-(tetrahydro-2H-pyran-4-yl)quinazoline-2,4(1H,3H)-dione compound 42: 3-(3,4-dimethoxybenzyl)-6-(2-hydroxypropoxy)-1-(tetrahydro-2H-pyran-4-yl)-quinazoline-2,4(1H,3H)-dione compound 43: 3-(3,4-dimethoxybenzyl)-6-(1-hydroxy-1-methylethyl)-1-(tetrahydro-2H-pyran-4-yl)quinazoline-2,4(1H,3H)-dione compound 44: 3-(3,4-dimethoxybenzyl)-6-ethenyl-1-(tetrahydro-2H-pyran-4yl)quinazoline-2,4(1H,3H)dione compound 45: 3(3,4-dimethoxybenzyl)-6-(hydroxymethyl)-1-(tetrahydro -2H-pyran-4-yl)-quinazoline-2,4(1H,3H)dione compound 46: 3-(3,4-dimethoxybenzyl)-6-(1-hydroxy-1-methylbut-3-yn-1-yl)1-(tetrahydro-2H-pyran-4-yl)quinazoline-2,4(1H,3H)-dione compound 47: 3-(3,4-dimethoxybenzyl)-6-(2-hydroxyethyl)-1(tetrahydro-2H-pyran-4-yl)-quinazoline-2,4(1H,3H)dione compound 48: 3(3,4-dimethoxybenzyl)-6-[(1R)-2-hydroxy-1-methylethoxy]1(tetrahydro-2H-pyran-4-yl)quinazoline-2,4(1H,3H)-dione compound 49: 3(3,4-dimethoxybenzyl)-6-ethoxy-1-(tetrahydro-2H-pyran-4-yl)quinazoline-2,4(1H,3H)-dione compound 50: 3-(3,4-dimethoxybenzyl)-6-(2-fluoroethoxy)-1-(tetrahydro -2H-pyran4yl)-quinazoline-2,4(1H,3H)-dione compound 51: 3-(3,4-dimethoxybenzyl)-1-(tetrahydro-2H-pyran-4-yl)-6-(2,2,2-trifluoroethoxy)quinazoline-2,4(1H,3H)-dione compound 52: 3-(3,4-dimethoxybenzyl)-6-[(1S)-2-hydroxy-1-methylethoxy]-1-(tetrahydro-2H-pyran-4-yl)quinazoline-2,4(1H,3H)-dione compound 53: 6-(2,2difluoroethoxy)-3(3,4-dimethoxybenzyl)1(tetrahydro-2H-pyran-4yl)-quinazoline-2,4(1H,3H)-dione compound 54: 3-(3,4-dimethoxybenzyl)-1(tetrahydro-2H-pyran-4-yl)-6-(3,3,3-trifluoropropoxy)quinazoline-2,4(1H,3H)-dione compound 55: 3-(3,4-dimethoxybenzyl)-6-{[(1R)-1-methylpropyl]oxy}-1-(tetrahydro -2H-pyran-4-yl) quinazoline-2,4(1H,3H)-dione compound 56: 3-(3,4-dimethoxybenzyl)-6-{[(1S)-1-methylpropyl]oxy}-1(tetrahydro-2H-pyran-4yl) quinazoline-2,4(1H,3H)dione compound 57: 3(3,4-dimethoxybenzyl)-6-[2-fluoro-1(fluoromethyl)ethoxy]-1-(tetrahydro-2H-pyran-4-yl) quinazoline-2,4(1H,3H)-dione compound 58: 3-(3,4-dimethoxybenzyl)-6-[(1S)-2-fluoro-1-methylethoxy]-1-(tetrahydro-2H-pyran-4-yl) quinazoline-2,4(1H,3H)-dione compound 59: 6(2,2-difluoroethenyl)-3-(3,4-dimethoxybenzyl)1(tetrahydro -2H-pyran-4-yl)-quinazoline-2,4 (1H,3H)-dione compound 60: 3-(3,4dimethoxybenzyl)-6-(fluoromethyl)-1-(tetrahydro-2H-pyran-4-yl)-quinazoline-2,4(1H,3H)-dione compound 61: 3-(3,4-dimethoxybenzyl)-7-fluoro-6-hydroxy1(tetrahydro-2H-pyran-4-yl)-quinazoline-2,4 (1H,3H)-dione compound 62: 6-(benzyloxy)-3-(3,4-dimethoxybenzyl)-7fluoro-1-(tetrahydro-2H-pyran-4-yl)quinazoline-2,4 (1H,3H)-dione compound 63: 6-(2,2-difluoroethoxy)-3-(3,4-dimethoxybenzyl)-7-fluoro-1-(tetrahydro-2H-pyran-4-yl) quinazoline-2,4(1H,3H)-dione compound 64: 3-[4-(benzyloxy)-3-methoxybenzyl]-6-[(1,3-difluoropropan-2-yl)oxy]-7-fluoro-1-(tetrahydro-2H-pyran-4-yl)quinazoline-2,4(1H,3H)-dione compound 65: 3-{4[(3,4-dichlorobenzyl)oxy]-3-methoxybenzyl}-6-[(1,3-difluoropropan-2-yl)oxy]-7-fluoro-1-(tetrahydro-2H-pyran-4-yl)quinazoline-2,4(1H,3H)-dione compound 66: 3-(3,4-dimethoxybenzyl)-6-nitro-1-(tetrahydro-2H-pyran-4-yl)quinazoline-2,4(1H,3H)-dione compound 67: 6-amino-3-(3,4-dimethoxybenzyl)-1-(tetrahydro-2H-pyran-4-yl)quinazoline-2,4(1H,3H)-dione compound 68: 6[(1,3-difluoropropan-2-yl)oxy]-7-fluoro-3-(4-hydroxy-3-methoxybenzyl)-1-(tetrahydro-2H-pyran-4-yl)quinazoline-2,4(1H,3H)-dione;

in the form of the base or of an acid-addition salt.

3. A pharmaceutical composition, comprising the compound according to claim 1, or an addition salt with a pharmaceutically acceptable acid thereof, and also at least one pharmaceutically acceptable excipient.

4. A pharmaceutical composition, comprising the compound according to claim 2, or an addition salt with a pharmaceutically acceptable acid thereof, and also at least one pharmaceutically acceptable excipient.

* * * * *